(12) United States Patent
Vidlund et al.

(10) Patent No.: US 11,123,180 B2
(45) Date of Patent: Sep. 21, 2021

(54) PROSTHETIC VALVES AND RELATED INVENTIONS

(71) Applicant: Tendyne Holdings, Inc., St. Paul, MN (US)

(72) Inventors: Robert Vidlund, Forest Lake, MN (US); Kemal Schankereli, Stillwater, MN (US); Lucian Lozonschi, Madison, WI (US); Georg Lutter, Kiel (DE)

(73) Assignee: Tendyne Holdings, Inc., St. Paul, MN (US)

( * ) Notice: Subject to any disclaimer, the term of this patent is extended or adjusted under 35 U.S.C. 154(b) by 192 days.

(21) Appl. No.: 16/594,263

(22) Filed: Oct. 7, 2019

(65) Prior Publication Data

US 2020/0030088 A1 Jan. 30, 2020

Related U.S. Application Data

(60) Continuation of application No. 15/829,091, filed on Dec. 1, 2017, now Pat. No. 10,639,145, which is a (Continued)

(51) Int. Cl.
*A61F 2/24* (2006.01)
*A61L 27/34* (2006.01)
(Continued)

(52) U.S. Cl.
CPC .......... *A61F 2/2412* (2013.01); *A61F 2/2409* (2013.01); *A61F 2/2418* (2013.01); (Continued)

(58) Field of Classification Search
CPC .......... A61F 2/24; A61F 2/2418; A61F 2/2409
(Continued)

(56) References Cited

U.S. PATENT DOCUMENTS

| 2,697,008 A | 12/1954 | Ross |
| 3,409,013 A | 11/1968 | Berry |

(Continued)

FOREIGN PATENT DOCUMENTS

| CA | 2844746 A1 | 2/2013 |
| CA | 2957442 C | 2/2013 |

(Continued)

OTHER PUBLICATIONS

US 9,155,620 B2, 10/2015, Gross et al. (withdrawn)

(Continued)

*Primary Examiner* — Suzette J Gherbi
(74) *Attorney, Agent, or Firm* — Lerner, David, Littenberg, Krumholz & Mentlik, LLP

(57) ABSTRACT

This invention relates to the design and function of a compressible valve replacement prosthesis, collared or uncollared, which can be deployed into a beating heart without extracorporeal circulation using a transcatheter delivery system. The design as discussed focuses on the deployment of a device via a minimally invasive fashion and by way of example considers a minimally invasive surgical procedure preferably utilizing the intercostal or subxyphoid space for valve introduction. In order to accomplish this, the valve is formed in such a manner that it can be compressed to fit within a delivery system and secondarily ejected from the delivery system into the annulus of a target valve such as a mitral valve or tricuspid valve.

17 Claims, 69 Drawing Sheets

Related U.S. Application Data continuation of application No. 15/183,943, filed on Jun. 16, 2016, now Pat. No. 9,833,315, which is a division of application No. 14/237,023, filed as application No. PCT/US2012/050579 on Aug. 13, 2012, now Pat. No. 9,480,559.

(60) Provisional application No. 61/615,264, filed on Mar. 24, 2012, provisional application No. 61/564,462, filed on Nov. 29, 2011, provisional application No. 61/523,134, filed on Aug. 12, 2011, provisional application No. 61/522,468, filed on Aug. 11, 2011, provisional application No. 61/522,542, filed on Aug. 11, 2011, provisional application No. 61/522,450, filed on Aug. 11, 2011, provisional application No. 61/522,476, filed on Aug. 11, 2011.

(51) Int. Cl.
*A61L 27/36* (2006.01)
*A61L 33/00* (2006.01)
*C08L 67/04* (2006.01)
*A61B 17/04* (2006.01)
*A61B 17/064* (2006.01)

(52) U.S. Cl.
CPC ............ *A61F 2/2427* (2013.01); *A61L 27/34* (2013.01); *A61L 27/3625* (2013.01); *A61L 27/3629* (2013.01); *A61L 33/0011* (2013.01); *C08L 67/04* (2013.01); *A61B 17/0401* (2013.01); *A61B 17/064* (2013.01); *A61B 17/0644* (2013.01); *A61B 2017/0404* (2013.01); *A61F 2/2436* (2013.01); *A61F 2/2457* (2013.01); *A61F 2210/0004* (2013.01); *A61F 2210/0014* (2013.01); *A61F 2220/005* (2013.01); *A61F 2220/0008* (2013.01); *A61F 2220/0058* (2013.01); *A61F 2220/0091* (2013.01); *A61F 2230/005* (2013.01); *A61F 2230/0013* (2013.01); *A61F 2230/0034* (2013.01); *A61F 2230/0054* (2013.01); *A61F 2230/0067* (2013.01); *A61F 2230/0091* (2013.01); *A61F 2310/00023* (2013.01); *A61F 2310/00077* (2013.01); *A61L 2400/16* (2013.01); *A61L 2430/20* (2013.01)

(58) Field of Classification Search
USPC .................................................. 623/2.1–2.19
See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |

(56) References Cited

U.S. PATENT DOCUMENTS

| | | |
|---|---|---|
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,419,696 B1 | 7/2002 | Ortiz et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |

(56) References Cited

U.S. PATENT DOCUMENTS

| | | |
|---|---|---|
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 * | 5/2013 | Chau ............... A61F 2/2412 623/1.26 |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 * | 11/2016 | Vidlund ............... A61F 2/2409 |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 * | 11/2017 | Vidlund ............... A61F 2/2439 |
| 9,833,315 B2 * | 12/2017 | Vidlund ............... A61L 27/3629 |
| 9,867,700 B2 | 1/2018 | Bakis et al. |
| 9,895,221 B2 | 2/2018 | Vidlund |
| 9,986,993 B2 * | 6/2018 | Vidlund ............... A61F 2/2457 |
| 10,376,361 B2 * | 8/2019 | Gross ............... A61F 2/2439 |
| 10,588,742 B2 * | 3/2020 | Chau ............... A61F 2/2418 |
| 10,617,519 B2 | 4/2020 | Vidlund et al. |
| 10,639,145 B2 | 5/2020 | Vidlund et al. |
| 10,687,938 B2 * | 6/2020 | Patel ............... A61F 2/2412 |
| 10,758,345 B2 * | 9/2020 | Ratz ............... A61F 2/2418 |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |

(56) References Cited

U.S. PATENT DOCUMENTS

| | | |
|---|---|---|
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0225353 A1* | 11/2004 | McGuckin, Jr. ...... A61F 2/2436 623/2.11 |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1* | 8/2006 | Navia ...... A61F 2/2457 623/2.18 |
| 2006/0229708 A1 | 10/2006 | Powell et al. |
| 2006/0229719 A1 | 10/2006 | Marquez et al. |
| 2006/0235511 A1 | 10/2006 | Osborne |
| 2006/0241745 A1* | 10/2006 | Solem ...... A61F 2/2442 623/2.18 |
| 2006/0247491 A1 | 11/2006 | Vidlund et al. |
| 2006/0259135 A1 | 11/2006 | Navia et al. |
| 2006/0259136 A1* | 11/2006 | Nguyen ...... A61F 2/2415 623/2.18 |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077235 A1* | 3/2008 | Kirson ...... A61F 2/2466 623/2.11 |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1* | 7/2008 | Mesana ...... A61F 2/2433 623/1.11 |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |

(56) References Cited

U.S. PATENT DOCUMENTS

| | | |
|---|---|---|
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1* | 11/2009 | Rowe ............... A61F 2/2436 623/2.18 |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0145440 A1* | 6/2010 | Keranen ............. A61F 2/2448 623/2.37 |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0234937 A1 | 9/2010 | Wang et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0280606 A1* | 11/2010 | Naor ............... A61F 2/2448 623/2.18 |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0098802 A1* | 4/2011 | Braido ............... A61F 2/2442 623/1.26 |
| 2011/0112632 A1* | 5/2011 | Chau ............... A61F 2/2436 623/2.11 |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1* | 12/2011 | Schankereli ......... A61F 2/2418 623/2.11 |
| 2011/0319989 A1 | 12/2011 | Lane et al. |
| 2012/0010694 A1 | 1/2012 | Lutter et al. |
| 2012/0016464 A1* | 1/2012 | Seguin .............. A61F 2/2436 623/1.26 |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0165930 A1 | 6/2012 | Gifford, III et al. |
| 2012/0179244 A1* | 7/2012 | Schankereli ......... A61F 2/2418 623/2.11 |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1* | 11/2013 | Morriss ............. A61F 2/2445 623/2.12 |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2013/0338765 A1* | 12/2013 | Braido .............. A61F 2/2412 623/2.17 |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1* | 10/2014 | Tegels .............. A61F 2/2412 623/2.11 |
| 2014/0296970 A1 | 10/2014 | Ekvall et al. |

(56) References Cited

U.S. PATENT DOCUMENTS

| | | | |
|---|---|---|---|
| 2014/0296971 A1 | 10/2014 | Tegels et al. | |
| 2014/0296972 A1 | 10/2014 | Tegels et al. | |
| 2014/0296975 A1* | 10/2014 | Tegels | A61F 2/07 623/2.18 |
| 2014/0303718 A1 | 10/2014 | Tegels et al. | |
| 2014/0309732 A1 | 10/2014 | Solem | |
| 2014/0316516 A1 | 10/2014 | Vidlund et al. | |
| 2014/0324160 A1 | 10/2014 | Benichou et al. | |
| 2014/0324161 A1 | 10/2014 | Tegels et al. | |
| 2014/0324164 A1 | 10/2014 | Gross et al. | |
| 2014/0331475 A1 | 11/2014 | Duffy et al. | |
| 2014/0350663 A1* | 11/2014 | Braido | A61F 2/2412 623/2.1 |
| 2014/0358224 A1 | 12/2014 | Tegels et al. | |
| 2014/0364942 A1 | 12/2014 | Straubinger et al. | |
| 2014/0364944 A1 | 12/2014 | Lutter et al. | |
| 2014/0379076 A1 | 12/2014 | Vidlund et al. | |
| 2015/0005874 A1* | 1/2015 | Vidlund | A61F 2/2412 623/2.14 |
| 2015/0011821 A1 | 1/2015 | Gorman et al. | |
| 2015/0025553 A1 | 1/2015 | Del Nido et al. | |
| 2015/0057705 A1 | 2/2015 | Vidlund | |
| 2015/0073542 A1 | 3/2015 | Heldman | |
| 2015/0073545 A1* | 3/2015 | Braido | A61F 2/2412 623/2.18 |
| 2015/0094802 A1 | 4/2015 | Buchbinder et al. | |
| 2015/0105856 A1 | 4/2015 | Rowe et al. | |
| 2015/0119936 A1 | 4/2015 | Gilmore et al. | |
| 2015/0119978 A1 | 4/2015 | Tegels et al. | |
| 2015/0127093 A1 | 5/2015 | Hosmer et al. | |
| 2015/0127096 A1 | 5/2015 | Rowe et al. | |
| 2015/0134050 A1 | 5/2015 | Solem et al. | |
| 2015/0142100 A1 | 5/2015 | Morriss et al. | |
| 2015/0142101 A1 | 5/2015 | Coleman et al. | |
| 2015/0142103 A1* | 5/2015 | Vidlund | A61F 2/2439 623/2.17 |
| 2015/0142104 A1 | 5/2015 | Braido | |
| 2015/0173897 A1 | 6/2015 | Raanani et al. | |
| 2015/0196393 A1 | 7/2015 | Vidlund et al. | |
| 2015/0196688 A1* | 7/2015 | James | A61L 17/10 623/2.12 |
| 2015/0202044 A1 | 7/2015 | Chau et al. | |
| 2015/0216653 A1 | 8/2015 | Freudenthal | |
| 2015/0216660 A1* | 8/2015 | Pintor | A61F 2/2433 623/2.11 |
| 2015/0223820 A1* | 8/2015 | Olson | A61F 2/2418 623/2.11 |
| 2015/0223934 A1* | 8/2015 | Vidlund | A61F 2/2412 623/2.11 |
| 2015/0230921 A1 | 8/2015 | Chau et al. | |
| 2015/0238312 A1 | 8/2015 | Lashinski | |
| 2015/0238729 A1 | 8/2015 | Jenson et al. | |
| 2015/0272731 A1 | 10/2015 | Racchini et al. | |
| 2015/0305860 A1* | 10/2015 | Wang | A61L 27/20 623/2.17 |
| 2015/0305864 A1 | 10/2015 | Quadri et al. | |
| 2015/0305868 A1 | 10/2015 | Lutter et al. | |
| 2015/0327995 A1 | 11/2015 | Morin et al. | |
| 2015/0328001 A1* | 11/2015 | McLean | A61F 2/2427 623/2.36 |
| 2015/0335424 A1* | 11/2015 | McLean | A61F 2/2409 623/2.17 |
| 2015/0335429 A1 | 11/2015 | Morriss et al. | |
| 2015/0342717 A1 | 12/2015 | O'Donnell et al. | |
| 2015/0351903 A1 | 12/2015 | Morriss et al. | |
| 2015/0351906 A1 | 12/2015 | Hammer et al. | |
| 2016/0000562 A1 | 1/2016 | Siegel | |
| 2016/0008131 A1* | 1/2016 | Christianson | A61F 2/2457 623/2.11 |
| 2016/0067042 A1 | 3/2016 | Murad et al. | |
| 2016/0074160 A1 | 3/2016 | Christianson et al. | |
| 2016/0106537 A1* | 4/2016 | Christianson | A61F 2/2448 623/2.17 |
| 2016/0113764 A1* | 4/2016 | Sheahan | A61F 2/2418 623/2.17 |
| 2016/0143736 A1* | 5/2016 | Vidlund | A61B 17/0057 623/2.4 |
| 2016/0151155 A1 | 6/2016 | Lutter et al. | |
| 2016/0199177 A1* | 7/2016 | Spence | A61F 2/2418 623/2.38 |
| 2016/0206280 A1 | 7/2016 | Vidlund et al. | |
| 2016/0242902 A1* | 8/2016 | Morriss | A61F 2/2445 |
| 2016/0262879 A1 | 9/2016 | Meiri et al. | |
| 2016/0262881 A1 | 9/2016 | Schankereli et al. | |
| 2016/0278955 A1 | 9/2016 | Liu et al. | |
| 2016/0317290 A1* | 11/2016 | Chau | A61F 2/2466 |
| 2016/0324635 A1 | 11/2016 | Vidlund et al. | |
| 2016/0331527 A1 | 11/2016 | Vidlund et al. | |
| 2016/0346086 A1 | 12/2016 | Solem | |
| 2016/0367365 A1* | 12/2016 | Conklin | A61F 2/2418 |
| 2016/0367367 A1 | 12/2016 | Maisano et al. | |
| 2016/0367368 A1 | 12/2016 | Vidlund et al. | |
| 2017/0079790 A1 | 3/2017 | Vidlund et al. | |
| 2017/0100248 A1 | 4/2017 | Tegels et al. | |
| 2017/0128208 A1 | 5/2017 | Christianson et al. | |
| 2017/0181854 A1 | 6/2017 | Christianson et al. | |
| 2017/0196688 A1 | 7/2017 | Christianson et al. | |
| 2017/0252153 A1 | 9/2017 | Chau et al. | |
| 2017/0266001 A1 | 9/2017 | Vidlund et al. | |
| 2017/0281343 A1 | 10/2017 | Christianson et al. | |
| 2017/0312076 A1 | 11/2017 | Lutter et al. | |
| 2017/0312077 A1 | 11/2017 | Vidlund et al. | |
| 2017/0319333 A1 | 11/2017 | Tegels et al. | |
| 2018/0028314 A1 | 2/2018 | Ekvall et al. | |
| 2018/0078368 A1 | 3/2018 | Vidlund et al. | |
| 2018/0078370 A1 | 3/2018 | Kovalsky et al. | |
| 2019/0192295 A1* | 6/2019 | Spence | A61F 2/2436 |
| 2020/0030088 A1 | 1/2020 | Vidlund et al. | |
| 2020/0205970 A1* | 7/2020 | Chau | A61F 2/2418 |
| 2020/0261220 A1* | 8/2020 | Argento | A61F 2/2409 |
| 2020/0306034 A1* | 10/2020 | Patel | A61F 2/2418 |
| 2020/0345492 A1* | 11/2020 | Patel | A61F 2/2412 |
| 2021/0137678 A1* | 5/2021 | Spence | A61F 2/2436 |
| 2021/0154009 A1* | 5/2021 | Argento | A61F 2/2433 |

FOREIGN PATENT DOCUMENTS

| | | |
|---|---|---|
| CN | 1486161 A | 3/2004 |
| CN | 1961845 A | 5/2007 |
| CN | 2902226 Y | 5/2007 |
| CN | 101146484 A | 3/2008 |
| CN | 101180010 A | 5/2008 |
| CN | 101984938 A | 3/2011 |
| CN | 102639179 A | 8/2012 |
| CN | 102869317 A | 1/2013 |
| CN | 102869318 A | 1/2013 |
| CN | 102869321 A | 1/2013 |
| CN | 103220993 A | 7/2013 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 11/2005 |
| EP | 1849440 A1 | 10/2007 |
| EP | 2072027 A1 | 6/2009 |
| EP | 2111800 A1 | 10/2009 |
| EP | 2193762 A1 | 6/2010 |
| EP | 2278944 A2 | 2/2011 |
| EP | 2741711 A2 | 6/2014 |
| EP | 2747707 A1 | 7/2014 |
| EP | 2918248 A1 | 9/2015 |

(56) References Cited

FOREIGN PATENT DOCUMENTS

| | | |
|---|---|---|
| EP | 3403616 A1 | 11/2018 |
| FR | 2788217 A1 | 7/2000 |
| FR | 2815844 A1 | 5/2002 |
| JP | 2003505146 A | 2/2003 |
| JP | 2005515836 A | 6/2005 |
| JP | 2009508641 A | 3/2009 |
| JP | 2009514628 A | 4/2009 |
| JP | 2010508928 A | 3/2010 |
| JP | 2013512765 A | 4/2013 |
| NL | 1017275 C2 | 8/2002 |
| SU | 1271508 A1 | 11/1986 |
| WO | 9217118 A1 | 10/1992 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 200041652 A1 | 7/2000 |
| WO | 200047139 A1 | 8/2000 |
| WO | 0135878 A2 | 5/2001 |
| WO | 2001049213 A2 | 7/2001 |
| WO | 0154625 A1 | 8/2001 |
| WO | 2001054624 A1 | 8/2001 |
| WO | 2001056512 A1 | 8/2001 |
| WO | 2001061289 A1 | 8/2001 |
| WO | 200176510 A2 | 10/2001 |
| WO | 2001082840 A1 | 11/2001 |
| WO | 0203892 A1 | 1/2002 |
| WO | 2002004757 A1 | 1/2002 |
| WO | 2002022054 A1 | 3/2002 |
| WO | 2002028321 A2 | 4/2002 |
| WO | 0236048 A1 | 5/2002 |
| WO | 2002041789 A2 | 5/2002 |
| WO | 2002043620 A1 | 6/2002 |
| WO | 2002049540 A2 | 6/2002 |
| WO | 2002076348 A1 | 10/2002 |
| WO | 2003003943 A2 | 1/2003 |
| WO | 2003030776 A2 | 4/2003 |
| WO | 03047468 A1 | 6/2003 |
| WO | 2003049619 A2 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |
| WO | 2006064490 A1 | 6/2006 |
| WO | 2006070372 A2 | 7/2006 |
| WO | 2006113906 A1 | 10/2006 |
| WO | 2006127756 A2 | 11/2006 |
| WO | 2007081412 A1 | 7/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009079915 A1 | 7/2009 |
| WO | 2009080801 A1 | 7/2009 |
| WO | 2009132187 A1 | 10/2009 |
| WO | 2010008548 A2 | 1/2010 |
| WO | 2010037141 A1 | 4/2010 |
| WO | 2010057262 A1 | 5/2010 |
| WO | 2010090878 A2 | 8/2010 |
| WO | 2010098857 A1 | 9/2010 |
| WO | 2010098940 A2 | 9/2010 |
| WO | 2010121076 A2 | 10/2010 |
| WO | 2010151617 A2 | 12/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011111047 A2 | 9/2011 |
| WO | 2011159342 A1 | 12/2011 |
| WO | 2011163275 A2 | 12/2011 |
| WO | 2012011108 A2 | 1/2012 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013028387 A2 | 2/2013 |
| WO | 2013045262 A1 | 4/2013 |
| WO | 2013059747 A1 | 4/2013 |
| WO | 2013096411 A1 | 6/2013 |
| WO | 2013175468 A2 | 11/2013 |
| WO | 2014121280 A2 | 8/2014 |
| WO | 2014144937 A2 | 9/2014 |
| WO | 2014162306 A2 | 10/2014 |
| WO | 2014189974 A1 | 11/2014 |
| WO | 2015023862 A2 | 2/2015 |
| WO | 2015051430 A1 | 4/2015 |
| WO | 2015058039 A1 | 4/2015 |
| WO | 2015063580 A2 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

Rosch, J. et al., "The Birth, Eady Years and Future of Interventional Radiology," J Vasc Interv Radiol., Jul. 2003, 4:841-853.

Ross, D. N., "Aortic Valve Surgery," Guy's Hospital, London, 1968, pp. 192-197.

Rousseau, E. P. M. et al., "A Mechanical Analysis of the Closed Hancock Heart Valve Prosthesis," Journal of Biomechanics, 1998, 21(7):545-562.

Sabbah, A. N. et al., "Mechanical Factors in the Degeneration of Porcine Bioprosthetic Valves: An Overview," Dec. 1989, Journal of Cardiac Surgery, 4(4):302-309.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.

Supplementary European Search Report for European Application No. 12825480.2, dated Jul. 15, 2015, 8 pages.

Tofeig, M. et al., "Transcatheter Closure of a Mid-Muscular Ventricular Septal Defect with an Amplatzer VSD Occluder Device," Heart, 1999, 81:438-440.

Uchida, Barry T., et al., "Modifications of Gianturco Expandable Wire Stents," AJR:150, May 1988, Dec. 3, 1987, pp. 1185-1187.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.

Webb, J. G. et al., "Percutaneous Aortic Valve Implantation Retrograde from the Femoral Artery," Circulation, 2006, 113:842-850.

Wheatley, M.D., David J., "Valve Prostheses," Rob & Smith's Operative Surgery, Fourth Edition, pp. 415-424, ButtenNorths 1986.

Yoganathan, A. P. et al., "The Current Status of Prosthetic Heart Valves," In Polymetric Materials and Artificial Organs, Mar. 20, 1983, pp. 111-150, American Chemical Society.

Extended European Search Report with Written Opinion for Application No. 19214616.5 dated Aug. 12, 2020, 8 pages.

(56) References Cited

OTHER PUBLICATIONS

"Shape Memory Alloys," Retrieved from the Internet: <http://webdocs.cs.ualberta.ca/~database/MEMS/sma.html>, Feb. 5, 2016, 3 pages.
Al Zaibag, Muayed, et al., "Percutaneous Balloon Valvotomy in Tricuspid Stenos's," British Heart Journal, Jan. 1987, vol. 57, No. 1, pp. 51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration in Dilated Hearts," Interactive Cardiovascular and Thoracic Surgery, 2005, 4:475-477.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Examination Report No. 1 for Australian Application No. 2016203451, dated Jul. 13, 2018, 4 pages.
Extended Search Report for EP18167606 dated Aug. 29, 2018, pp. 1-3.
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.
Inoue, K. et al., "Clinical Application of Transvenous Mitral Commissurotomy by a New Balloon Catheter," The Journal of Thoracic and Cardiovascular Surgery, 1984, 87:394-402.
International Search Report and Written Opinion for International Application No. PCT/US2012/050579, dated Feb. 28, 2013, 9 pages.
Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, Georg, et al., Mitral valved stent implantation, European Journal of Cardio-Thoracic Surgery, 2010, vol. 38, pp. 350-355.
Ma, L. et al., "Double-crowned valved stents for off-pump mitral valve replacement," European Journal of Cardio-Thoracic Surgery, Aug. 2005, 28(2): 194-198.
Moazami, N. et al., "Transluminal aortic valve placement: A feasibility study with a newly designed collapsible aortic valve," ASAIO Journal, Sep./ Oct. 1996, 42(5):M381-M385.
Notice of Reasons for Rejection for Japanese Patent Application No. 2014-525197, dated Jul. 5, 2016, 8 pages.
Office Action for Australian Patent Application No. 2012299311, dated Mar. 2, 2015, 4 pages.
Office Action for Canadian Application No. 2,957,442, dated Feb. 27, 2018, 4 pages.
Office Action for Canadian Patent Application No. 2,844,746, dated Apr. 28, 2015, 3 pages.
Office Action for Canadian Patent Application No. 2,844,746, dated Aug. 10, 2016, 4 pages.
Office Action for Canadian Patent Application No. 2,844,746, dated May 1, 2017, 3 pages.
Office Action for European Application No. 12825480.2, dated Nov. 16, 2016, 7 pages.
Office Action for Japanese Application No. 2017-085324, dated Mar. 20, 2018, 3 pages.
Office Action for U.S. Appl. No. 14/237,023, dated May 9, 2016, 6 pages.
Office Action for U.S. Appl. No. 14/237,023, dated Nov. 30, 2015, 7 pages.
Office Action for U.S. Appl. No. 15/183,943, dated Feb. 1, 2017, 8 pages.
Office Action for U.S. Appl. No. 15/183,943, dated Sep. 1, 2016, 6 pages.
Orton, C., "Mitralseal: Hybrid Transcatheter Mitral Valve Replacement," Symposium: Small Animal Proceedings, 2011, pp. 311-312.
Pavcnik, D. et al. "Development and Initial Experimental Evaluation of a Prosthetic Aortic Valve for Transcatheter Placement," Radiology, 1992; 183:151-154.
Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196( 11 ): 173-174.
Rashkind, W. J., "Historical Aspects of Interventional Cardiology: Past, Present, Future," Texas Heart Institute Journal, Dec. 1986, 13(4):363-367.
Reul, H. et al., "The Geomety of the Aortic Root in Health, at Valve Disease and After Valve Replacement," J. Biomechanics, 1990, 23(2):181-191.
Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.
Preliminary Opinion of Opposition Decision for Application No. EP 12825480.2 dated Jan. 8, 2020, 9 pages.
Examination Report No. 1 for Australian Application No. 2019200617 dated Dec. 4, 2019.

(56) References Cited

OTHER PUBLICATIONS

Japanese Office Action for Application No. 2018227799 dated Feb. 12, 2020, 4 pages.
Examination Report No. 1 for Australian Application No. 2019246822, dated Nov. 27, 2019, 4 pages.
Office Action for Canadian Application No. 3,040,390 dated Apr. 29, 2020; 4 pages.

* cited by examiner

PGA

PLGA

P(LLA-CL)

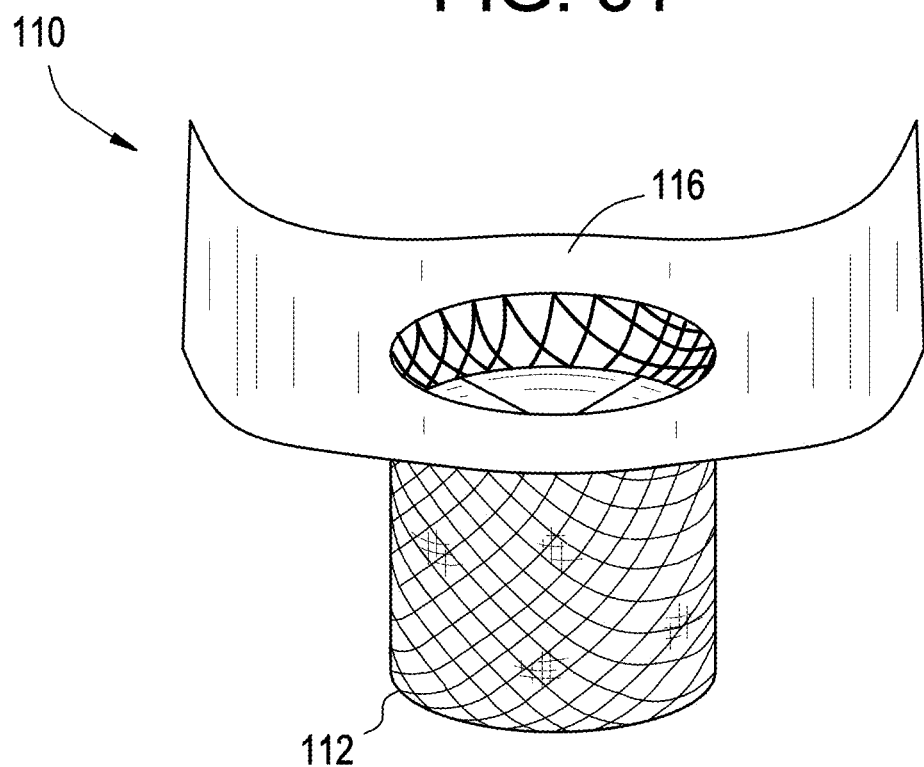

PROSTHETIC VALVES AND RELATED INVENTIONS

CROSS-REFERENCE TO RELATED APPLICATIONS

This application is a continuation of U.S. patent application Ser. No. 15/829,091, filed Dec. 1, 2017, which is a continuation of U.S. patent application Ser. No. 15/183,943, filed Jun. 16, 2016, now U.S. Pat. No. 9,833,315, issued Dec. 5, 2017, which is a divisional of U.S. patent application Ser. No. 14/237,023, filed Feb. 4, 2014, now U.S. Pat. No. 9,480,559, issued Nov. 1, 2016, which claims priority under 35 U.S.C. § 371 to, and is a U.S. national phase application of, International Application No. PCT/US2012/050579, filed Aug. 13, 2012, which claims priority to and the benefit of U.S. Provisional Application Ser. No. 61/522,542, filed Aug. 11, 2011; U.S. Provisional Application Ser. No. 61/522,468, filed Aug. 11, 2011; U.S. Provisional Application Ser. No. 61/522,450, filed Aug. 11, 2011; U.S. Provisional Application Ser. No. 61/522,476, filed Aug. 11, 2011; U.S. Provisional Application Ser. No. 61/523,134, filed Aug. 12, 2011; U.S. Provisional Application Ser. No. 61/564,462, filed Nov. 29, 2011; and U.S. Provisional Application Ser. No. 61/615,264, filed Mar. 24, 2012, the disclosures of which are incorporated herein by reference in their entireties.

BACKGROUND

Field of the Invention

This invention relates to various improvements for prosthetic valves, including but not limited to transcatheter mitral valve replacement prosthetics and delivery devices therefor.

Background of the Invention

The current state of knowledge is as follows.

Valvular heart disease and specifically aortic and mitral valve disease is a significant health issue in the US. Annually approximately 90,000 valve replacements are conducted in the US. Traditional valve replacement surgery, the orthotopic replacement of a heart valve, is an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients.

Thus, if the extra-corporeal component of the procedure could be eliminated, morbidities and the costs of valve replacement therapies would be significantly reduced.

While replacement of the aortic valve in a transcatheter manner has been the subject of intense investigation, lesser attention has been focused on the mitral valve. This is in part reflective of the greater level of complexity associated to the native mitral valve apparatus and thus a greater level of difficulty with regards to inserting and anchoring the replacement prosthesis.

Several designs for catheter-deployed (transcatheter) aortic valve replacement are under various stages of development. The Edwards SAPIEN transcatheter heart valve is currently undergoing clinical trial in patients with calcific aortic valve disease who are considered high-risk for conventional open-heart valve surgery. This valve is deployable via a retrograde transarterial (transfemoral) approach or an antegrade transapical (transventricular) approach. A key aspect of the Edwards SAPIEN and other transcatheter aortic valve replacement designs is their dependence on lateral fixation (e.g. tines) that engages the valve tissues as the primary anchoring mechanism. Such a design basically relies on circumferential friction around the valve housing or stent to prevent dislodgement during the cardiac cycle. This anchoring mechanism is facilitated by, and may somewhat depend on, a calcified aortic valve annulus. This design also requires that the valve housing or stent have a certain degree of rigidity.

At least one transcatheter mitral valve design is currently in development. The Endovalve uses a folding tripod-like design that delivers a tri-leaflet bioprosthetic valve. It is designed to be deployed from a minimally invasive transatrial approach, and could eventually be adapted to a transvenous atrial septotomy delivery. This design uses "proprietary gripping features" designed to engage the valve annulus and leaflets tissues. Thus the anchoring mechanism of this device is essentially equivalent to that used by transcatheter aortic valve replacement designs.

One problem involves the repetitive deformation of the nitinol wire material commonly used in the manufacture of stented valves. Fatigue fractures of the metal wire material can result in a catastrophic structural failure whereby the valve support structure weakens and breaks. Although failure of a single wire may not necessarily cause a structural collapse of the entire valve, over time, this possibility becomes a practical reality. When the consequence of valve failure means the death of the patient, the importance cannot be overstated.

Various problems continue to exist in this field, including problems with perivalvular leaking around installed prosthetic valve, lack of a good fit and stability for the prosthetic valve within the native mitral annulus, atrial tissue erosion, excess wear on the metallic structures, interference with the aorta at the posterior side of the mitral annulus, difficulties in deployment and retrieval, and lack of customization, to name a few. Accordingly, there exists a need for the improvement inventions disclosed herein.

BRIEF SUMMARY OF THE INVENTION

The present invention relates to improvements for prosthetic valves intended to be deployed into a closed beating heart using a transcatheter delivery system. The invention provides improved stability, in-growth of the prosthetic, maintains structural integrity over large cycles, addresses biocompatibility issues, addresses commissural regurgitation, and addresses hemocompatibility issues. Additionally, the invention addresses problems related to unwanted buckling of the material, lack of sealing of the prosthetic valve within the valvular annulus, unwanted twisting of fabrics, and difficulties arising from elasticity during attachment of the cover to the stent.

Improved Surfaces

In a preferred embodiment, there is provided a multi-layer cover for a prosthetic heart valve having an expandable tubular stent and an expandable internal leaflet assembly, wherein said stent is a tubular wire-form having an interior wall and an exterior wall, and wherein said leaflet assembly is disposed within the stent to form a valve and is comprised of stabilized tissue or synthetic material, wherein the multi-layer cover comprises at least two layers of stabilized tissue or synthetic material, a first layer comprised of a polyester material and a second layer comprised of a polyester material or stabilized tissue, wherein the first layer is attached to the interior wall of the stent and the second layer is attached to the exterior wall of the stent.

In another preferred embodiment, there is provided wherein the stabilized tissue is derived from 30 day old bovine, ovine, equine or porcine pericardium, or from animal small intestine submucosa.

In another preferred embodiment, there is provided wherein the synthetic material is selected from the group consisting of polyester, polyurethane, and polytetrafluoroethylene.

In another preferred embodiment, there is provided wherein the first layer and the second layer range in thickness from about 0.001" (0.0254 mm) to about 0.015" (0.3809 mm), or more alternatively from about 0.002" (0.0508 mm) to about 0.010" (0.254 mm), or alternatively wherein the first layer and the second layer are about 0.005" (0.127 mm) in thickness.

In another preferred embodiment, there is provided wherein the stabilized tissue or synthetic material is treated with anticoagulant.

In another preferred embodiment, there is provided wherein the stabilized tissue or synthetic material is heparinized.

In another preferred embodiment, there is provided wherein the first layer and the second layer are both synthetic material.

In another preferred embodiment, there is provided wherein the synthetic material is selected from the group consisting of polyester, polyurethane, and polytetrafluoroethylene.

In another preferred embodiment, there is provided wherein the synthetic material is electrospun.

In another preferred embodiment, there is provided wherein the stent tubular wire-form is formed as a unitary shape comprising a tubular body portion having an open gasket-like sealing cuff at one end, and wherein the tubular body portion and the sealing cuff are formed from the same piece of superelastic metal, and wherein the first layer and the second layer extend to cover substantially all of the stent.

In another preferred embodiment, there is provided wherein the superelastic metal is a nickel-titanium alloy.

In another preferred embodiment, there is provided a prosthetic valve having the multi-layer cover described and/or claimed herein.

In another preferred embodiment, there is provided a method of treating mitral regurgitation in a patient, which comprises the step of surgically deploying the prosthetic heart valve provided herein into the mitral annulus of the patient.

In another preferred embodiment, there is provided a method of treating tricuspid regurgitation in a patient, which comprises the step of surgically deploying the prosthetic heart valve provided herein into the tricuspid annulus of the patient.

Shuttlecock Annular Valve

In another embodiment, there is provided a prosthetic pericardial valve supported by a self expanding nitinol body that uses tethers for anchoring to the ventricular myocardium.

In another preferred embodiment, there is provided a prosthetic pericardial valve which comprises an expandable tubular stent having an annular collar and an internal leaflet assembly, wherein the stent is covered on an exterior surface with stabilized tissue, synthetic fabric material, or a combination of both, and the internal leaflet assembly is disposed with the lumen of the stent and is comprised of stabilized tissue, synthetic fabric material, or a combination of both, wherein the annular collar is a web of polyester or polyeester-like fabric or metal mesh spanning from a distal end of the stent body to a collar support structure made from superelastic metal, the collar forming a flat circular band connected on one edge to the stent and extending circumferentially around the exterior of the stent at or near a distal end of the stent.

In another preferred embodiment, there is provided a prosthetic pericardial valve, wherein the internal leaflet assembly is saddle-shaped.

In another preferred embodiment, there is provided a prosthetic pericardial valve wherein the stent covering is stabilized tissue.

In another preferred embodiment, there is provided a prosthetic pericardial valve wherein the leaflet assembly is comprised of stabilized tissue.

In another preferred embodiment, there is provided a prosthetic pericardial valve wherein the prosthetic pericardial valve is elastic and is compressed into a delivery catheter for deployment within a patient, and whereby upon expelling the prosthetic pericardial valve from the delivery catheter, the valve expands to its functional shape.

In another preferred embodiment, there is provided a prosthetic pericardial valve wherein the stent and collar support structure are formed from the same piece of superelastic metal.

In another preferred embodiment, there is provided a prosthetic pericardial valve wherein the superelastic metal is a nickel-titanium alloy.

In another preferred embodiment, there is provided a prosthetic pericardial valve wherein the stent and collar are laser cut with pre-determined shapes to facilitate collapsing into a catheter delivery system.

In another preferred embodiment, there is provided a prosthetic pericardial valve wherein the stent is constructed from ductile metal that requires a balloon for expansion once the valve is positioned at the valve annulus.

In another preferred embodiment, there is provided a prosthetic pericardial valve wherein the stabilized tissue is derived from 30 day old bovine, ovine, equine or porcine pericardium, or from animal small intestine submucosa.

In another preferred embodiment, there is provided a prosthetic pericardial valve wherein the synthetic material is selected from the group consisting of polyester, polyurethane, and polytetrafluoroethylene.

In another preferred embodiment, there is provided a prosthetic pericardial valve wherein the stabilized tissue or synthetic material is treated with anticoagulant.

In another preferred embodiment, there is provided a prosthetic pericardial valve wherein the stabilized tissue or synthetic material is heparinized.

In another preferred embodiment, there is provided a prosthetic pericardial valve wherein the angle of the collar to the stent comprises a range of between about 5 and about 45 degrees.

In another preferred embodiment, there is provided a prosthetic pericardial valve wherein the collar support structure extends laterally beyond the wall of the expanded tubular stent between about 2 and about 10 millimeters.

In another preferred embodiment, there is provided a prosthetic pericardial valve wherein the tubular stent has a plurality of tether attachment structures.

In another preferred embodiment, there is provided a prosthetic pericardial valve further comprising a plurality of tethers attached to the prosthetic pericardial valve for anchoring the prosthetic pericardial valve to tissue.

In another preferred embodiment, there is provided a prosthetic pericardial valve wherein at least one of the plurality of tethers is an elastic tether.

In another preferred embodiment, there is provided a prosthetic pericardial valve wherein at least one of the plurality of tethers is a bioresorbable tether.

In another preferred embodiment, there is provided a prosthetic pericardial valve wherein at least one of the plurality of tethers is a positioning tether and at least one of the plurality of tethers is an anchoring tether.

In another preferred embodiment, there is provided a prosthetic pericardial valve further comprising at least one tether attached to the collar support structure and at least one tether attached to the stent body.

In another preferred embodiment, there is provided a prosthetic pericardial valve further comprising a plurality of tethers attached to the prosthetic pericardial valve wherein one of the plurality of tethers is attached to an epicardial tether securing device.

In another preferred embodiment, there is provided a prosthetic pericardial valve wherein the leaflet assembly is constructed solely of stabilized tissue or synthetic material without a separate wire support structure, wherein the leaflet assembly comprises a plurality of valve leaflets attached to a leaflet housing, wherein the leaflet assembly is disposed within the lumen of the stent and is attached to the stent to provide a sealed joint between the leaflet assembly and the inner wall of the stent.

In another preferred embodiment, there is provided wherein the valve has a three-dimensional structure that is a D-shape in lateral cross-section.

In another preferred embodiment, there is provided wherein the valve has a three-dimensional structure that is a kidney-shape in lateral cross-section.

In another preferred embodiment, there is provided a method of treating mitral regurgitation in a patient, which comprises the step of surgically deploying the prosthetic pericardial valve disclosed and claimed herein into the mitral annulus of the patient.

In another preferred embodiment, there is provided a method wherein the prosthetic pericardial valve is deployed by directly accessing the pericardial through the intercostal space, using an apical approach to enter the left ventricle, and deploying the prosthetic pericardial valve into the mitral annulus.

In another preferred embodiment, there is provided a method wherein the prosthetic pericardial valve is deployed by directly accessing the pericardial through a thoracotomy, sternotomy, or minimally-invasive thoracic, thoracoscopic, or trans-diaphragmatic approach to enter the left ventricle.

In another preferred embodiment, there is provided a method wherein the prosthetic pericardial valve is deployed by directly accessing the pericardial through the intercostal space, using an approach through the lateral ventricular wall to enter the left ventricle.

In another preferred embodiment, there is provided a method wherein the prosthetic pericardial valve is deployed by accessing the left atrium of the pericardial using a transvenous atrial septostomy approach.

In another preferred embodiment, there is provided a method wherein the prosthetic pericardial valve is deployed by accessing the left ventricle of the pericardial using a transarterial retrograde aortic valve approach.

In another preferred embodiment, there is provided a method wherein the prosthetic pericardial valve is deployed by accessing the left ventricle of the pericardial using a transvenous ventricular septostomy approach.

In another preferred embodiment, there is provided a method further comprising tethering the prosthetic pericardial valve to tissue within the left ventricle.

In another preferred embodiment, there is provided a method wherein the prosthetic pericardial valve is tethered to the apex of the left ventricle using an epicardial tether securing device.

In another preferred embodiment, there is provided a method wherein the tissue is selected from papillary muscle tissue, septal tissue, or ventricular wall tissue.

In another preferred embodiment, there is provided a method wherein the prosthetic pericardial valve is tethered to the apex of the ventricular septum.

In another preferred embodiment, there is provided a method of treating tricuspid regurgitation in a patient, which comprises the step of surgically deploying the prosthetic pericardial valve as disclosed and claimed herein into the tricuspid annulus of the patient.

In another preferred embodiment, there is provided a method wherein the prosthetic pericardial valve is deployed by directly accessing the pericardial through the intercostal space, using an apical approach to enter the right ventricle, or wherein the prosthetic pericardial valve is deployed by directly accessing the pericardial through a thoracotomy, sternotomy, or minimally-invasive thoracic, thoracoscopic, or trans-diaphragmatic approach to enter the right ventricle, or wherein the prosthetic pericardial valve is deployed by directly accessing the pericardial through the intercostal space, using an approach through the lateral ventricular wall to enter the right ventricle, or wherein the prosthetic pericardial valve is deployed by accessing the right atrium of the pericardial using a transvenous approach.

In another preferred embodiment, there is provided a method further comprising tethering the prosthetic pericardial valve to tissue within the right ventricle.

In another preferred embodiment, there is provided a method wherein the prosthetic pericardial valve is tethered to the apex of the right ventricle using an epicardial tether securing device.

In another preferred embodiment, there is provided a method wherein the tissue is selected from papillary muscle tissue, septal tissue, or ventricular wall tissue.

Spring Anchor

In one embodiment, spring-shaped anchor comprising at least two coils, with shape-memory characteristics fashioned for attachment to a prosthetic pericardial valve stent and circumnavigation of the chordae tendineae.

In a preferred embodiment, wherein the anchor is fabricated from one or more of a group of shape-memory, surgical-grade alloys, including, without limitation, nickel-titanium, copper-zinc-nickel, or copper-aluminium-nickel.

In another preferred embodiment, wherein the anchor is fabricated from one or more of a group of shape-memory polymers or ceramics, including, without limitation, polyurethanes with ionic or mesogenic components made by a prepolymer method, a block copolymer of polyethylene terephthalate (PET) and polyethyleneoxide (PEO), block copolymers containing polystyrene and poly(1,4-butadiene), an ABA triblock copolymer made from poly (2-methyl-2-oxazoline) and polytetrahydrofuran, and the ceramic Mn-doped (Pb, Sr)TiO3.

In another preferred embodiment, wherein the shape-memory material forming the anchor has been drawn or formed into a wire or band.

In another preferred embodiment, wherein the wire is 0.012" nickel-titanium wire.

In another preferred embodiment, wherein the wire or band, upon deployment, is formed to open into spring-like shape with an open tip.

In another preferred embodiment, wherein the proximal loop of the spring anchor is fused to the base of the stent component of the associated prosthetic pericardial valve via welding, soldering or by use of an adhesive.

In another preferred embodiment, wherein the adhesive used to bond the proximal loop of the spring anchor to the base of the stent is chosen from one or more of the following group, without limitation: synthetic polymer glues including, without limitation, epoxy resins, epoxy putty, ethylene-vinyl acetate, phenol formaldehyde resins, polyamides, polyester resins, polypropylene, polysulfides, polyurethane, polyvinyl acetate, polyvinyl alcohol, polyvinyl chloride, polyvinylpyrrolidone, silicones and styrene acrylic copolymer; synthetic monomer glues such as acrylnitrile, cyanoacrylate, acrylic and resorcinol glue; and solvent-type glues such as polystyrene cement/butanone and dichloromethane.

In another preferred embodiment, wherein the loops of the coil equal or exceed the circumference of the base of the stent.

In another preferred embodiment, wherein all loops of the spring anchor are of equal circumference.

In another preferred embodiment, wherein the proximal loop of the spring anchor is equal in circumference to the base of the prosthetic valve stent, further wherein each successive loop gradually increases in circumference.

In another preferred embodiment, further comprising wherein the fused proximal loop of the spring anchor and base of the prosthetic valve stent are attached to a plurality of tethers for anchoring the prosthetic pericardial valve to tissue.

In another preferred embodiment, wherein the anchor is laser cut with pre-determined shapes to facilitate collapsing into a catheter delivery system.

In another preferred embodiment, wherein the anchor is covered with biocompatible stabilized tissue or synthetic material.

In another preferred embodiment, wherein the stabilized covering tissue is derived from 30 day old bovine, ovine, equine or porcine pericardium, or from animal small intestine submucosa.

In another preferred embodiment, wherein the synthetic covering material is selected from the group consisting of polyester, polyurethane, and polytetrafluoroethylene.

In another preferred embodiment, wherein the stabilized tissue or synthetic covering material is treated with anticoagulant.

In another preferred embodiment, wherein the stabilized tissue or synthetic covering material is heparinized.

A method of treating mitral regurgitation in a patient, which comprises the step of surgically deploying a prosthetic pericardial valve into the mitral annulus of the patient while simultaneously deploying the spring anchor of claim 1 around the corresponding chordae tendineae.

In another preferred embodiment, the method wherein the prosthetic pericardial valve and attached spring anchor are deployed by directly accessing the heart through the intercostal space, using an apical approach to enter the left ventricle, and deploying the prosthetic pericardial valve into the mitral annulus and the spring anchor around the chordae tendineae.

In another preferred embodiment, the method wherein the prosthetic pericardial valve and attached spring anchor are deployed by directly accessing the heart through a thoracotomy, sternotomy, or minimally-invasive thoracic, thorascopic, or trans-diaphragmatic approach to enter the left ventricle.

In another preferred embodiment, the method wherein the prosthetic pericardial valve and attached spring anchor are deployed by directly accessing the heart through the intercostal space, using an approach through the lateral ventricular wall to enter the left ventricle.

In another preferred embodiment, the method wherein the prosthetic pericardial valve and attached spring anchor are deployed by accessing the left atrium of the pericardial using a transvenous atrial septostomy approach.

In another preferred embodiment, the method wherein the prosthetic pericardial valve and attached spring anchor are deployed by accessing the left ventricle of the pericardial using a transarterial retrograde aortic valve approach.

In another preferred embodiment, the method wherein the prosthetic pericardial valve and attached spring anchor are deployed by accessing the left ventricle of the pericardial using a transvenous ventricular septostomy approach.

In another preferred embodiment, the method further comprising wherein the spring anchor is secured around the chordae tendineae by guiding the anchor in a rotating motion using known transcatheter surgical tools.

In another preferred embodiment, the method further comprising wherein the spring anchor is secured around the chordae tendineae by pulling the chordae tendineae within the circumference of one or more coil loops using known transcatheter surgical tools.

In another preferred embodiment, the method wherein the prosthetic pericardial valve is tethered to one or more of the pericardial tissue areas, including without limitation, the apex of the left ventricle, the papillary muscle tissue, the septal tissue, ventricular wall tissue, apex of the ventricular septum, using an epicardial tether securing device.

A method of treating tricuspid regurgitation in a patient, which comprises the step of surgically deploying a prosthetic pericardial valve into the tricuspid annulus of the patient while simultaneously deploying the spring anchor of claim 1 around the corresponding chordae tendineae.

In another preferred embodiment, the method wherein the prosthetic pericardial valve and attached spring anchor are deployed by directly accessing the pericardial through the intercostal space, using an apical approach to enter the right ventricle.

In another preferred embodiment, the method wherein the prosthetic pericardial valve and attached spring anchor are deployed by directly accessing the pericardial through a thoracotomy, sternotomy, or minimally-invasive thoracic, thorascopic, or trans-diaphragmatic approach to enter the right ventricle.

In another preferred embodiment, the method wherein the prosthetic pericardial valve and attached spring anchor are deployed by directly accessing the pericardial through the intercostal space, using an approach through the lateral ventricular wall to enter the right ventricle.

In another preferred embodiment, the method wherein the prosthetic pericardial valve and attached spring anchor are deployed by accessing the right atrium of the pericardial using a transvenous approach.

In another preferred embodiment, the method further comprising wherein the spring anchor is secured around the chordae tendineae by guiding the anchor in a rotating motion using known transcatheter surgical tools.

In another preferred embodiment, the method further comprising wherein the spring anchor is secured around the chordae tendineae by pulling the chordae tendineae within the circumference of one or more coil loops using known transcatheter surgical tools.

In another preferred embodiment, the method further comprising tethering the prosthetic pericardial valve to tissue within the right ventricle.

In another preferred embodiment, the method wherein the prosthetic pericardial valve is tethered to the apex of the right ventricle using an epicardial tether securing device.

In another preferred embodiment, the method wherein the tissue is selected from papillary muscle tissue, septal tissue, or ventricular wall tissue.

Annular Clamps

In one embodiment, a prosthetic valve clamp, comprising: (a) a hinge made of a pin, optionally surrounded by a spring, said pin extending through holes in two interdigitated middle members, which hinge can be manipulated into a closed or open position; (b) wherein each middle member comprises (i) a footer section with a proximal side and a distal side, (ii) two flat plates wherein the distal end of each plate is attached to the narrow edges of the proximal side of the footer section and extend therefrom, in parallel, at adjustable angles, (iii) wherein the proximal end of each such plate contains a centered circular hole of a diameter to accommodate the insertion of the pin, and (iv) wherein a flat flange protrudes from the center of the inner end of the footer section, such flange containing a centered hole to allow a pressure-bearing member to attach to open and close the hinge; (c) two or more semicircular fingers, with an equal number of such fingers attached to the distal end of each middle member such that, upon closing of the hinge, the open side of the semicircle faces inward and the closed side faces outward, wherein the fingers or dual sets of fingers move towards one another as the hinge closes and away from one another as the hinge opens; (d) wherein the semicircular fingers are attached to the middle member in a staggered fashion such that the semicircular members interdigitate upon closing; and (e) wherein the tip of each semicircular finger tapers to form a point capable of piercing valve annulus tissue.

In another preferred embodiment, a prosthetic valve clamp, comprising: (a) a hinge made of a pin, optionally surrounded by a spring, said pin extending through holes in the proximal ends of each of two or more closing members, which hinge can be manipulated into a closed or open position; (b) two or more closing members, each with a straight base branching outward into a semicircular shape such that, upon closing of the hinge, the open side of the semicircle faces inward and the closed side faces outward, wherein each closing member, or set of two or more closing members, move parallel to one another in opposite directions, towards one another as the hinge closes and away from one another as the hinge opens; (c) further comprising wherein the closing members are attached to the pin in a staggered fashion such that the semicircular members interdigitate upon closing; and (d) further comprising wherein the tip of each closing member tapers to form a point capable of piercing valve annulus tissue.

In another preferred embodiment, a system for anchoring a prosthetic mitral valve stent comprising: (a) a braided or laser-cut stent; (b) an assembly for a suction fin further comprising a tube located within the artificial stent annulus and circumnavigating said annulus, emanating from the inner surface of the artificial stent annulus; (c) an assembly for a glue fin further comprising a tube located within the artificial stent annulus and circumnavigating said annulus, emanating from the inner surface of the artificial stent annulus; (d) a connection between each of the glue fin assembly and the suction fin assembly and the transapical delivery catheter; (e) a series of clamping devices dispersed at intervals around the exterior surface of the artificial stent annulus, each clamping onto a security belt and opening upon the removal of such belt; (f) a plurality of wires, with each attached to the posterior side of a clamping device such that a pull on the wire will close the clamping device; and (g) a guidance catheter wherein the wires of step (f) are contained within the catheter lumen that comprises a plurality of holes circumnavigating the catheter, with one or more wires emanating from each such hole.

In another preferred embodiment, one of the above prosthetic valve anchoring devices, further comprising wherein the device is comprised of one or more types of medically acceptable metallic alloys, natural or synthetic polymers or ceramics, including but not limited to shape-memory alloys.

In another preferred embodiment, one of the above prosthetic valve anchoring devices, further comprising wherein the tapered tips of the elements comprise further anchoring features, including but not limited to fishhook or arrowhead designs, with or without retraction capabilities for ease in withdrawing the anchors from tissue.

Improved Cuff/Collar Variations

In one embodiment, an improved design and function of a compressible prosthetic heart valve replacement having an improved contoured atrial cuff/collar which can be deployed into a closed beating heart using a transcatheter delivery system. The design as discussed focuses on the deployment of a device via a minimally invasive fashion and by way of example considers a minimally invasive surgical procedure utilizing the intercostal or subxyphoid space for valve introduction. In order to accomplish this, the valve is formed in such a manner that it can be compressed to fit within a delivery system and secondarily ejected from the delivery system into the target location, for example the mitral or tricuspid valve annulus.

In a preferred embodiment, there is provided a prosthetic mitral valve containing a atrial cuff/collar which locally contours to the mitral annulus.

In another preferred embodiment, there is provided a method of sealing a deployed prosthetic mitral valve against hemodynamic leaking, comprising fitting a prosthetic mitral valve with an atrial cuff/collar prior to deployment wherein the atrial cuff/collar is constructed to contour to the commissures of a pathologically defective mitral valve and constructed to contour to the zone of coaptation of the pathologically defective mitral valve, wherein the atrial cuff/collar is formed from wire originating from one end of an expandable tubular braided wire stent and the atrial cuff/collar is covered with stabilized tissue or synthetic material, the commissural contour components of the atrial cuff/collar and the zone of coaptation contour components of the atrial cuff/collar forming a complete or partial saddle-shape wherein the commissural contour components are in direct communication with the mitral valve commissures, and the zone of coaptation contour components are in direct communication with the mitral valve zone of coaptation.

In a preferred embodiment, the atrial cuff/collar shape is agaricoid.

In another preferred embodiment, the atrial cuff/collar shape is onychoid.

In another preferred embodiment, the atrial cuff/collar shape is reniform.

In another preferred embodiment, the atrial cuff/collar shape is an oval.

In another preferred embodiment, the atrial cuff/collar shape is a truncated-oval having a squared end.

In another preferred embodiment, the atrial cuff/collar shape is propeller-shaped having two or three blades.

In another preferred embodiment, the atrial cuff/collar shape is cruciform.

In another preferred embodiment, the atrial cuff/collar shape is petal-shaped having flat radial covered loops.

In another preferred embodiment, the atrial cuff/collar shape is irregular or amoeboid.

In another preferred embodiment, the atrial cuff/collar shape is cotyloid shaped.

In another preferred embodiment, the atrial cuff/collar shape is a partial half-round fan-shape.

In another preferred embodiment, the atrial cuff/collar shape is a rectangular U-shape.

In another preferred embodiment, the atrial cuff/collar is constructed from ductile metal.

In another preferred embodiment, the atrial cuff/collar shape is constructed with a cover of stabilized tissue that is derived from adult, or 90-day old, or 30 day old bovine, ovine, equine or porcine pericardium, or from animal small intestine submucosa.

In another preferred embodiment, the atrial cuff/collar shape is constructed with a cover of synthetic material is selected from the group consisting of polyester, polyurethane, and polytetrafluoroethylene.

In another preferred embodiment, the stabilized tissue or synthetic material is treated with anticoagulant.

In another preferred embodiment, the method further comprises the step of anchoring the prosthetic heart valve to tissue uses a plurality of tethers to the atrial cuff/collar.

In another preferred embodiment, at least one of the plurality of tethers is an elastic tether.

In another preferred embodiment, at least one of the plurality of tethers is a bioresorbable tether.

Improved Stent Designs

An embodiment relating to the design and function of a pre-configured compressible transcatheter prosthetic heart valve replacement having improved stent structure-function profiles which can be deployed into a closed beating heart using a transcatheter delivery system. The design as discussed focuses on the deployment of a device via a minimally invasive fashion and by way of example considers a minimally invasive surgical procedure utilizing the intercostal or subxyphoid space for valve introduction. In order to accomplish this, the valve is formed in such a manner that it can be compressed to fit within a delivery system and secondarily ejected from the delivery system into the target location, for example the mitral or tricuspid valve annulus.

In a preferred embodiment, there is provided a prosthetic mitral valve containing an improved stent which locally contours to the mitral structures and/or annulus.

In another preferred embodiment, there is provided a prosthetic heart valve with a stent body that has a low height to width profile.

In a preferred embodiment, the prosthetic mitral valve contains an improved stent body that is a half-round D-shape in cross-section.

In a preferred embodiment, the prosthetic mitral valve contains an improved stent body that is a bent tubular stent structure wherein the bend is directed away from the anterior leaflet, away from interfering with coaptation of adjacent, e.g. aortic, valvular leaflets.

In a preferred embodiment, the prosthetic mitral valve contains an improved stent body that has a low height to width profile and the leaflet structure disposed within the stent is positioned at or near the atrial end of the stent body.

In another preferred embodiment, the a prosthetic mitral valve has a stent body made from both braided wire (atrial end) and laser-cut metal (annular or ventricular end), or vice versa.

In a preferred embodiment, the prosthetic heart valve has a cuff that has articulating wire loops of various lengths.

In another preferred embodiment, the prosthetic heart valve has at least one elastic tether to provide compliance during the physiologic movement or conformational changes associated with heart contraction.

In another preferred embodiment, the prosthetic heart valve has a stent body and cuff that are made from a superelastic metal.

In another preferred embodiment, the prosthetic heart valve has a tether which is used to position the valve cuff into the mitral annulus to prevent perivalvular leak.

In another preferred embodiment, the tethers are bioabsorbable and provide temporary anchoring until biological fixation of the prosthesis occurs. Biological fixation consisting of fibrous adhesions between the leaflet tissues and prosthesis or compression on the prosthesis by reversal of heart dilation, or both.

In another preferred embodiment, the prosthetic heart valve has a cuff for a prosthetic heart valve, said cuff being covered with tissue.

In another preferred embodiment, the cuff is covered with a synthetic polymer selected from expandable polytetrafluoroethylene (ePTFE) or polyester.

In another preferred embodiment, there is provided a prosthetic heart valve that has leaflet material constructed from a material selected from the group consisting of polyurethane, polytetrafluoroethylene, pericardium, and small intestine submucosa.

In another preferred embodiment, there is provided a prosthetic heart valve having surfaces that are treated with anticoagulant.

In another preferred embodiment, there is provided a prosthetic heart valve having a cuff and containing anchoring tethers which are attached to the cuff.

In another preferred embodiment, there is provided a prosthetic heart valve having a cuff and containing anchoring tethers which are attached to the cuff and at both commissural tips.

In another preferred embodiment, there is provided a prosthetic heart valve having a cuff where the cuff attachment relative to the body is within the angles of about 60 degrees to about 150 degrees.

In another preferred embodiment, there is provided a prosthetic heart valve containing a combination of tethers and barbs useful for anchoring the device into the mitral annulus.

In another embodiment, the wire of the cuff is formed as a series of radially extending loops of equal or variable length.

In another embodiment, the cuff extends laterally beyond the expanded tubular stent according to a ratio of the relationship between the height of the expanded deployed stent (h) and the lateral distance that the cuff extends onto the tissue (1). Preferably, the h/l ratio can range from 1:10 to 10:1, and more preferably includes without limitation 1:3, 1:2, 1:1, 2:1, and fractional ranges there between such as 1.25:2.0, 1.5:2.0, and so forth. It is contemplated in one non-limiting example that the cuff can extend laterally (1) between about 3 and about 30 millimeters.

In another embodiment, there is provided a feature wherein the tubular stent has a first end and a second end, wherein the cuff is formed from the stent itself, or in the alternative is formed separately and wherein the cuff is located at the first end of the stent, and the second end of the tubular stent has a plurality of tether attachment structures.

In another embodiment, there is provided a feature further comprising a plurality of tethers for anchoring the prosthetic heart valve to tissue and/or for positioning the prosthetic heart valve.

In another embodiment, there is provided a feature further comprising an epicardial tether securing device, wherein the tethers extend from about 2 cm to about 20 cm in length, and are fastened to an epicardial tether securing device. Some pathological conditions within a ventricle may require a atrial-apical tether from about 8 to about 15 cm, or more as described within the range above.

In another embodiment, there is provided a catheter delivery system for delivery of a prosthetic heart valve which comprises a delivery catheter having the prosthetic heart valve disposed therein, and an obturator for expelling the prosthetic heart valve.

In another embodiment, there is provided an assembly kit for preparing the catheter delivery system which comprises a compression funnel, an introducer, a wire snare, an obturator, a delivery catheter, and a prosthetic heart valve, wherein the compression funnel has an aperture for attaching to the introducer, wherein said introducer is comprised of a tube having a diameter that fits within the diameter of the delivery catheter, wherein said obturator is comprised of a tube fitted with a handle at one end and a cap at the other end, wherein said cap has an opening to allow the wire snare to travel therethrough, and said obturator has a diameter that fits within the diameter of the introducer, and wherein said prosthetic heart valve is compressible and fits within the delivery catheter.

In another embodiment, there is provided a method of treating mitral regurgitation and/or tricuspid regurgitation in a patient, which comprises the step of surgically deploying the prosthetic heart valve described herein into the annulus of the target valve structure, e.g. mitral valve annulus and tricuspid valve annulus of the patient.

In another embodiment, there is provided a feature wherein the prosthetic heart valve is deployed by directly accessing the heart through an intercostal space, using an apical approach to enter the left (or right) ventricle, and deploying the prosthetic heart valve into the valvular annulus using the catheter delivery system.

In another embodiment, there is provided a feature wherein the prosthetic heart valve is deployed by directly accessing the heart through a thoracotomy, sternotomy, or minimally-invasive thoracic, thorascopic, or transdiaphragmatic approach to enter the left (or right) ventricle, and deploying the prosthetic heart valve into the valvular annulus using the catheter delivery system.

In another embodiment, there is provided a feature wherein the prosthetic heart valve is deployed by directly accessing the heart through the intercostal space, using a lateral approach to enter the left or right ventricle, and deploying the prosthetic heart valve into the valvular annulus using the catheter delivery system.

In another embodiment, there is provided a feature wherein the prosthetic heart valve is deployed by accessing the left heart using either an antegrade-trans(atrial)septal (transvenous-trans(atrial)septal) approach or a retrograde (transarterial-transaortic) catheter approach to enter the left heart, and deploying the prosthetic heart valve into the mitral annulus using the catheter delivery system.

In another embodiment, there is provided a feature wherein the prosthetic heart valve is deployed into the mitral annulus from a retrograde approach by accessing the left ventricle through the apex of the ventricular septum (transvenous-trans(ventricular)septal approach).

In another embodiment, there is a feature wherein the prosthetic heart valve is deployed into the mitral position using a retrograde transventricular septal approach and the tethers are anchored into or on the right ventricular side of the ventricular septum.

In another embodiment, there is provided a feature further comprising tethering the prosthetic heart valve to tissue within the left ventricle.

In another embodiment, there is provided a feature wherein the prosthetic heart valve is tethered to the apex of the left ventricle using an epicardial tether securing device.

In another embodiment, there is provided a retrieval method for quickly removing a prosthetic heart valve having one or more tethers from a patient using minimally invasive cardiac catheter techniques, which comprises the steps of, capturing the one or more tethers with a catheter having a snare attachment, guiding the captured tethers into a collapsible funnel attachment connected to the removal catheter, pulling the tethers to conform the prosthetic heart valve into a collapsed, compressed conformation, and pulling the now compressed prosthetic heart valve into the removal catheter for subsequent extraction. The retrieval method is contemplated for use for capturing the prosthetic heart valve as described herein or any suitable tethered, collapsible medical device. In a preferred embodiment, the method is used to extract a prosthetic heart valve from either the left or right ventricle. The method may be particularly useful to extract the prosthetic appliance during an aborted surgical deployment.

Narrow Gauge Stent

An embodiment relating to the design and function of a compressible prosthetic heart valve replacement having a narrow-diameter stent body, which can be deployed into a closed beating heart using a transcatheter delivery system. The design as discussed focuses on a prosthetic mitral valve that fits within the native mitral valve annulus, but does not compress or substantially interfere with the opening and closing of the native commissural leaflets located at the terminus of the native mitral valve leaflets.

As with previous devices, the deployment of this device is preferably via a minimally invasive surgical procedure utilizing percutaneous valve introduction through the intercostal or subxyphoid space, but can also be an endoscopic catheter-based antegrade, retrograde, or trans-septal deployment, as is know ion the arts. In order to accomplish this, the valve is formed in such a manner that it can be compressed to fit within a delivery system and secondarily ejected from the delivery system into the target location, for example the mitral or tricuspid valve annulus.

Accordingly, there is provided a method of deploying a prosthetic heart valve for the treatment of commissural regurgitation and/or secondary mitral regurgitation in a patient in need thereof, which comprises the step of using a cardiac imaging device to measure the diameter of the native mitral annulus for selection and delivery of a prosthetic mitral valve, the improvement consisting of using the same or different cardiac imaging device and measuring the distance from the posterior edge of the posterior leaflet to the anterior edge of the anterior leaflet and the posterior leaflet to define a cross-sectional leaflet diameter, wherein said cross-sectional leaflet diameter is substantially less than the maximum diameter of the mitral annulus, said maximum diameter defined as the distance from the mitral annulus adjacent the anterolateral commissure to the mitral annulus adjacent the posteromedial commissure.

In a preferred embodiment, there is provided for use herein a prosthetic transcatheter valve comprising an expandable tubular stent having a cuff and an expandable internal leaflet assembly, wherein the diameter of said stent is less than the distance between the internal tips of the commissural cusps, and wherein said leaflet assembly is disposed within the stent and is comprised of stabilized tissue or synthetic material.

In one preferred embodiment, there is also provided a prosthetic heart valve as described herein wherein the diameter of the stent is approximate to the distance between the interior tips of the commissural cusps.

In another preferred embodiment, there is also provided a prosthetic heart valve as described herein wherein the diameter of the stent is between 18 mm and 32 mm.

In another preferred embodiment, there is also provided a prosthetic heart valve as described herein wherein the diameter of the stent is between 20 mm and 30 mm.

In another preferred embodiment, there is also provided a prosthetic heart valve as described herein wherein the diameter of the stent is between 23 mm and 28 mm.

In another preferred embodiment, there is also provided a prosthetic heart valve as described herein wherein the stent is sized to cover between 75% and 99% of the mitral valve area.

In another preferred embodiment, there is also provided a prosthetic heart valve as described herein wherein the stent is sized to cover between 85% and 98% of the mitral valve area.

In another preferred embodiment, there is also provided a prosthetic heart valve as described herein wherein the stent is sized to cover between 92% and 97% of the mitral valve area.

In another preferred embodiment, there is also provided a prosthetic heart valve as described herein wherein the stent is sized to allow for a degree of mitral regurgitation of 20% or less.

In another preferred embodiment, there is also provided a prosthetic heart valve as described herein wherein the stent is sized to allow for a degree of mitral regurgitation of 10% or less.

In another preferred embodiment, there is also provided a prosthetic heart valve as described herein wherein the stent is sized to allow for a degree of mitral regurgitation of 5% or less.

In another preferred embodiment, there is also provided a cuff for a narrow gauge prosthetic heart valve for treatment of commissural regurgitation and/or secondary mitral regurgitation, wherein the cuff has an articulating structure made of a superelastic metal that is covered with stabilized tissue or synthetic material, with only the portion of the cuff overlaying the commissures left uncovered.

In another preferred embodiment, there is also provided a method of treating mitral secondary regurgitation in a patient, which comprises the step of surgically deploying the narrow gauge prosthetic heart valve described herein into the mitral annulus of the patient.

In another preferred embodiment, there is also provided wherein the prosthetic heart valve is deployed by directly accessing the heart through the intercostal space, using an apical approach to enter the left ventricle, and deploying the prosthetic heart valve into the mitral annulus, or wherein the prosthetic heart valve is deployed by directly accessing the heart through a thoracotomy, sternotomy, or minimally-invasive thoracic, thorascopic, or trans-diaphragmatic approach to enter the left ventricle, or wherein the prosthetic heart valve is deployed by directly accessing the heart through the intercostal space, using an approach through the lateral ventricular wall to enter the left ventricle, or wherein the prosthetic heart valve is deployed by accessing the left atrium of the heart using a transvenous atrial septostomy approach, or wherein the prosthetic heart valve is deployed by accessing the left ventricle of the heart using a transarterial retrograde aortic valve approach, or wherein the prosthetic heart valve is deployed by accessing the left ventricle of the heart using a transvenous ventricular septostomy approach.

In another preferred embodiment, there is also provided a method wherein the prosthetic heart valve is tethered to the apex of the left ventricle using an epicardial tether securing device.

In another preferred embodiment, there is also provided a method of treating commissural regurgitation and/or secondary mitral regurgitation by (1) measuring the area of the native valve and the regurgitant fraction using known imaging techniques; (2) sizing a prosthetic valve of claim 1 to allow between a 1% and 20% regurgitant fraction through the native commissures, based on the measures of step (1); and (3) implanting such prosthetic valve within the native mitral annulus.

BRIEF DESCRIPTION OF THE DRAWINGS

Improved Surfaces

FIG. 6 shows the delivery catheter advanced to through the mitral valve and into the left atrium for deployment of the prosthetic valve.

FIG. 7 shows the delivery catheter advanced to the mitral valve and into the left atrium for deployment of the prosthetic valve.

FIG. 8 shows the delivery catheter advanced through to the tricuspid valve and into the right atrium for deployment of the prosthetic valve.

Shuttlecock Annular Valve

Figure 12:
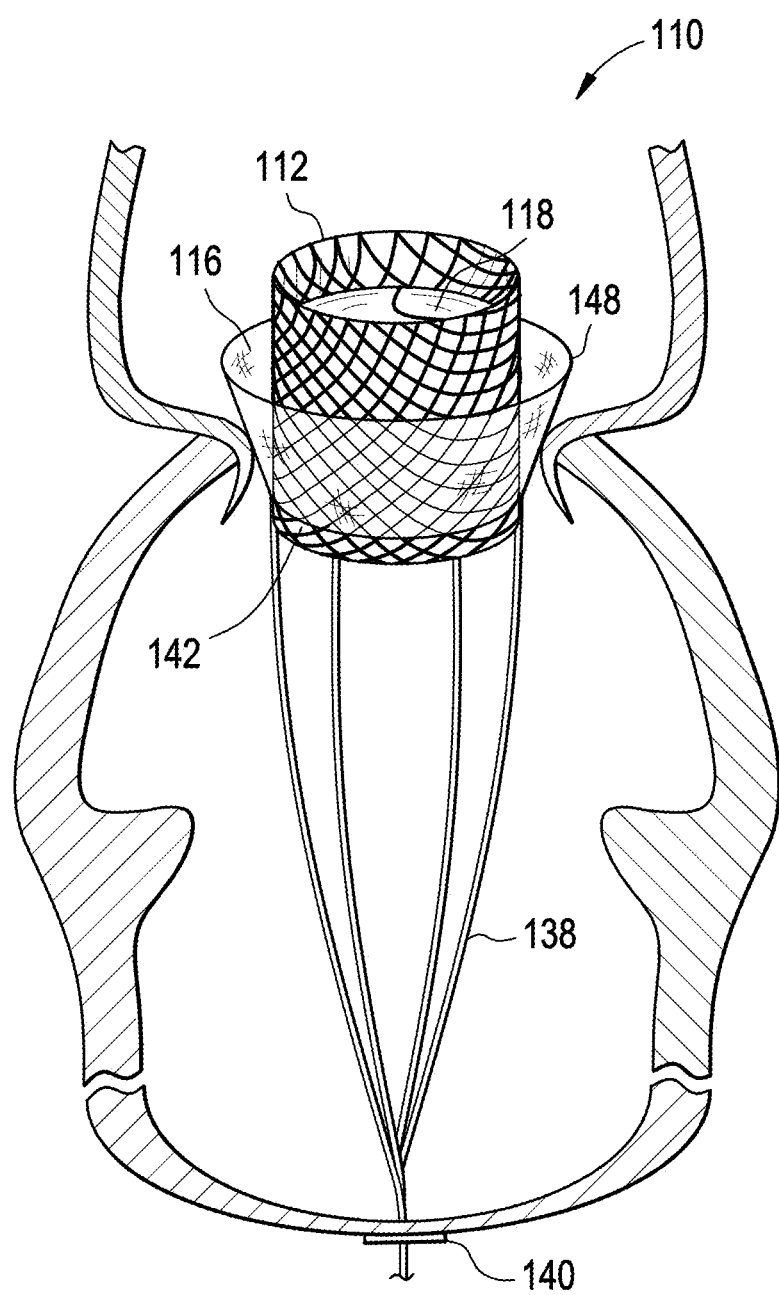

FIG. 12 is an illustration of a perspective view of a collared stent according to the present invention tethered to tissue within the left ventricle.

Figure 13A:
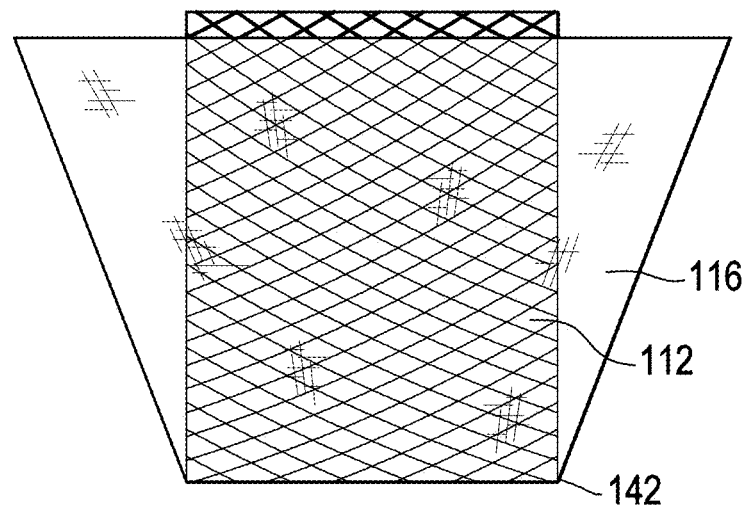
Figure 13B:
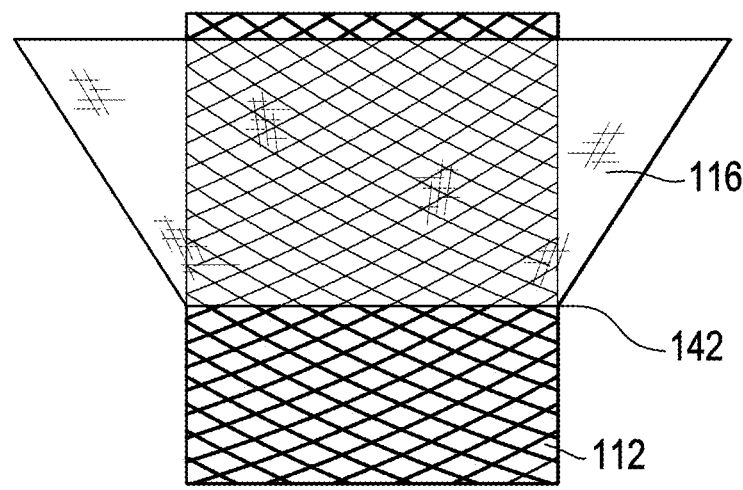

FIGS. 13A and 13B are illustrations of a side view showing how the collar can originate at varying points on the exterior wall of the stent body.

Figure 14A:
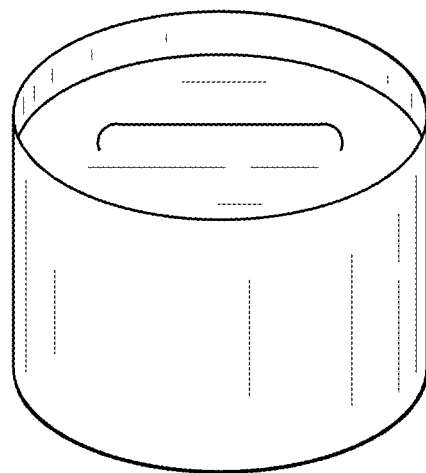
Figure 14B:
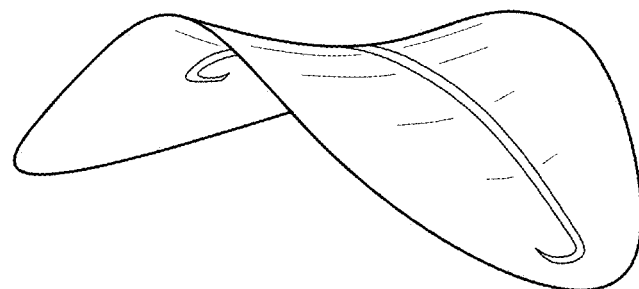
Figure 14C:
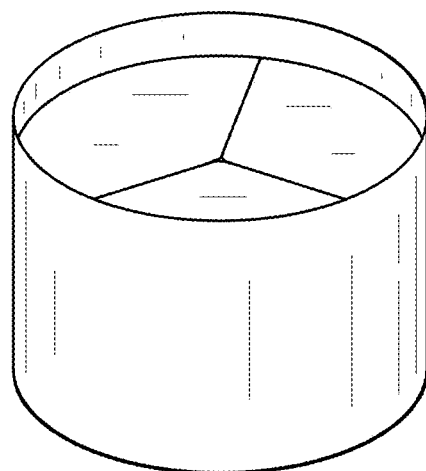

FIGS. 14A-14C are illustrations showing how the valve leaflets can vary and may include bicuspid/mitral and tricuspid embodiments.

Figure 15:
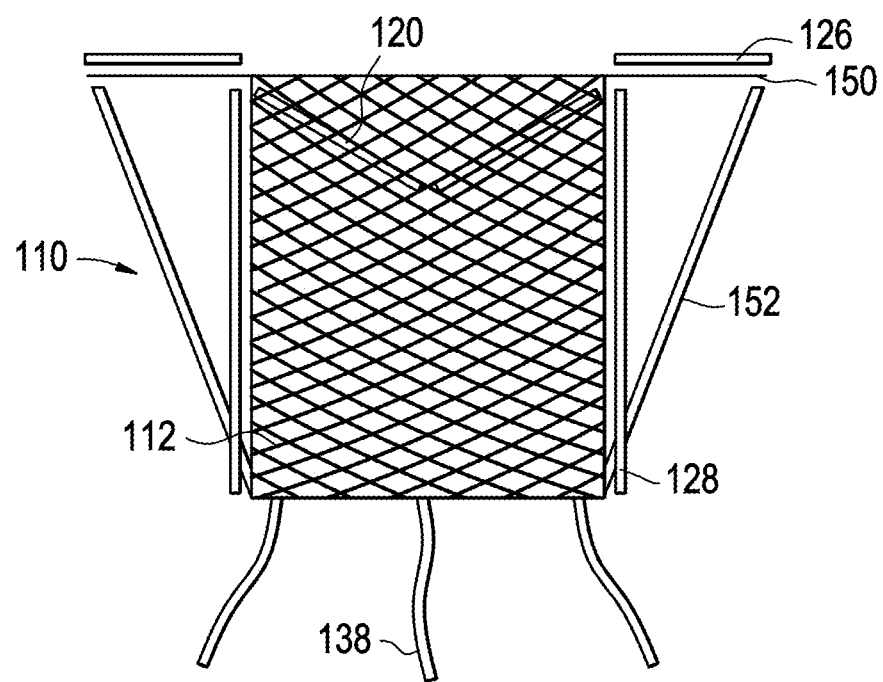

FIG. 15 is a side view illustration showing how the stent body and collar support structure may be covered with thin tissue, and how the collar may be a web of elastic polymeric material spanning from the distal end of the stent to the edge of the collar support structure.

Figure 16:
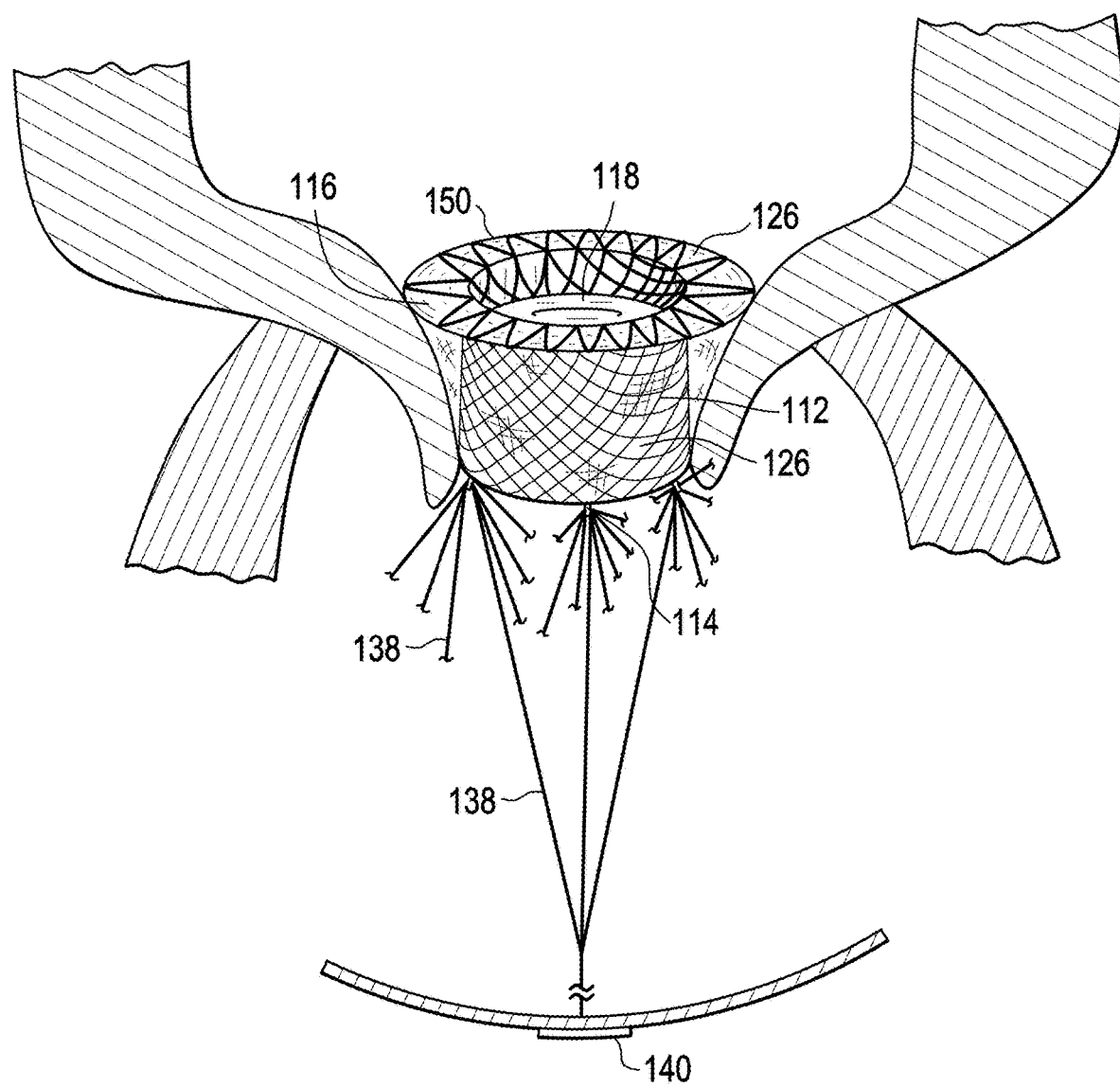

FIG. 16 is a perspective view illustration of one embodiment of the present invention deployed with the mitral valve annulus, forming a complete seal between the left atrium and ventricle, and showing how the collar may be a mesh material spanning between an integrated stent-support structure assembly, and showing that a large number of anchoring tethers are contemplated as within the scope of the present invention, including a tether to the apex of the left ventricle for attachment to a pledget on the pericardial surface.

Figure 17:
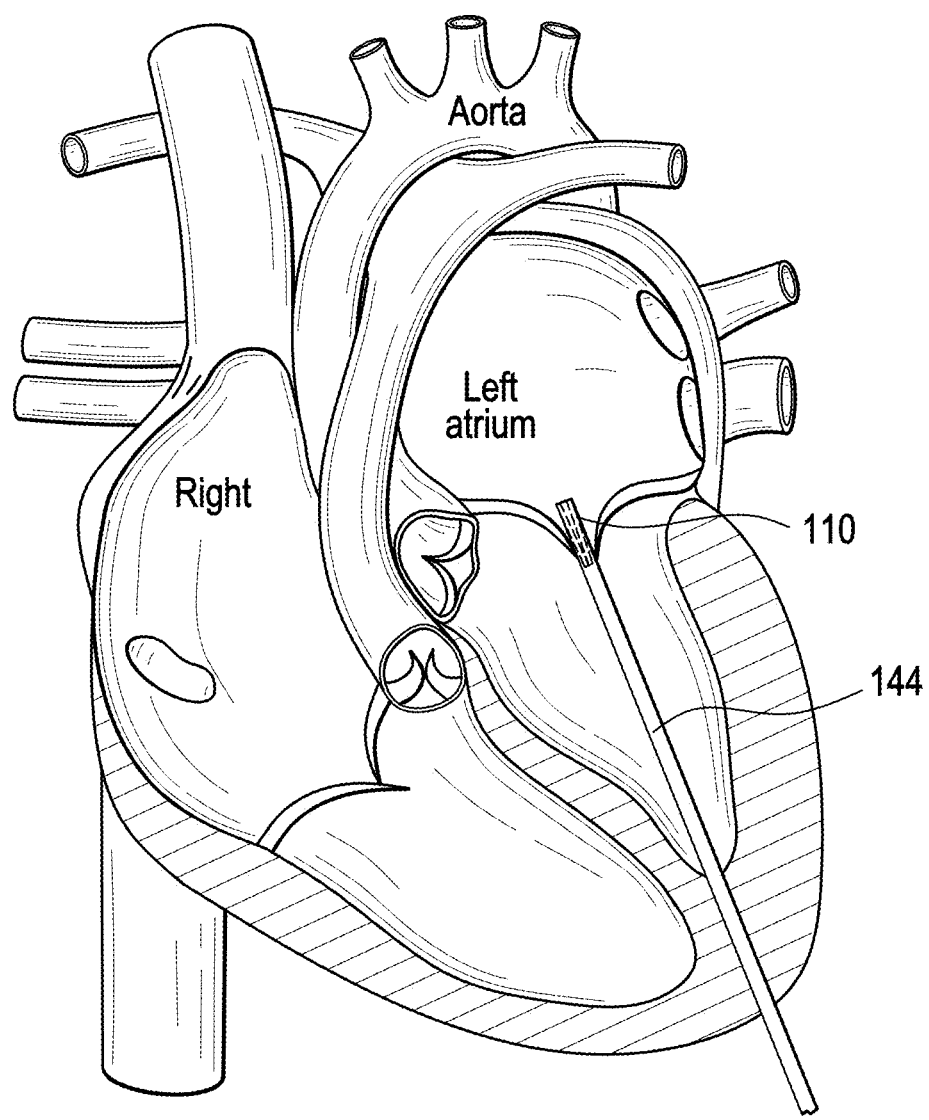

FIG. 17 is a cut-away view of a heart with a delivery catheter containing a prosthetic valve according to the present invention and accessing the heart using an apical approach. FIG. 17 shows the delivery catheter advanced to through the mitral valve and into the left atrium for deployment of the prosthetic valve.

Figure 18:
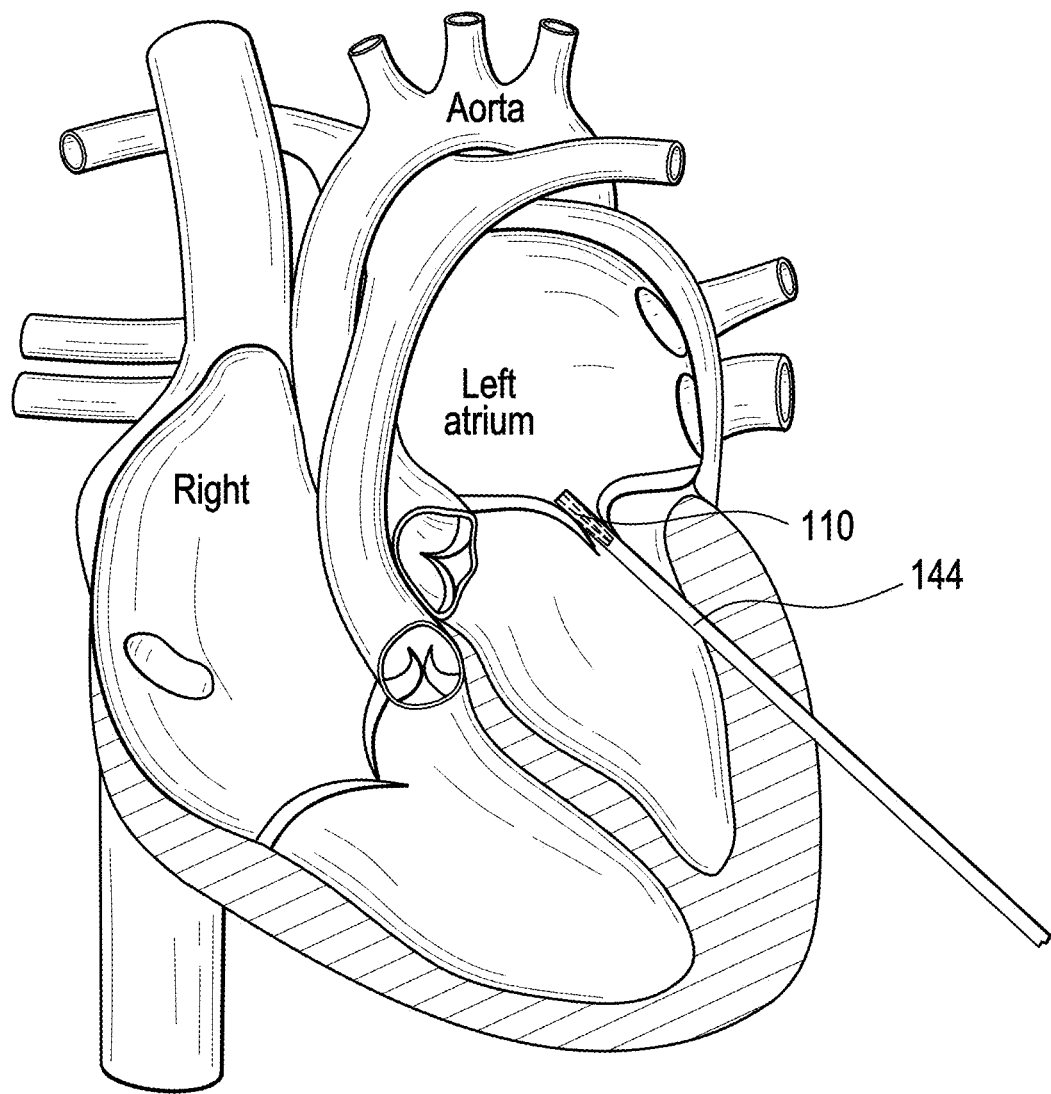

FIG. 18 is a cut-away view of a heart with a delivery catheter containing a prosthetic valve according to the present invention and accessing the heart using a lateral approach. FIG. 18 shows the delivery catheter advanced to the mitral valve and into the left atrium for deployment of the prosthetic valve.

Figure 19:
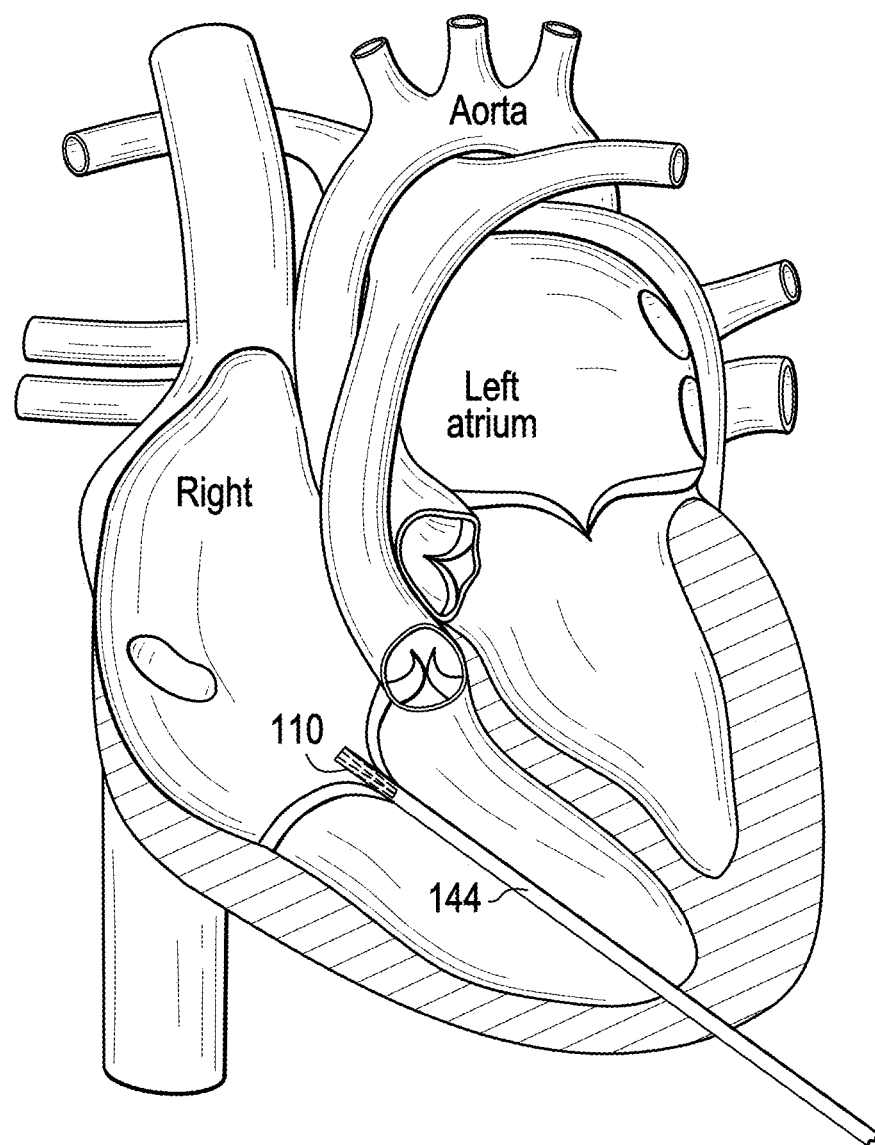

FIG. 19 is a cut-away view of a heart with a delivery catheter containing a prosthetic valve according to the present invention and accessing the right ventricle of the heart using an apical approach. FIG. 19 shows the delivery catheter advanced through to the tricuspid valve and into the right atrium for deployment of the prosthetic valve.

FIGS. 20A-20D are illustrations of how the three-dimensional shape may vary, including a D-shape and a kidney-bean-shaped valve.

Spring Anchor

Figure 21:
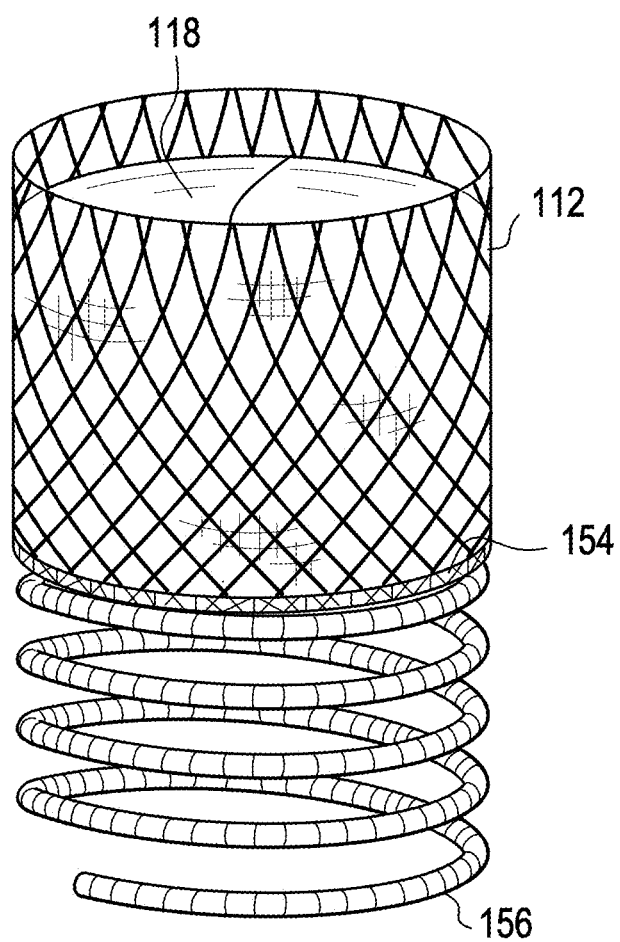

FIG. 21 is an illustration of a perspective view of a spring-shaped anchor attached to a non-collared stent according to the present invention.

Figure 22:
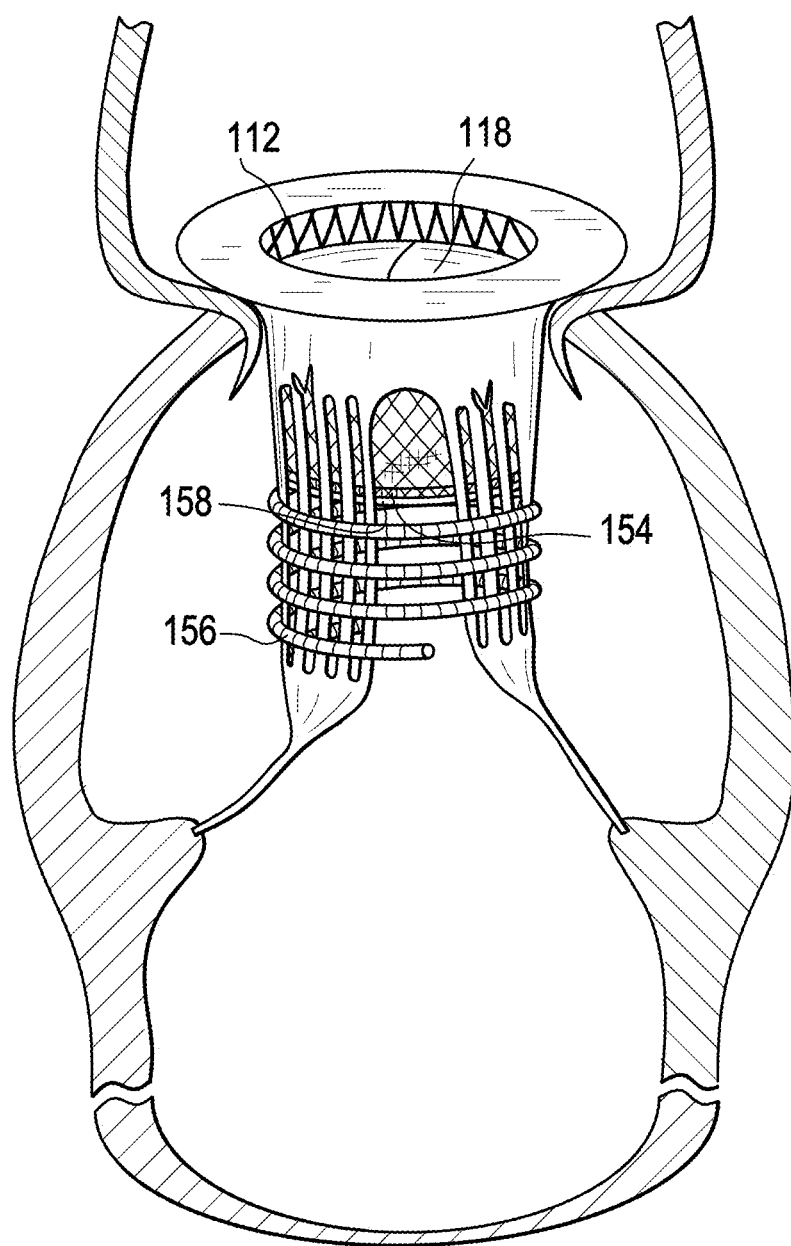

FIG. 22 is an illustration of a perspective view the spring-shaped anchor securing the attached stent into the mitral valve annulus of a human heart by rotatably fitting around the chordae tendineae.

Figure 23A:
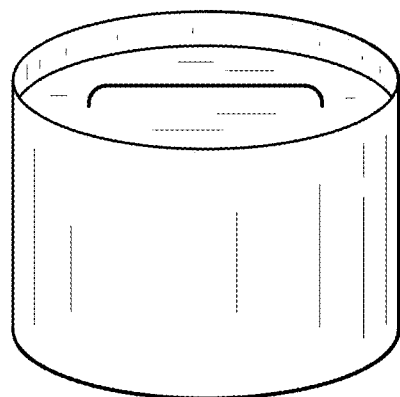
Figure 23B:
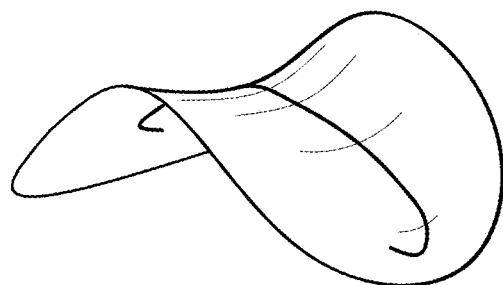
Figure 23C:
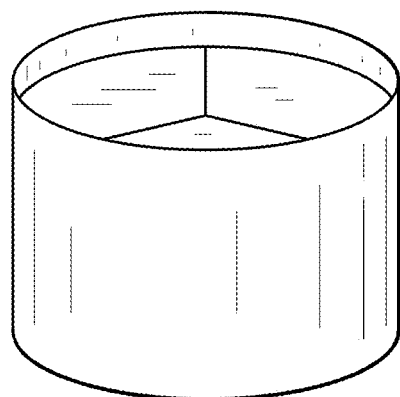

FIGS. 23A-23C are illustrations showing how the valve leaflets can vary and may include bicuspid/mitral and tricuspid embodiments.

Figure 24:
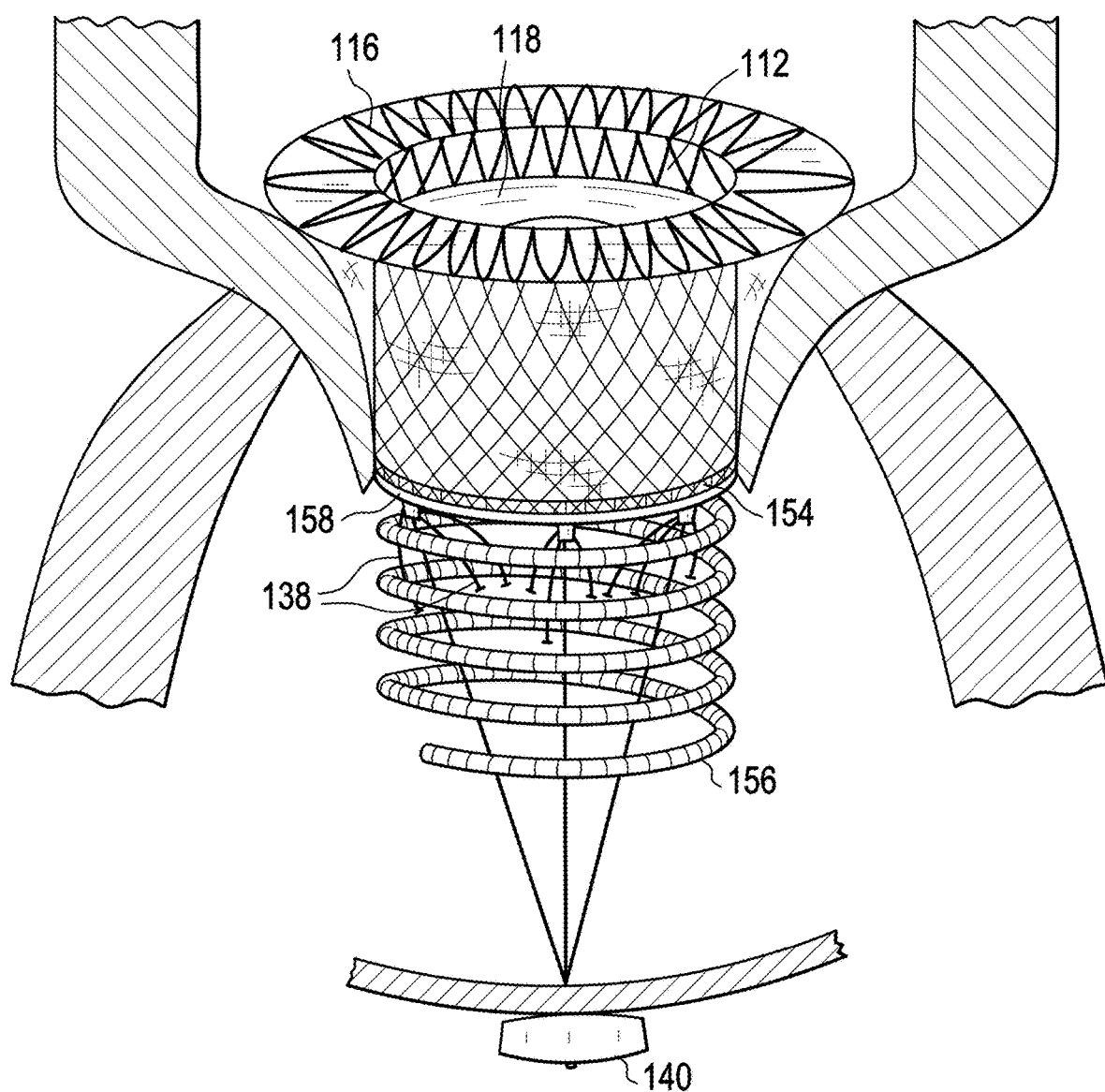

FIG. 24 is a perspective view illustration of one embodiment of the present invention emanating from a prosthetic valve deployed within the mitral valve annulus, forming a complete seal between the left atrium and ventricle. FIG. 24 shows a collared version of a prosthetic valve, made from a mesh material spanning between an integrated stent-support structure assembly, and, in addition to the spring anchor deployed about the chordae tendineae, further illustrates a plurality of anchoring tethers contemplated as within the scope of the present invention, including tethers to the apex of the left ventricle for attachment to a pledget on the pericardial surface.

Figure 25:
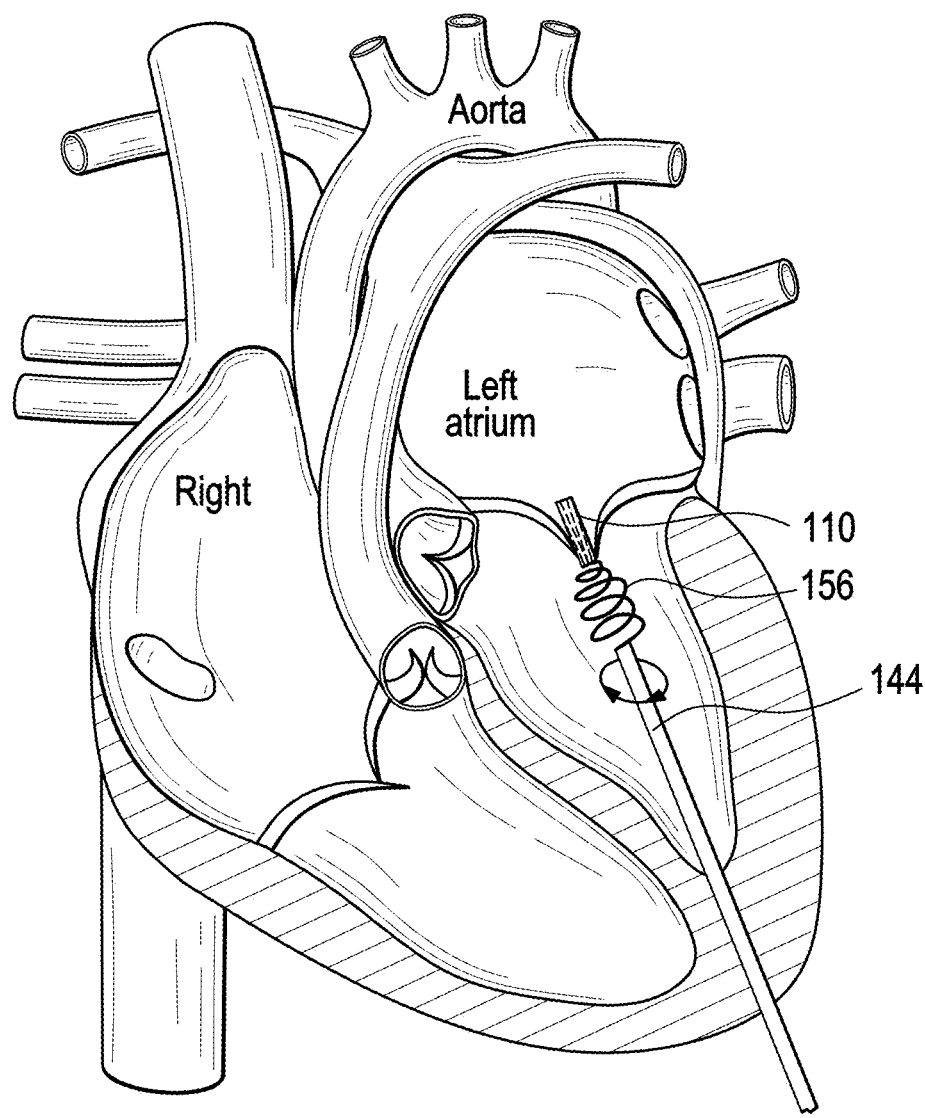

FIG. 25 is a cut-away view of a heart with a delivery catheter containing a prosthetic mitral valve and rotatably encircling the chordae tendineae with the spring anchor according to the present invention and accessing the heart using an apical approach into the left ventricle.

Figure 26:
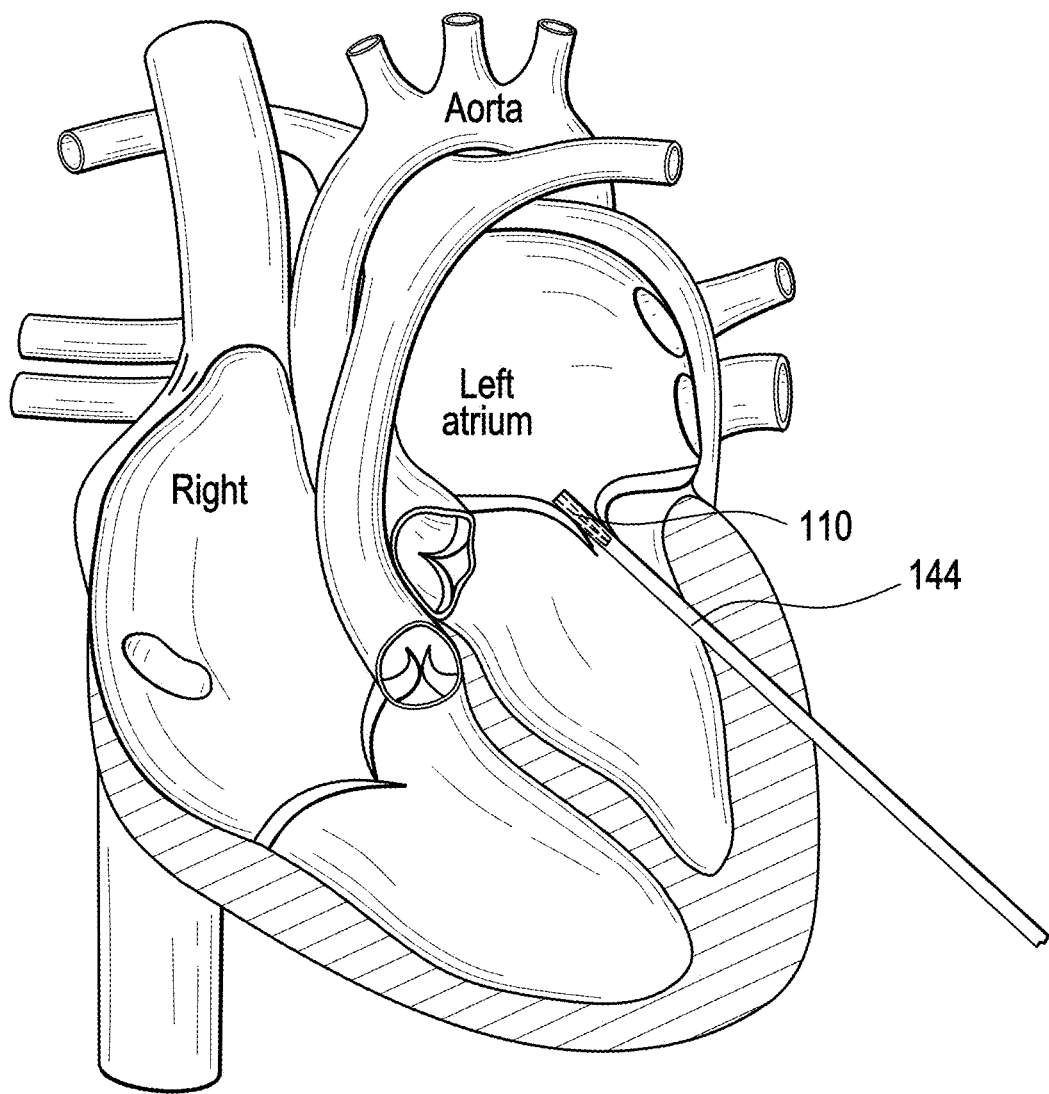

FIG. 26 is a cut-away view of a heart with a delivery catheter containing a prosthetic valve according to the present invention and accessing the heart using a lateral approach. FIG. 26 shows the delivery catheter advanced to the mitral valve and into the left atrium for deployment of the prosthetic valve prior to deployment of the spring anchor.

Figure 27:
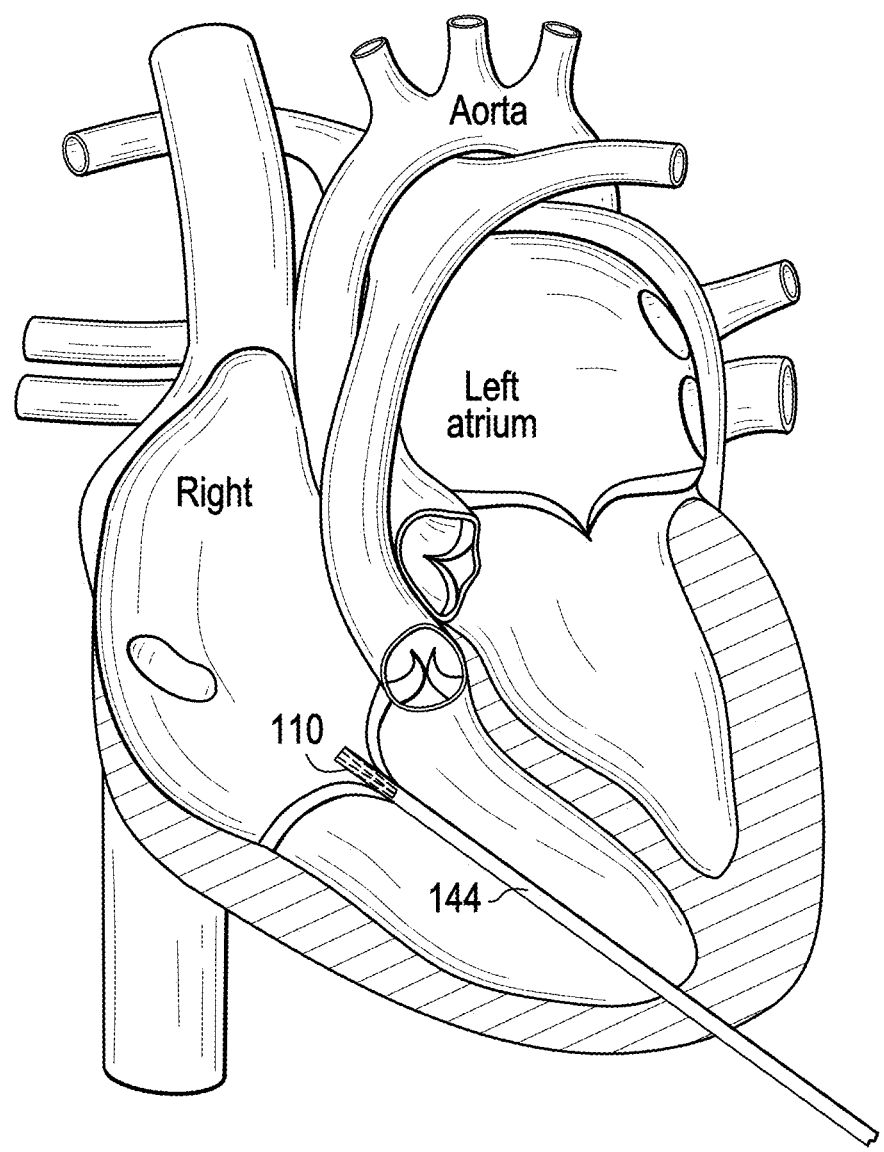

FIG. 27 is a cut-away view of a heart with a delivery catheter containing a prosthetic valve and spring anchor according to the present invention and accessing the right ventricle of the heart using an apical approach. FIG. 27 shows the delivery catheter advanced through to the tricuspid valve and into the right atrium for deployment of the prosthetic valve prior to deployment of the spring anchor.

Annular Clamps

Figure 28A:
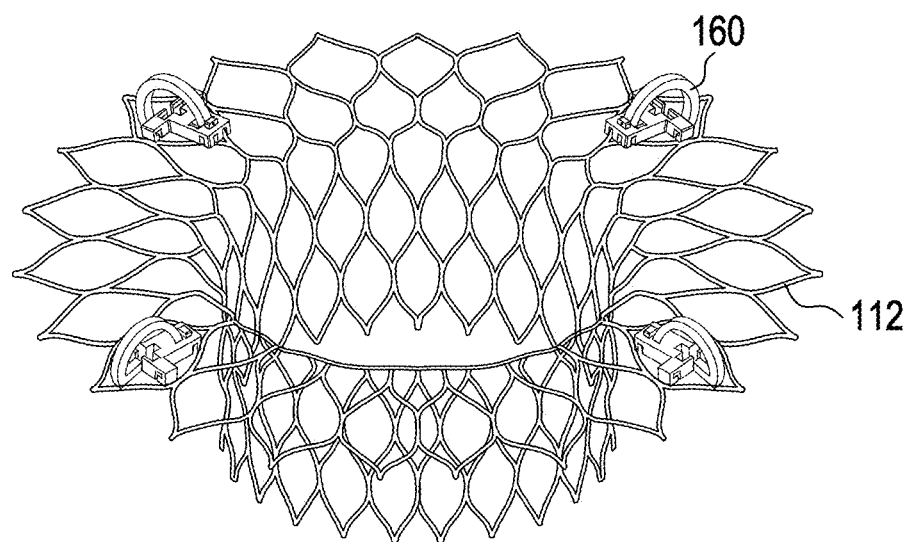
Figure 28B:
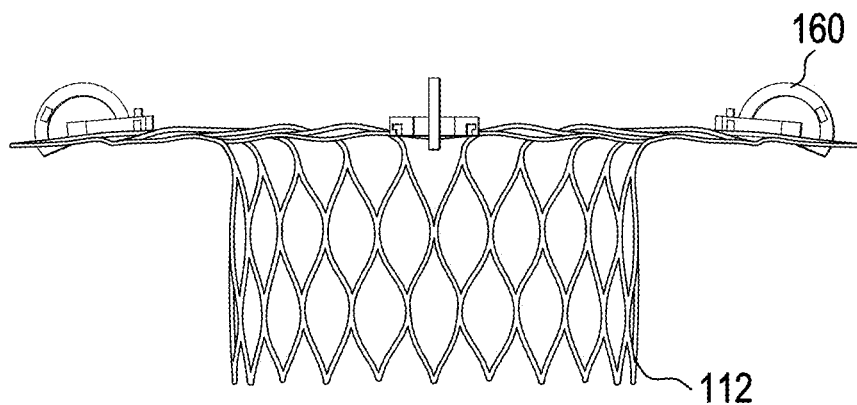

FIG. 28A shows a perspective view of a braided wire stent with four clamp-style annulus anchoring members located around the outside. FIG. 28B shows a side view of the same braided wire stent with four clamp-style annulus anchoring members.

Figure 29:
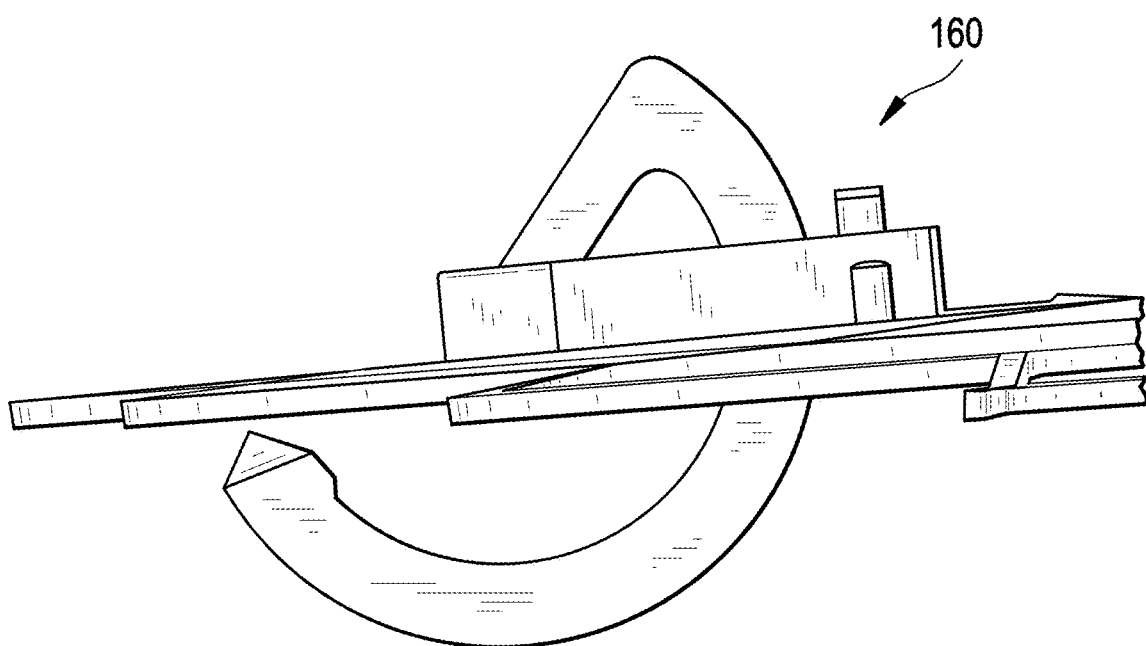

FIG. 29 shows a side view of a clamp-style annulus anchoring member.

Figure 30A:
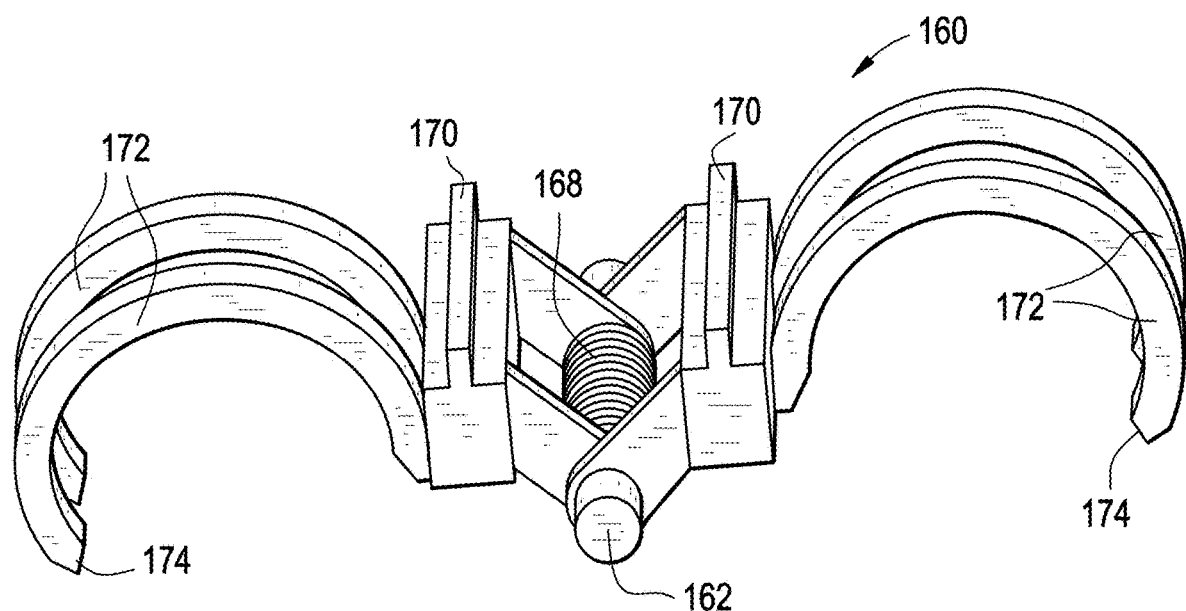
Figure 30B:
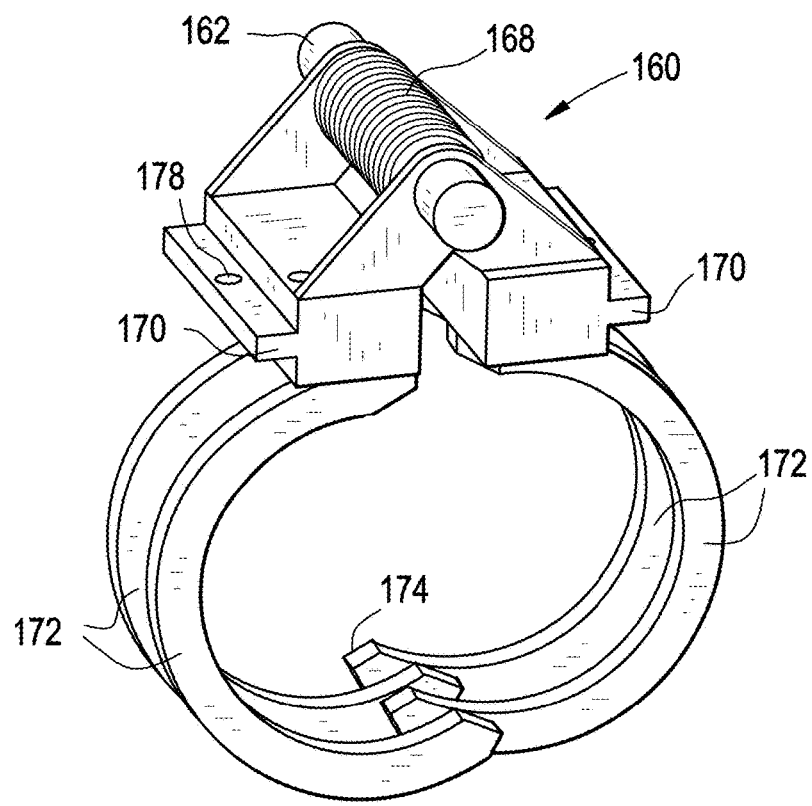

FIG. 30A shows a perspective view of a clamp-style annulus anchoring member in the open position, comprising the following parts: pin, spring, two interdigitated middle members, two pairs of semicircular fingers, each with a tapered point. FIG. 30B shows a perspective view of the same clamp shown in FIG. 30A, but in the closed position with the ends of the semicircular fingers interdigitated.

Figure 31A:
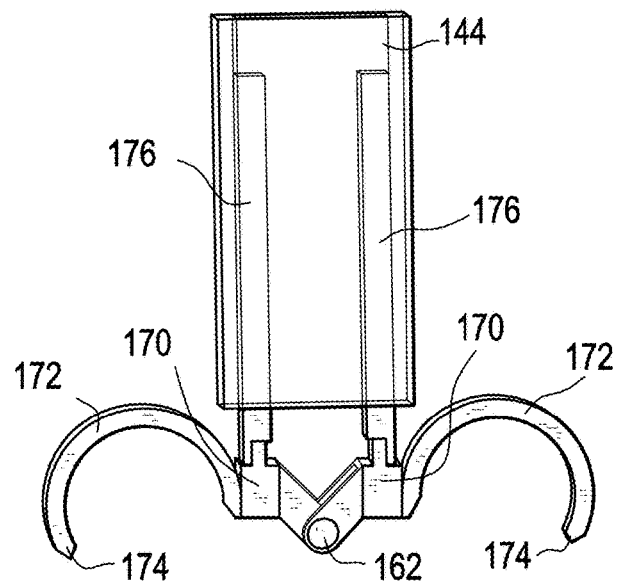
Figure 31B:
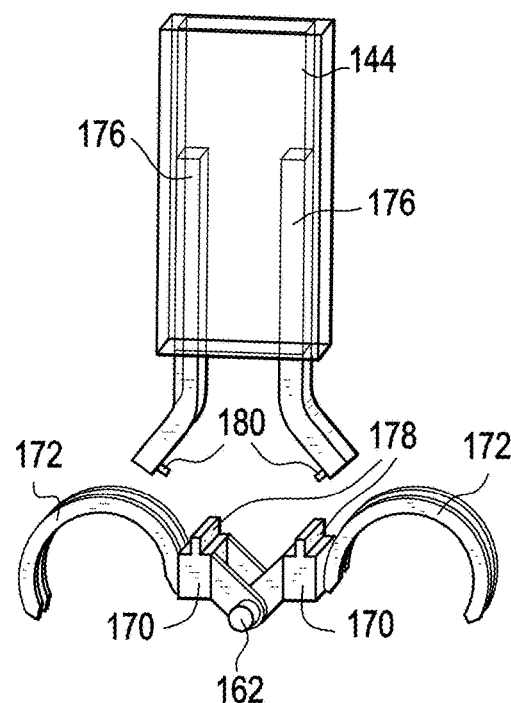

FIG. 31A shows a side view of the clamp-style annulus anchoring member shown in FIG. 30A, but with a pressure-bearing member attached to the flange portion of each middle member via the hole centered in such flange, and exerting pressure to hold the clamp open. The pressure bearing members are emanating from a catheter in a straight position, exerting outward pressure on the clamp to hold it open. FIG. 31B shows a partially exploded view of the clamp and pressure bearing members, evidencing the holes centered in the middle member flanges and the male attachment stud of each pressure bearing member. The figure shows the moment of release as the crimped point of the pressure bearing members extend from their housing and cause the pressure bearing members to release from the middle members of the clamp, thereby allowing the torque of the spring to snap the clamp shut.

Figure 32A:
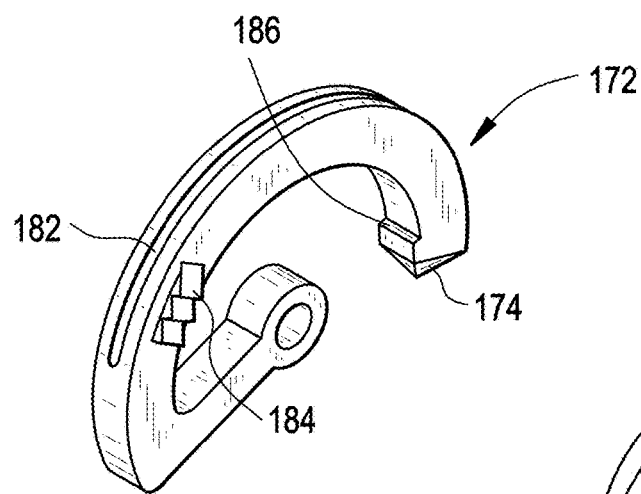
Figure 32B:
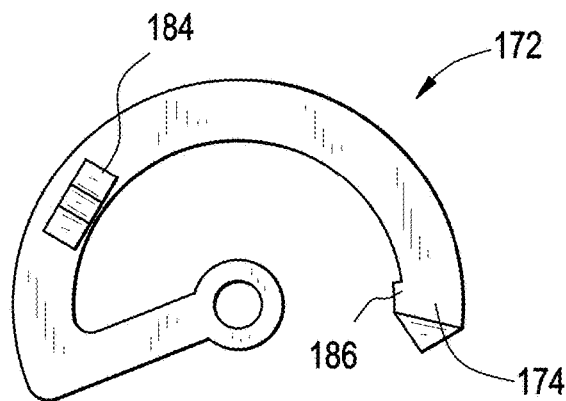

FIG. 32A shows a perspective view of a single semicircular finger, with a slot along the outer ridge and a series of triangular protrusions along one side for interlocking with another finger of the same design. FIG. 32B shows a side view of the same semicircular finger pictured in FIG. 32A.

Figure 33A:
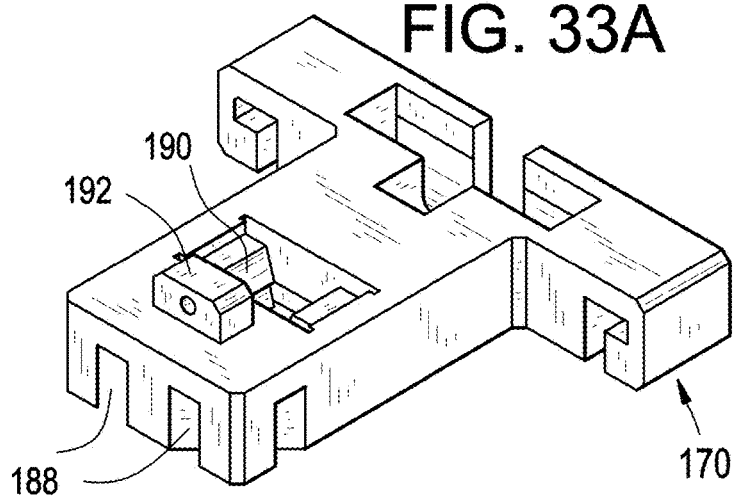
Figure 33B:
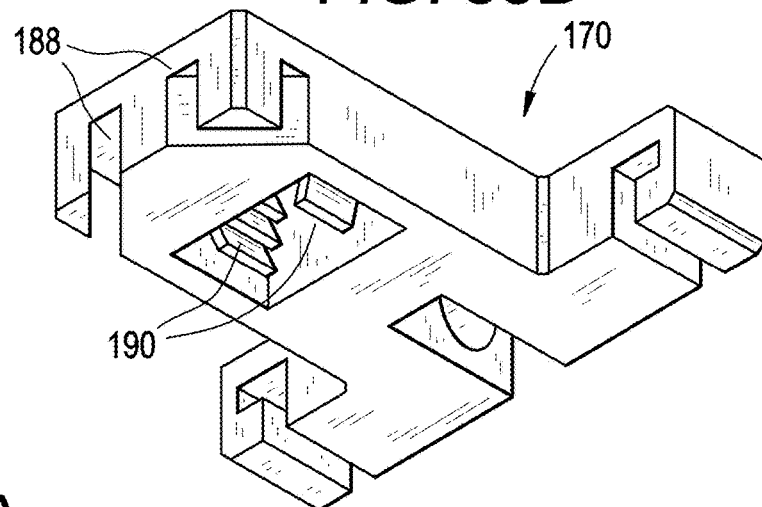

FIG. 33A shows a perspective view of the outer and distal side of the center portion component of a middle member of the clamp assembly shown in FIG. 33A, with machine tooling slots and a ridged locking mechanism for interlocking with other components of the clamp assembly. FIG. 33B shows a perspective view of the inner and distal side of the same center portion component pictured in FIG. 33A.

Figure 34A:
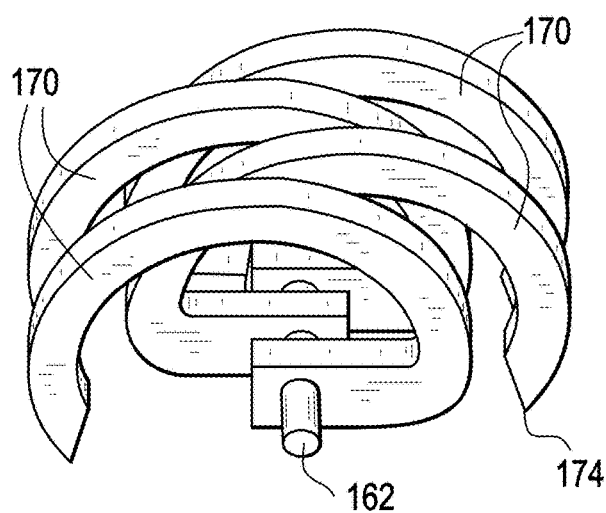
Figure 34B:
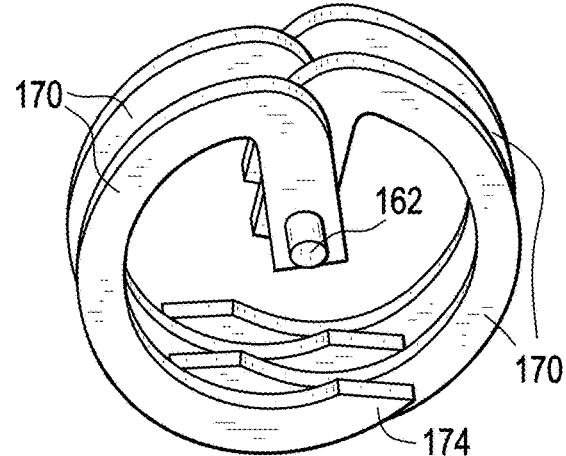

FIG. 34A shows a perspective view of a clamp assembly in the open position, comprising a set of four closing members, each with a hole bored directly into its proximal end through which a pin has been threaded, with the closing members interdigitated such that the first and third closing members close in one direction while the second and fourth closing members close in the opposite direction. Each closing member has a tapered distal tip. FIG. 34B shows the same assembly as FIG. 34A, but in the closed position.

Figure 35A:
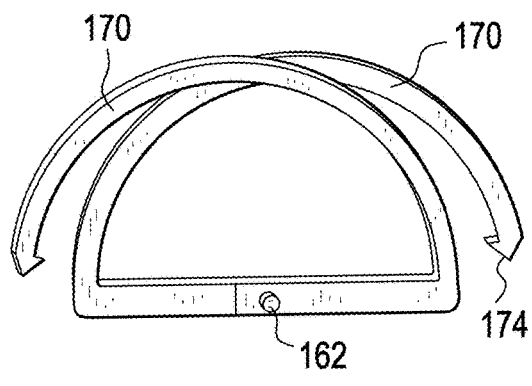
Figure 35B:
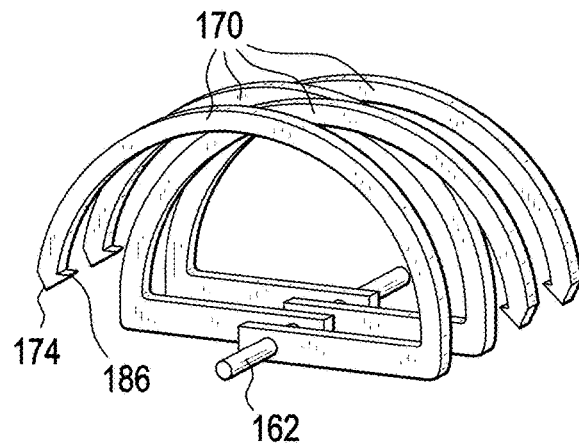

FIG. 35A shows a side perspective of a clamp assembly in the open position, comprising a set of four closing members, each with a hole bored directly into its proximal end through which a pin has been threaded, with the closing members interdigitated such that the first and third closing members close in one direction while the second and fourth closing members close in the opposite direction. Each closing member has a tapered distal tip with a fish hook feature. FIG. 35B shows the same assembly as FIG. 34A, from an angled perspective.

Figure 36A:
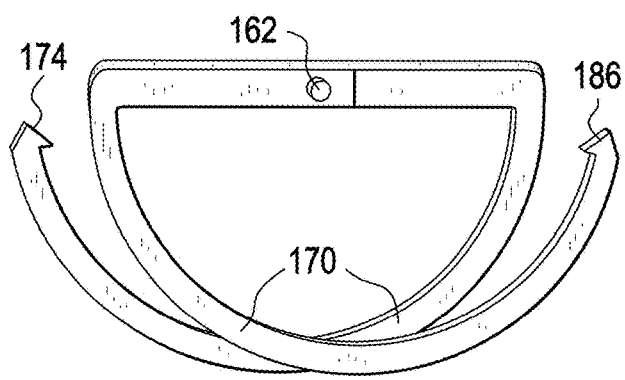
Figure 36B:
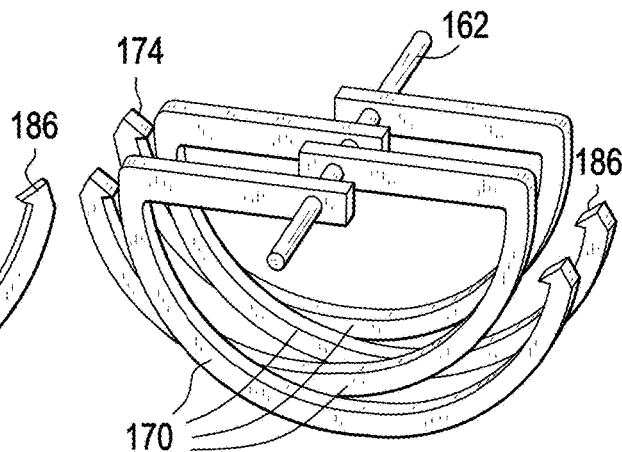
Figure 37A:
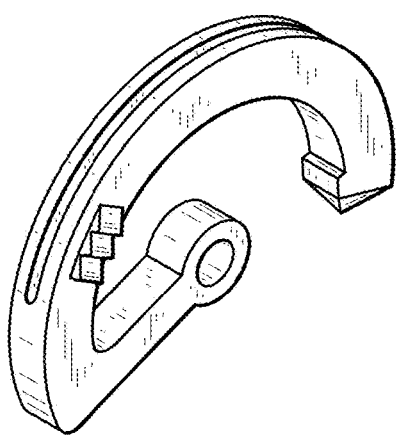
Figure 37B:
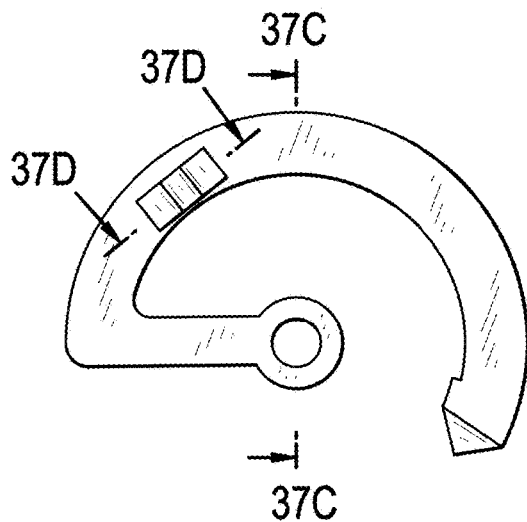
Figure 37C:
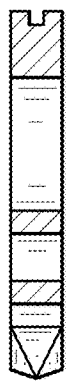
Figure 37D:
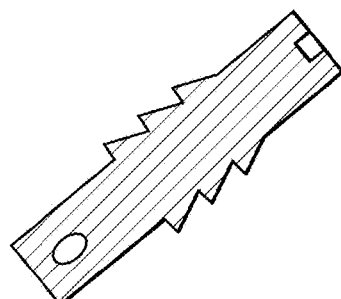
Figure 37E:
Figure 37F:
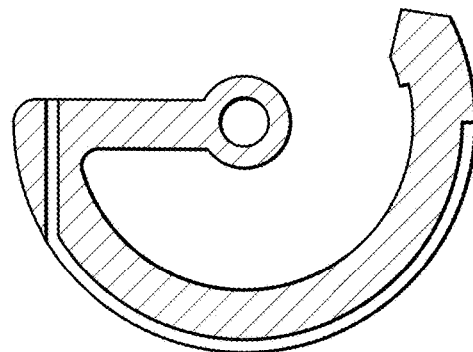

FIG. 36A shows a side view of the clamp assembly of FIG. 35A, but in a closed position. FIG. 36B shows the same assembly as FIG. 36A, but from an angled perspective.

FIGS. 37A-37F show a variety of possible dimensions of various components of a clamp assembly.

Figure 38:
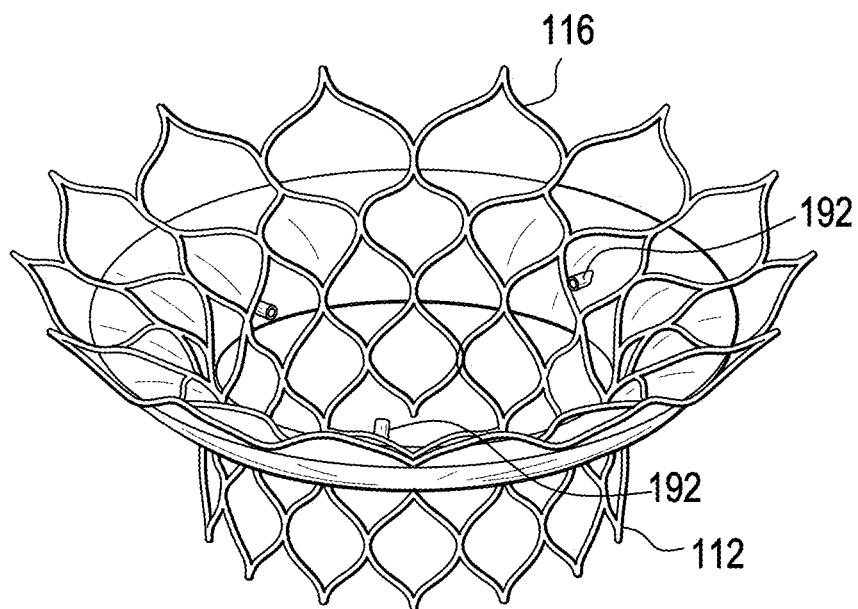

FIG. 38 shows a braided stent with an annulus component comprising stud assemblies for a suction fin and glue fin.

Figure 39:
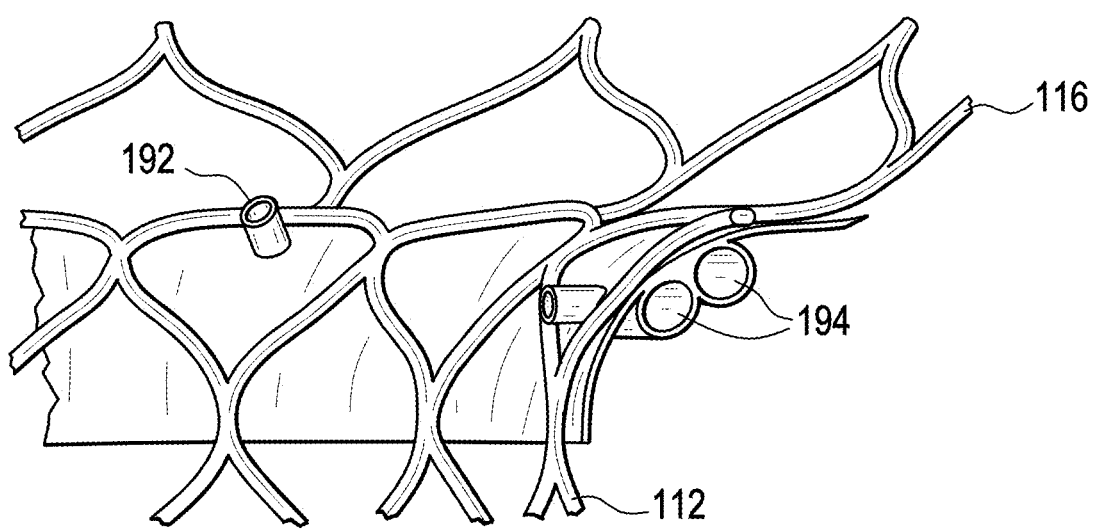

FIG. 39 shows a cross-section of the annulus component of the stent of FIG. 38, evidencing two stable inner tubes for suction and application of glue.

Figure 40:
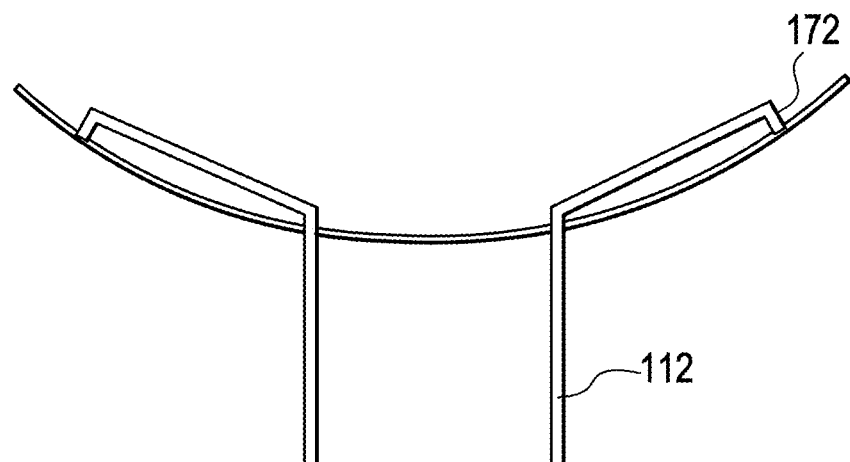

FIG. 40 is a line drawing evidencing the angle of stent to grabber.

Figure 41:
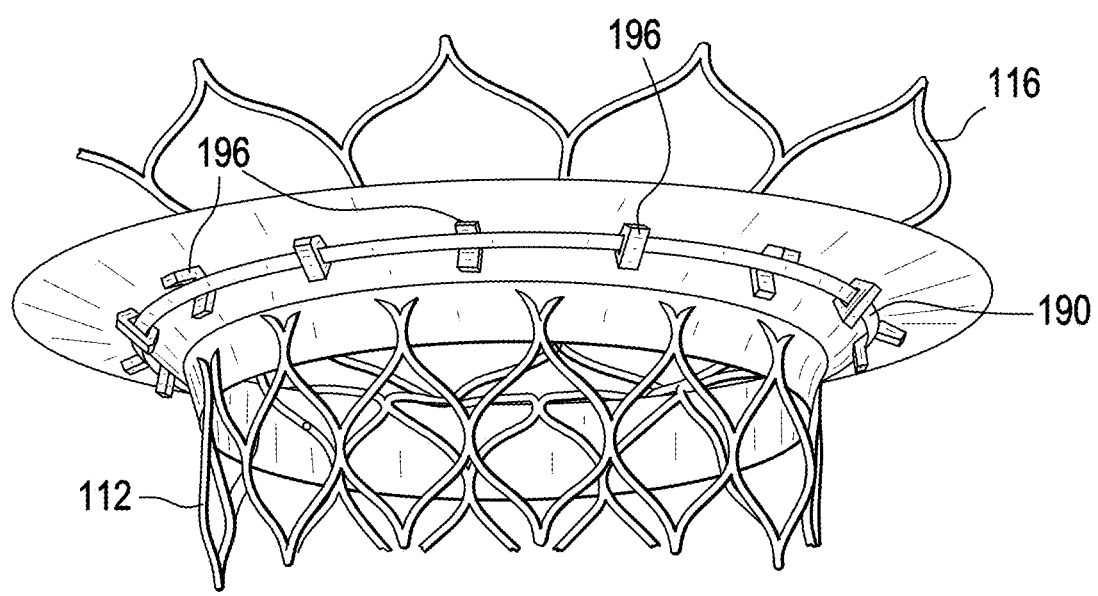

FIG. 41 is a perspective view from an underneath angle of a braided stent around which a prosthetic annulus has been attached, further evidencing a series of clamping devices circumnavigating the prosthetic annulus, each such device clamping down a security belt.

Figure 42:
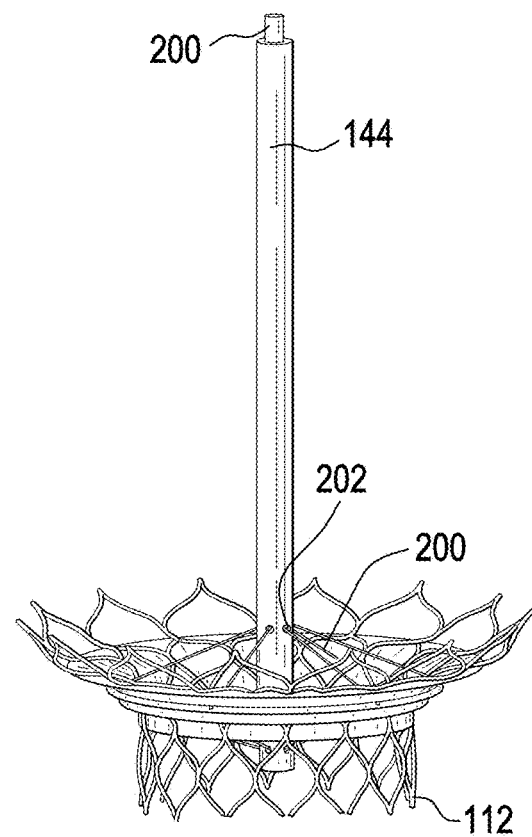

FIG. 42 evidences a perspective view of a guidance catheter located within the stent pictured in FIG. 41, with wires emanating from holes around the catheter body and attached through the prosthetic annulus to the clamp devices pictured in FIG. 41.

Figure 43:
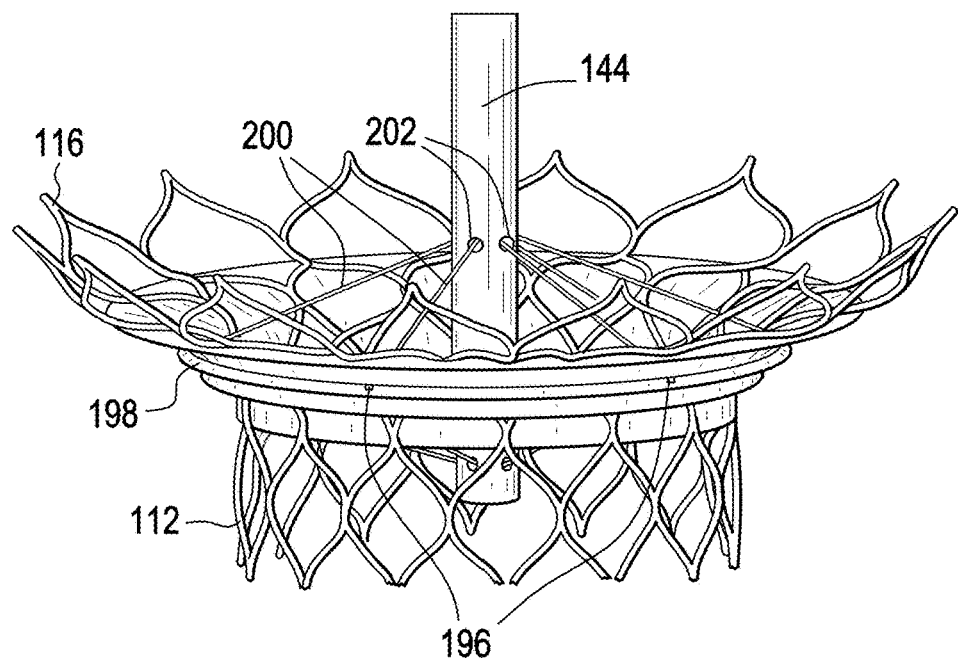

FIG. 43 shows a closer view of the guide catheter, stent and strings of FIG. 42.

Figure 44:
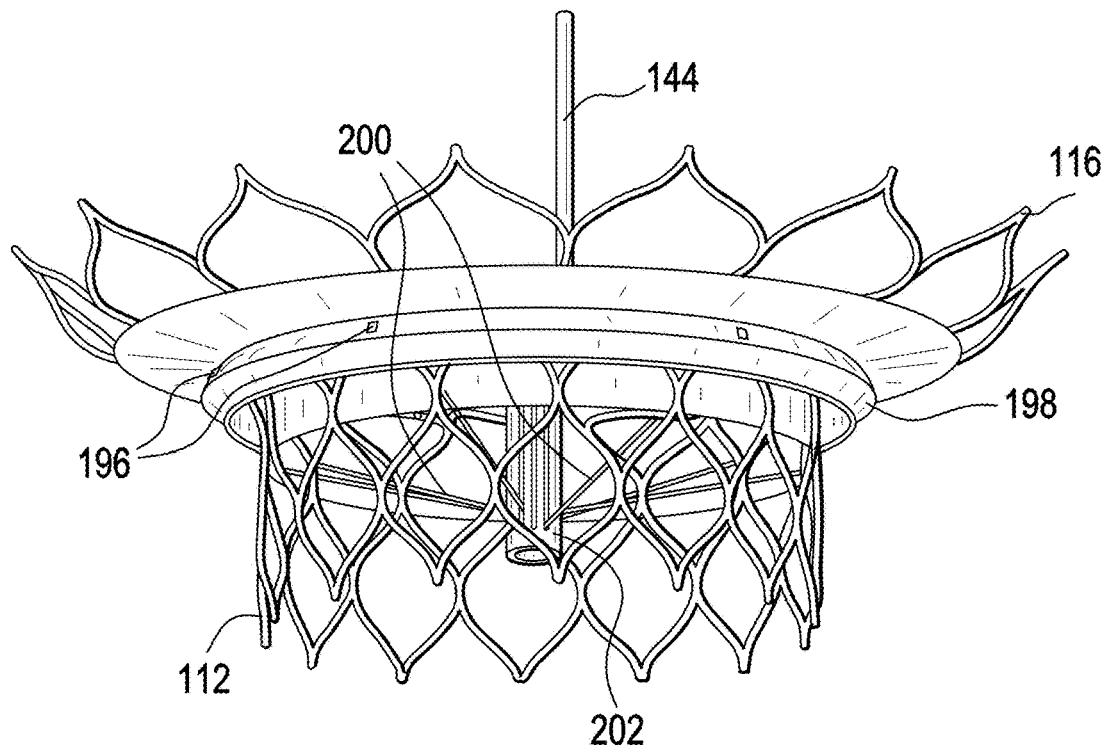

FIG. 44 shows an underneath view of the guidance catheter, string and stent assembly of FIGS. 41-43, evidencing the mechanism by which pulling the strings through the catheter closes the clamp devices around the security belt.

Figure 45:
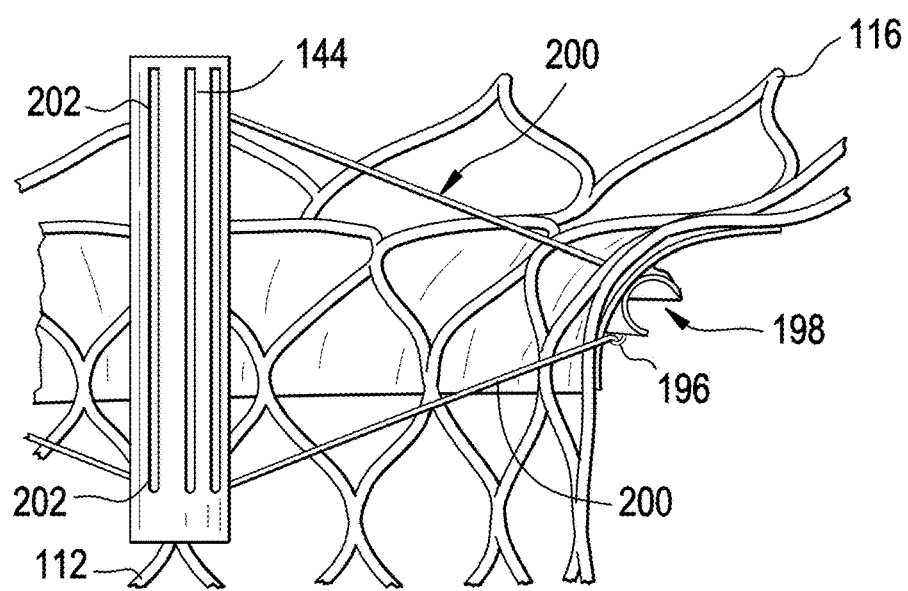

FIG. 45 shows a close view from a perspective inside the stent of the guidance catheter, string and stent assembly of FIGS. 41-44, evidencing a cross-section of the guidance catheter and a cross-section of the prosthetic annulus, evidencing the perforation of the prosthetic annulus by each string and the connection of each string to a clamping device.

Improved Cuff/Collar Variations

Figure 46:
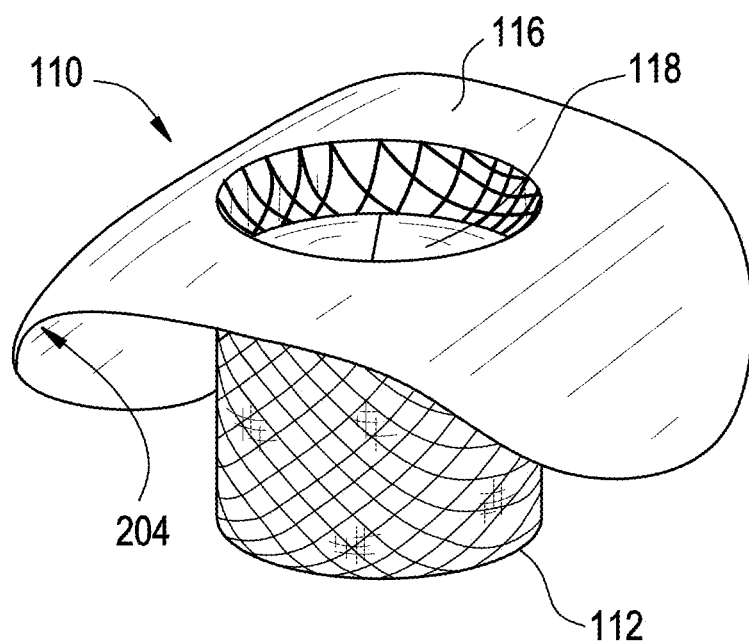

FIG. 46 is a perspective view of one embodiment of an improved atrial cuff/collar wherein the shape to the cuff/collar is agaricoid.

Figure 47:
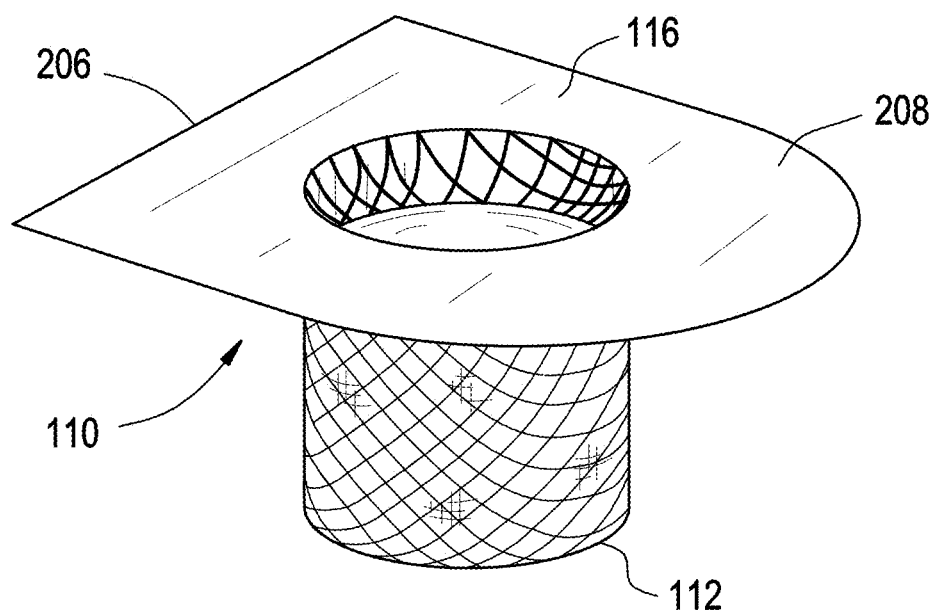

FIG. 47 is a perspective view of one embodiment showing the atrial cuff/collar wherein the shape is onychoid.

Figure 48:
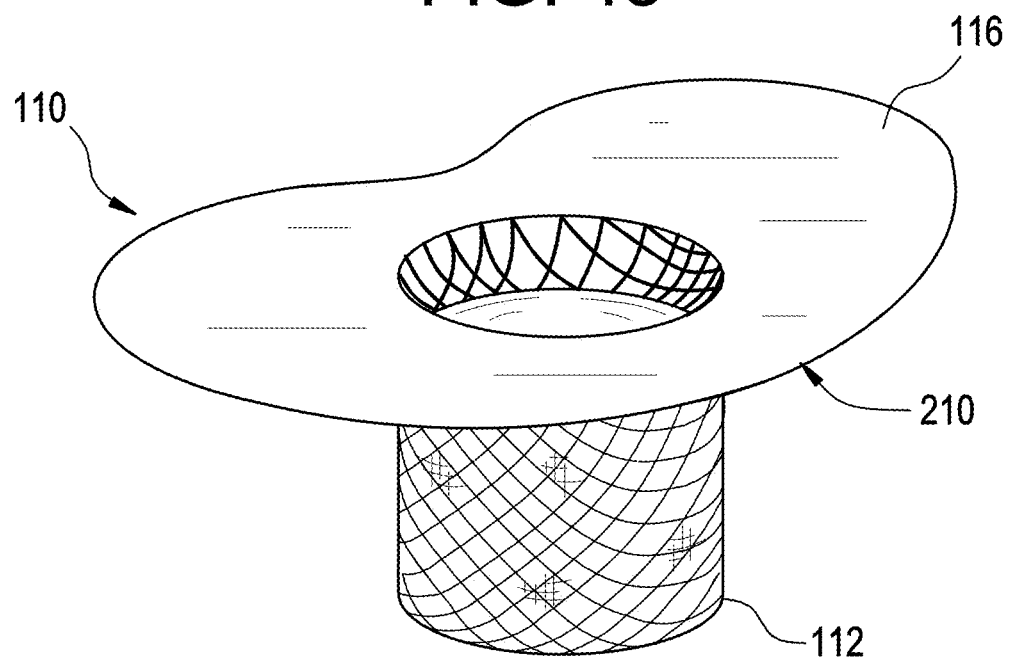

FIG. 48 is a perspective view of one embodiment showing the atrial cuff/collar wherein the shape is reniform.

Figure 49:
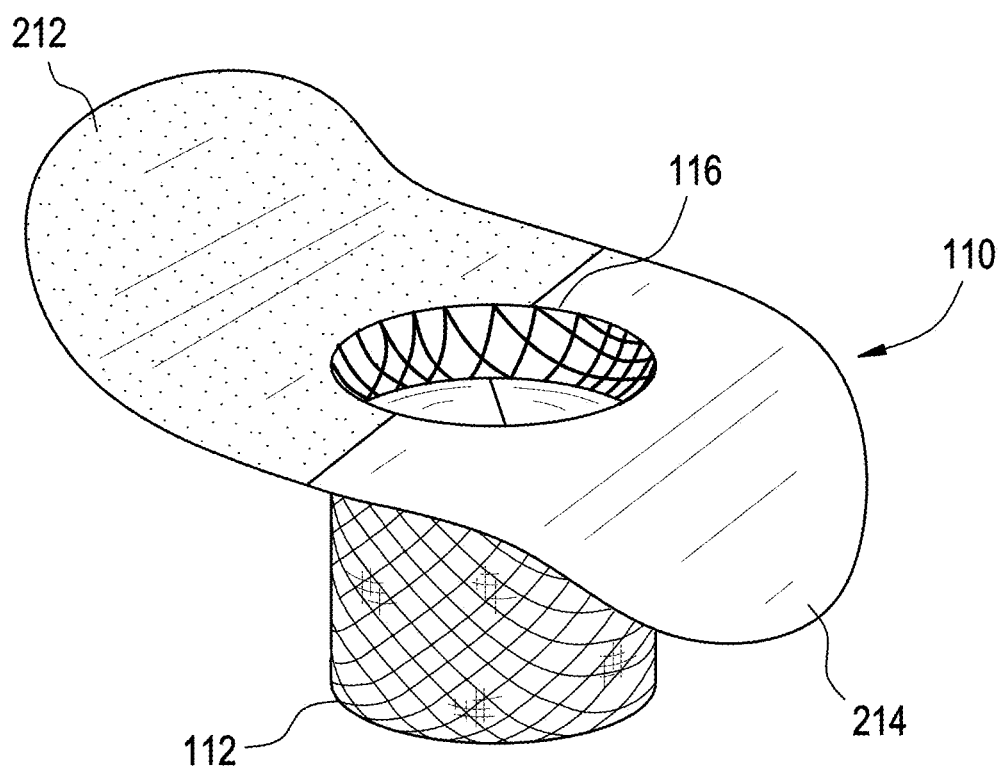

FIG. 49 is a perspective view of one embodiment showing the atrial cuff/collar wherein the shape is an oval.

Figure 50:
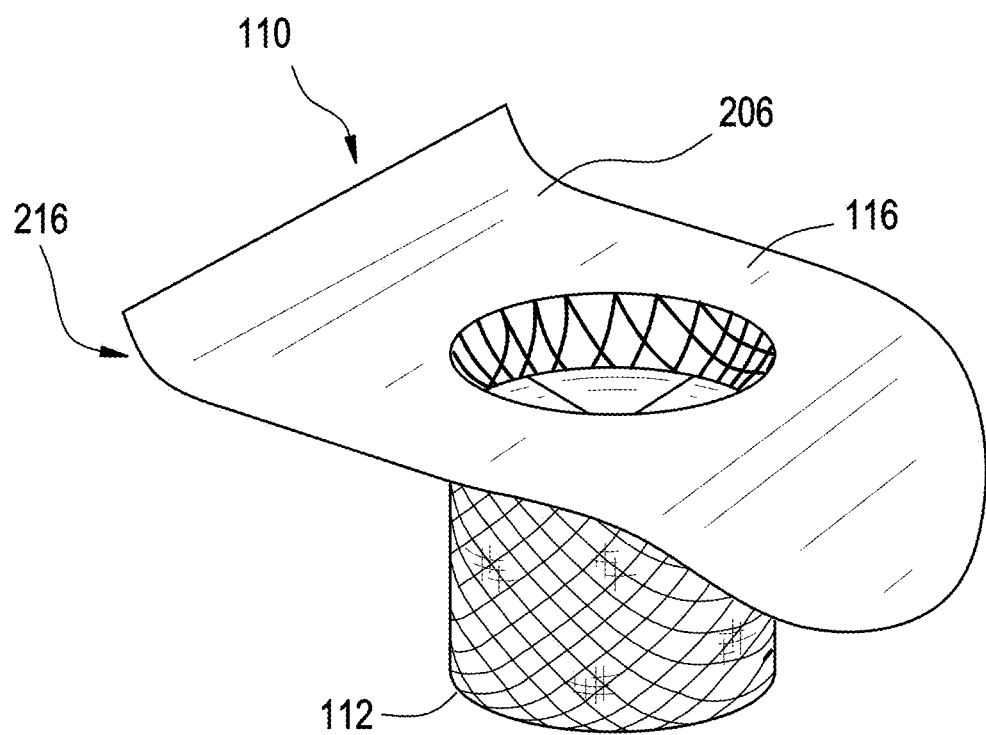

FIG. 50 is a perspective view of one embodiment showing the atrial cuff/collar wherein the shape is a truncated-oval having a squared end.

Figure 51:
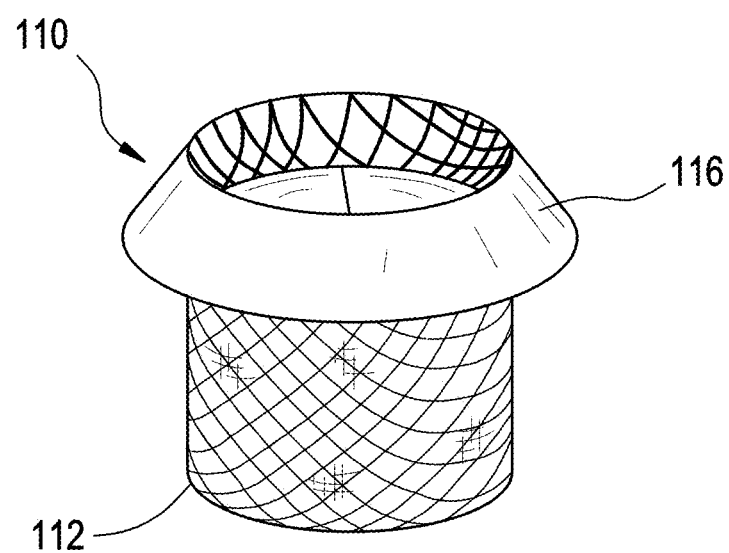

FIG. 51 is a perspective view of one embodiment showing the atrial cuff/collar as an acute angle sealing structure.

Figure 52:
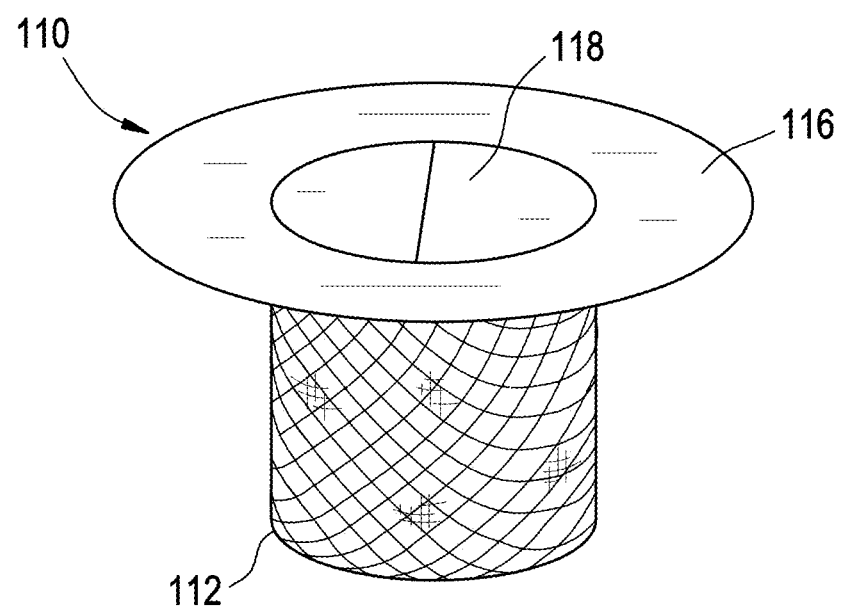

FIG. 52 is a perspective view of one embodiment showing the atrial cuff/collar and the internal valve leaflets at nearly that same planar location/height.

Figure 53:
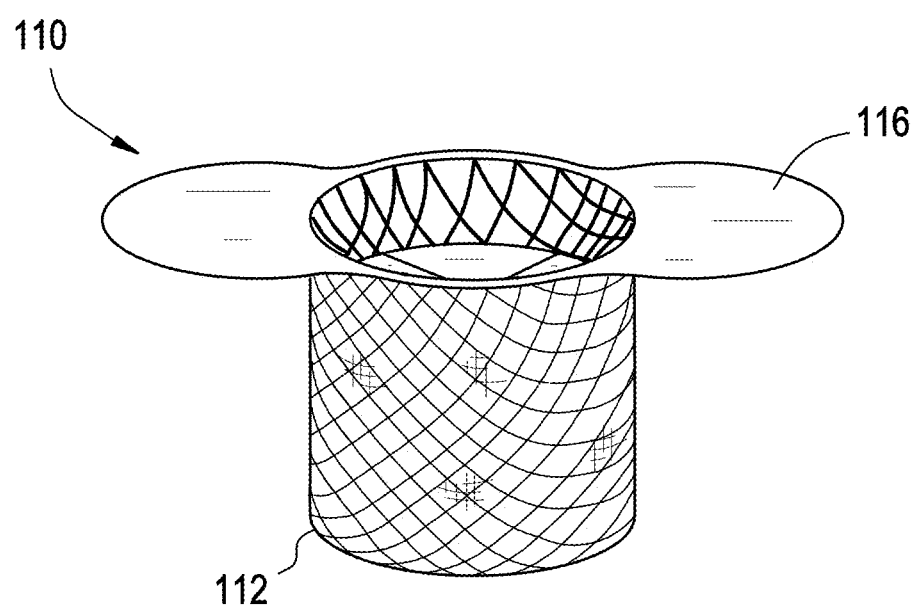

FIG. 53 is a perspective view of one embodiment showing the atrial cuff/collar wherein the shape is propeller-shaped.

Figure 54:
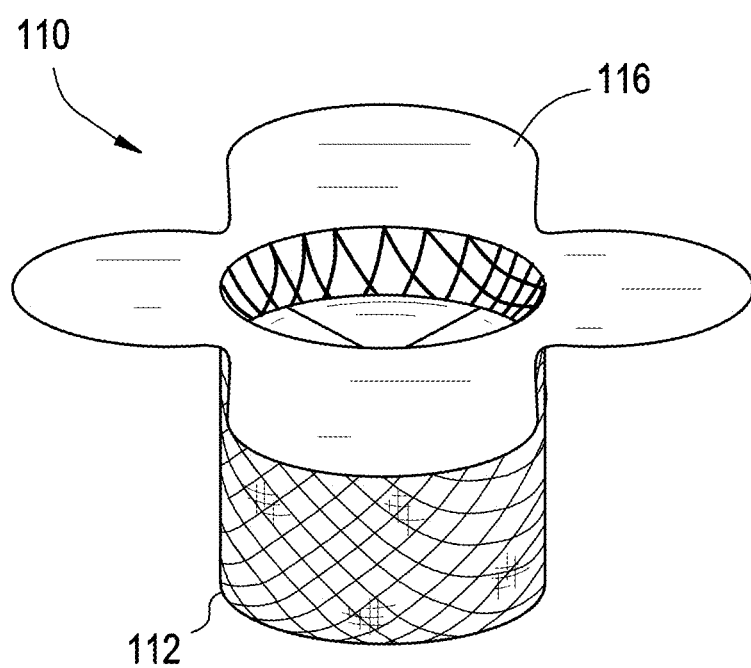

FIG. 54 is a perspective view of one embodiment showing the atrial cuff/collar wherein the shape is is cruciform.

Figure 55:
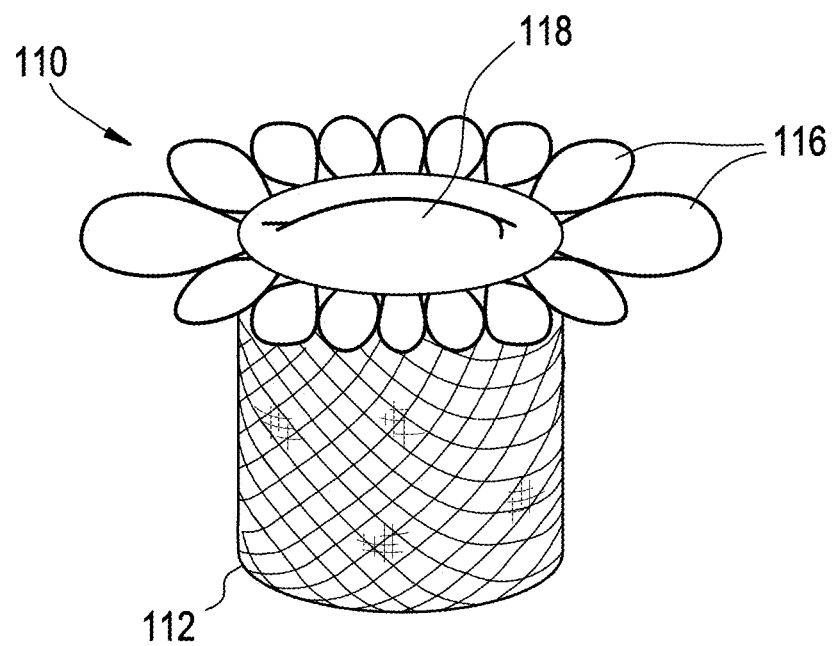

FIG. 55 is a perspective view of one embodiment showing the atrial cuff/collar wherein the shape is petal-shaped having flat radial covered loops.

Figure 56:
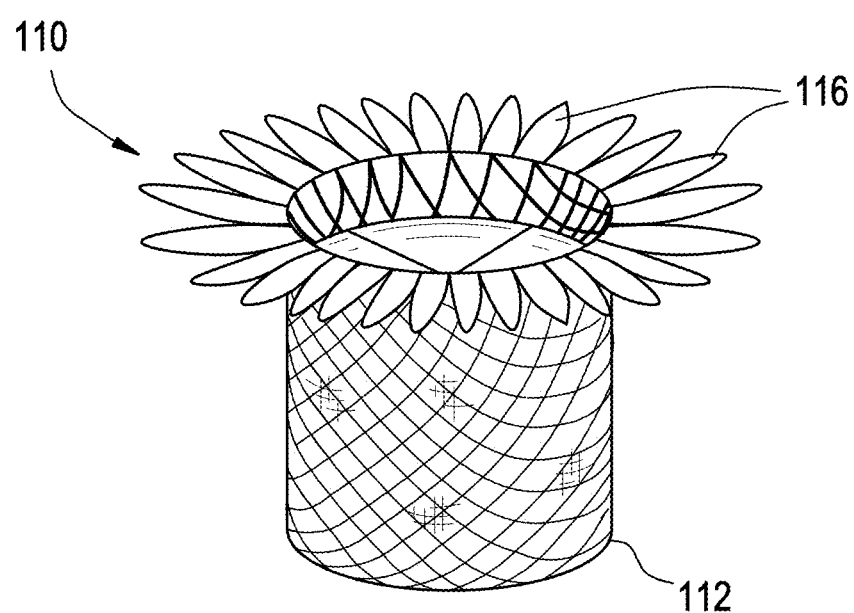

FIG. 56 is a perspective view of one embodiment showing the atrial cuff/collar wherein the shape is petal-shaped having flat radial covered stellate loops.

Figure 57:
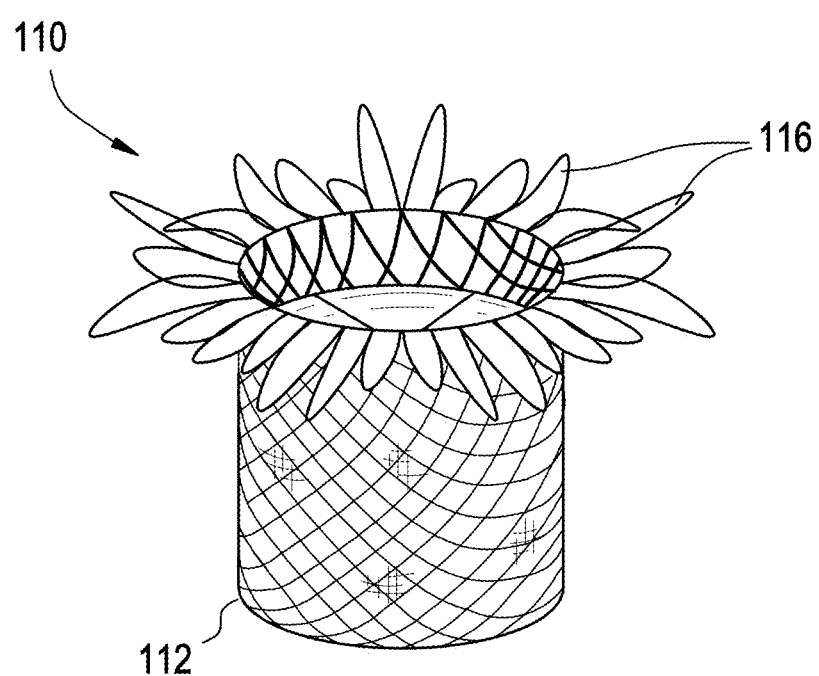

FIG. 57 is a perspective view of one embodiment showing the atrial cuff/collar wherein the shape is petal-shaped having flat radial covered stellate loops illustrating how they can travel longitudinally to effectuate sealing.

Figure 58:
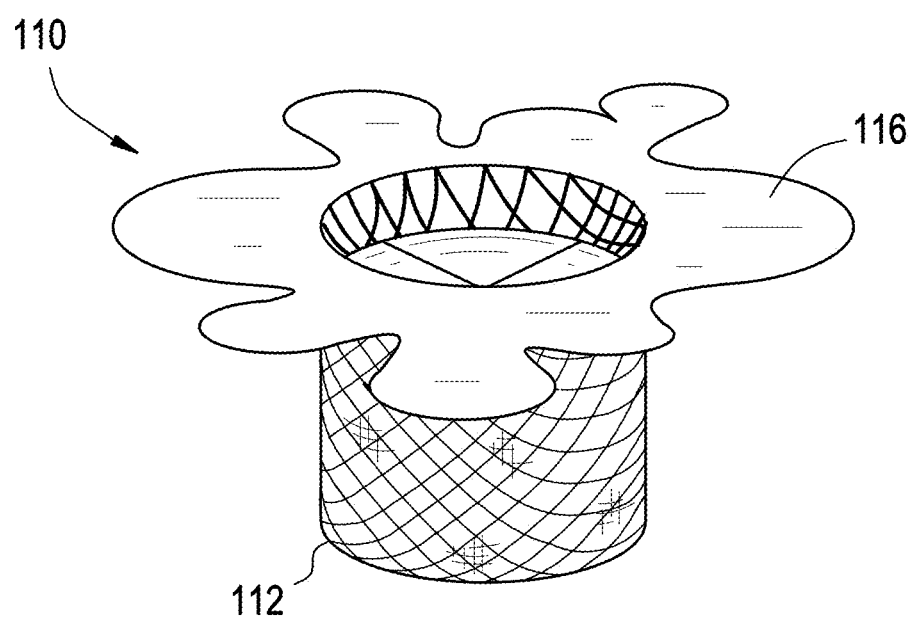

FIG. 58 is a perspective view of one embodiment showing the atrial cuff/collar wherein the shape is is irregular or amoeboid.

Figure 59:
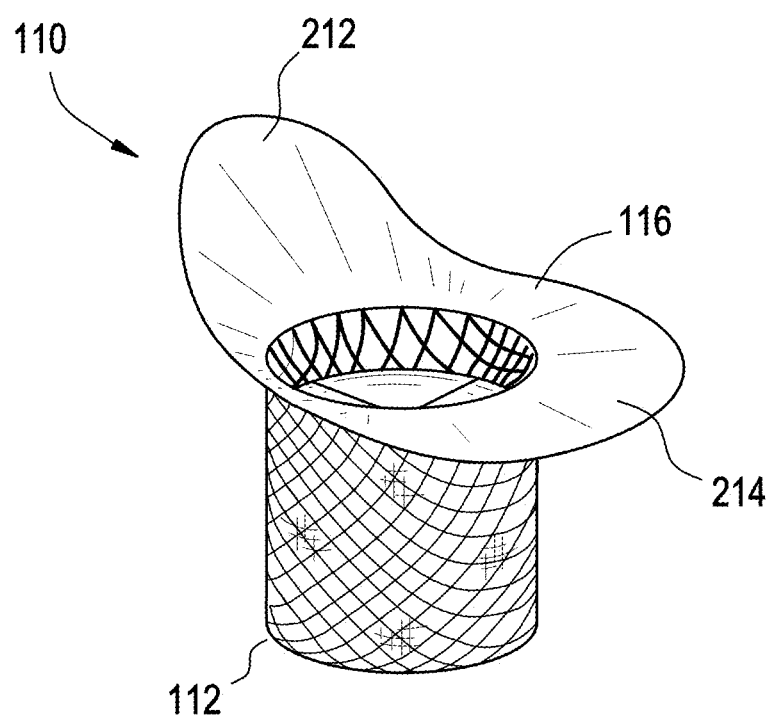

FIG. 59 is a perspective view of one embodiment showing the atrial cuff/collar wherein the shape is cotyloid shaped.

Figure 60:
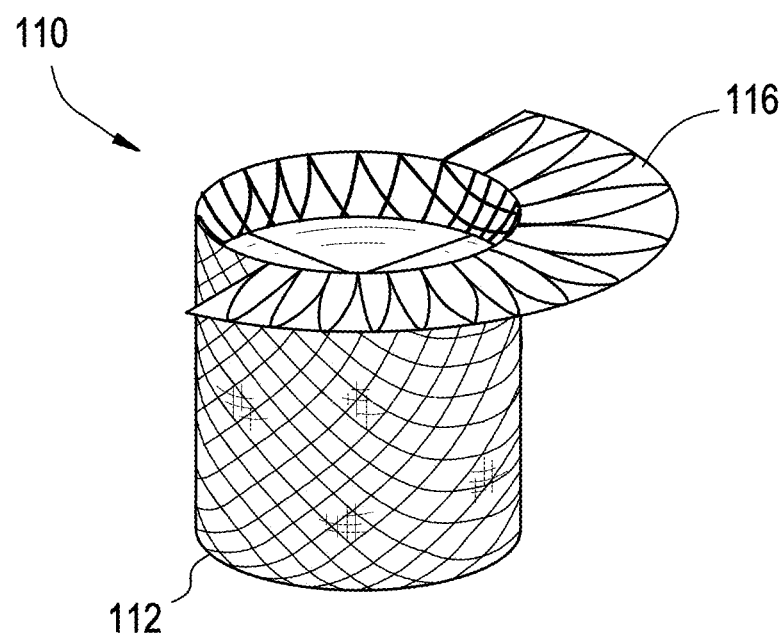

FIG. 60 is a perspective view of one embodiment showing the atrial cuff/collar wherein the shape is a partial half-round fan-shape.

FIG. 61 is a perspective view of one embodiment showing the atrial cuff/collar wherein the shape is a upturned rectangular U-shape.

Figure 62A:
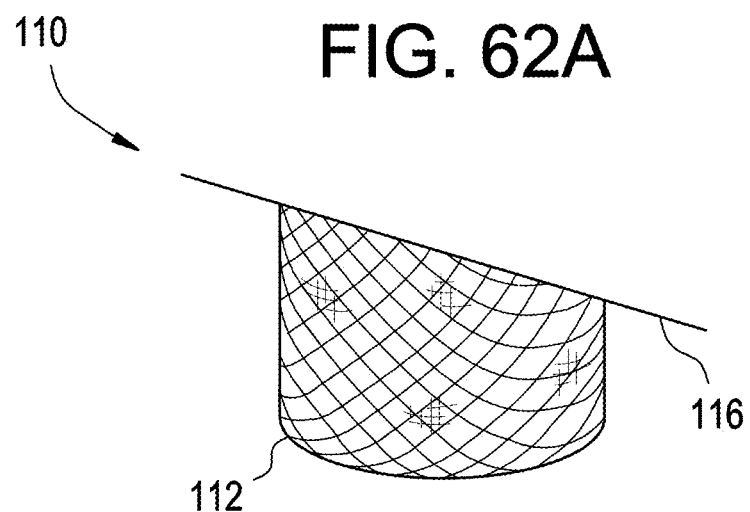
Figure 62B:
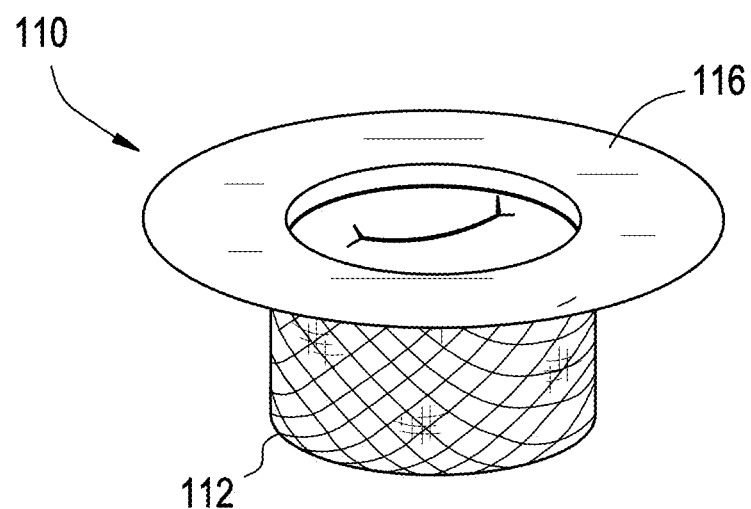

FIG. 62A is a side view and FIG. 62B is a front perspective view of one embodiment showing the atrial cuff/collar attached to the stent body at a forward angle, posterior to anterior.

Improved Stent Designs

Figure 63A:
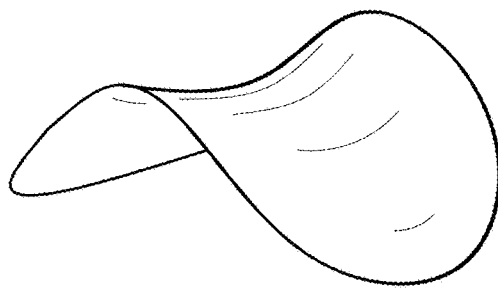

FIG. 63A is a perspective view of the saddle shape of a native mitral valve leaflet structure or of a prosthetic valve leaflet structure according to the present invention.

Figure 63B:
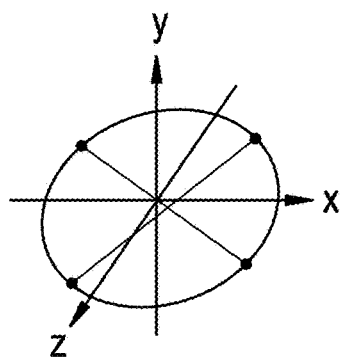

FIG. 63B is a drawing of the three-dimensional relative position of the mitral valve compared to the X-Y-Z axis.

Figure 63C:
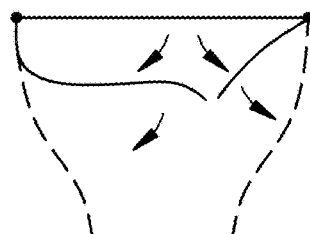

FIG. 63C is a drawing of a side view representation of a mitral valve showing the range of movement of the anterior and posterior leaflets from closed to opened.

Figure 63D:
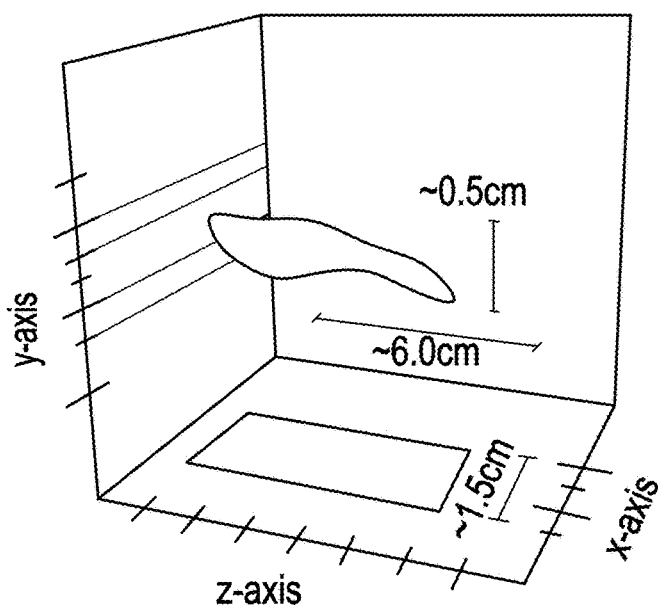

FIG. 63D is a graphical three-dimensional representation of a mitral valve with approximate orientation and sizes in all three dimensions.

Figure 64:
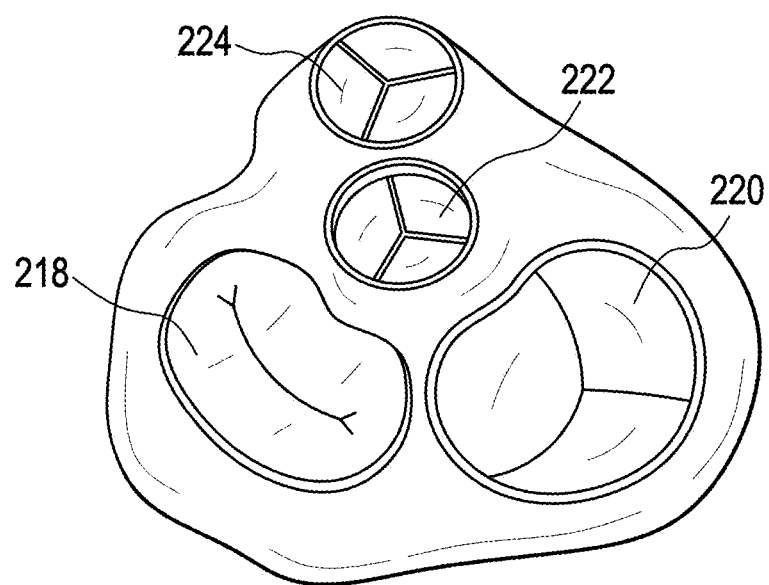

FIG. 64 is a drawing of the heart in cross-section showing the positional relationship of the mitral and tricuspid valves to the pulmonic and aortic arteries.

Figure 65A:
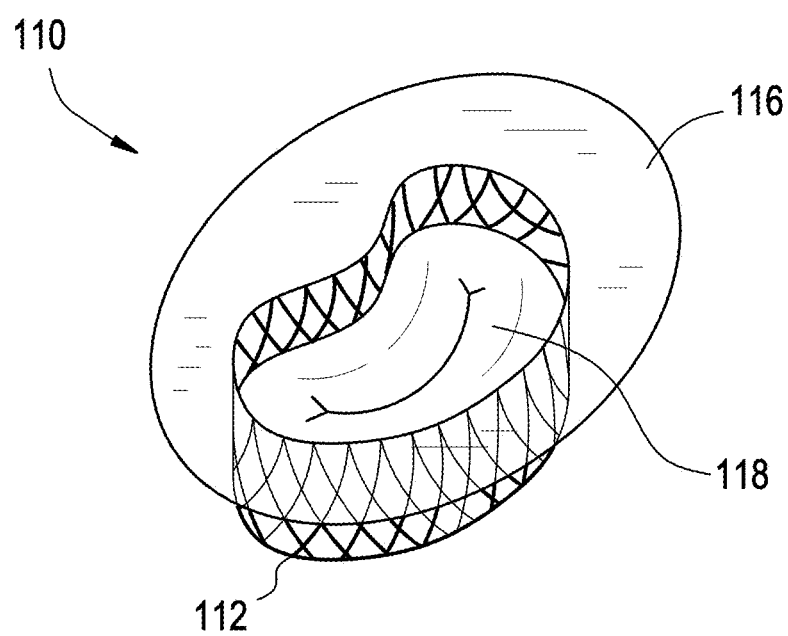

FIG. 65A is a perspective drawing of one embodiment according to the present invention showing a prosthetic mitral valve having a kidney-shaped stent conformation in cross-section with an atrial cuff, shown here as opaque for stent detail.

Figure 65B:
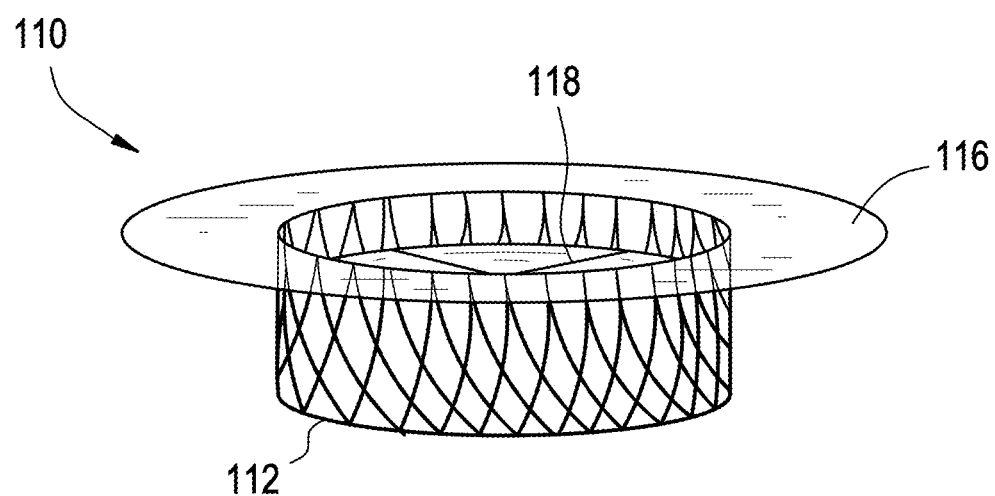

FIG. 65B is a perspective drawing of one embodiment according to the present invention illustrating a prosthetic mitral valve having a rounded-shape stent or oval-shape stent conformation in cross-section with valve leaflets positioned towards the middle-point halfway up within the stent body, and with an atrial cuff, shown here as opaque for stent detail.

Figure 66:
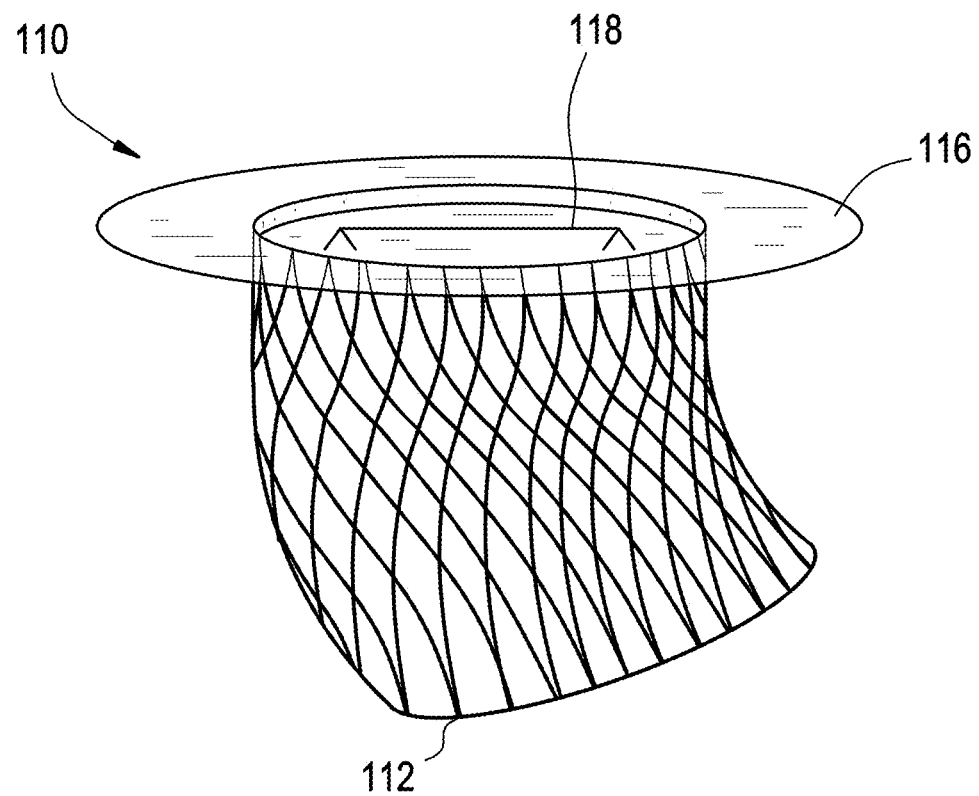

FIG. 66 is a perspective drawing of one embodiment according to the present invention showing a prosthetic mitral valve having a curved-tubular shape stent conformation in cross-section with an atrial cuff, shown here as opaque for stent detail.

Figure 67:
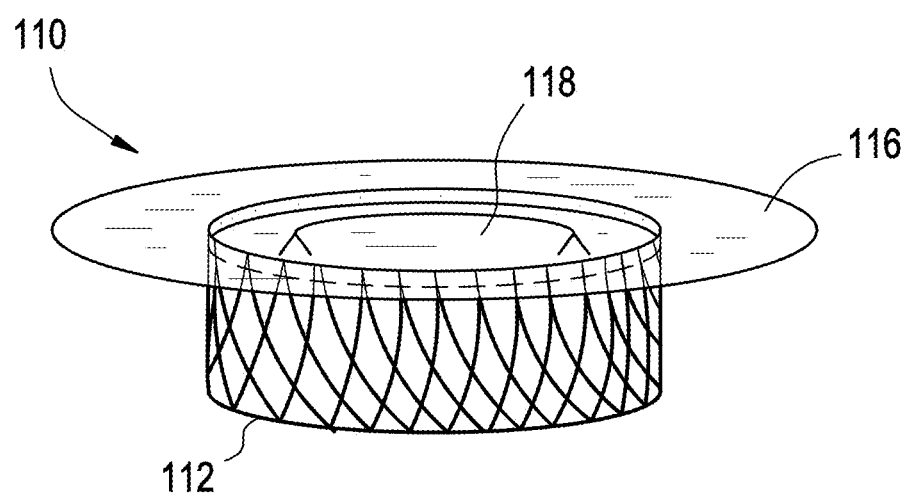

FIG. 67 is a perspective drawing of one embodiment according to the present invention showing a prosthetic mitral valve having a rounded-shape stent or oval-shape stent conformation in cross-section with valve leaflets positioned high in the stent toward the atrial end of the stent body, and an atrial cuff, shown here as opaque for stent detail.

Figure 68:
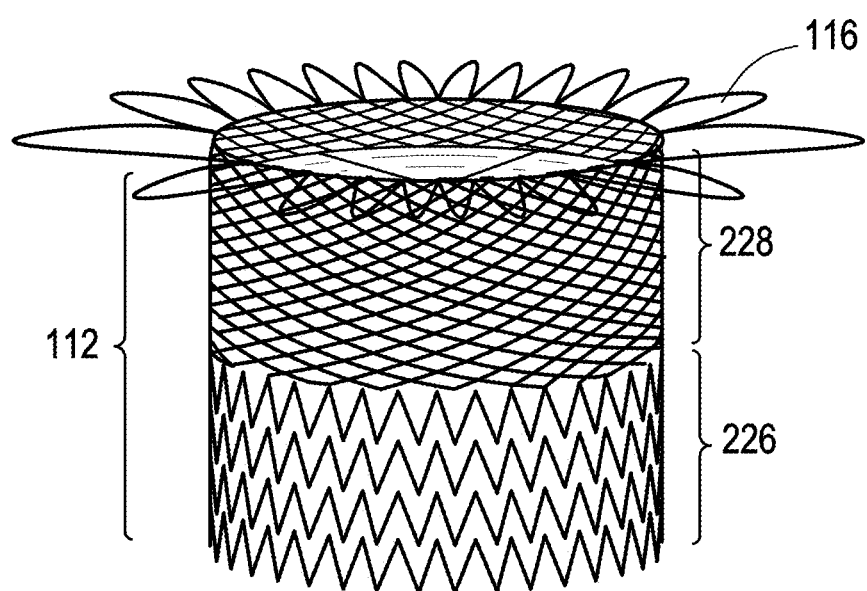

FIG. 68 is a perspective drawing of one embodiment according to the present invention showing a prosthetic mitral valve having a stent body made from both braided wire (atrial end) and laser-cut metal (annular or ventricular end), and an uncovered atrial cuff.

Figure 69:
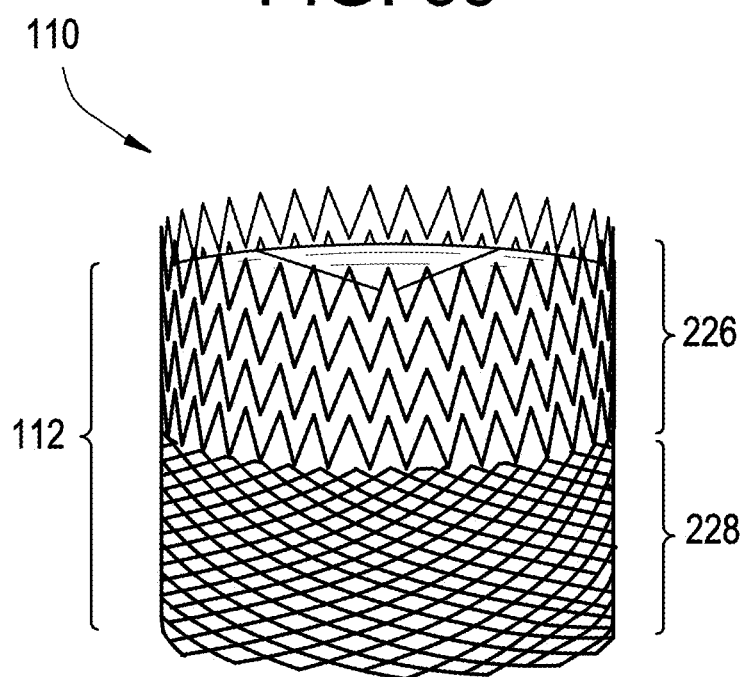

FIG. 69 is a perspective drawing of one embodiment according to the present invention showing a prosthetic mitral valve having a stent body made from both laser-cut metal (atrial end) and braided wire (annular or ventricular end), and without an atrial cuff.

Narrow Gauge Stent

Figure 70:
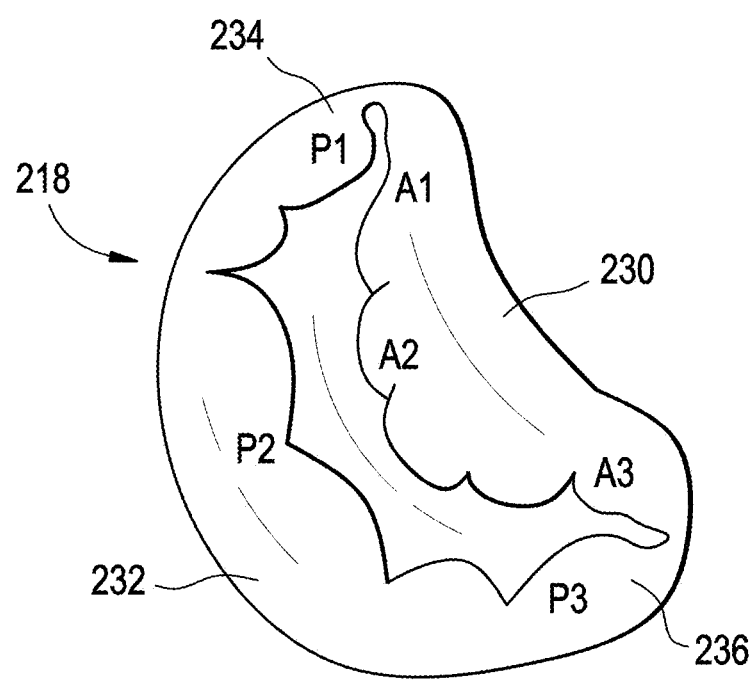

FIG. 70 is a line drawing showing a native mitral valve without implant.

Figure 71:
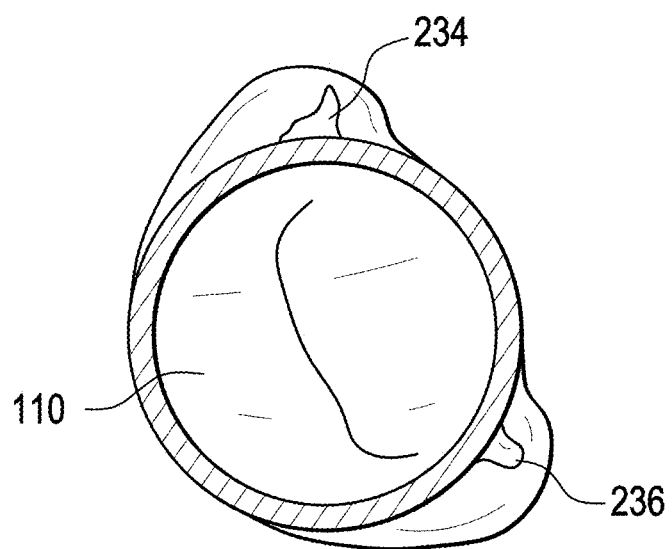

FIG. 71 is a line drawing showing an implanted full-sized prosthetic causing commissural stretching.

Figure 72:
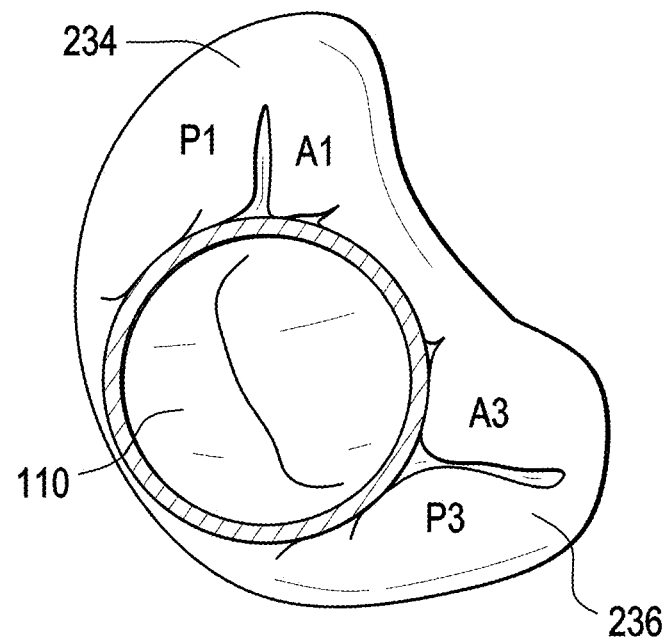

FIG. 72 is a line drawing showing a prosthetic mitral valve sized to avoid interaction with or deformation of the commissures being used to treat mitral regurgitation at the central jet.

Figure 73:
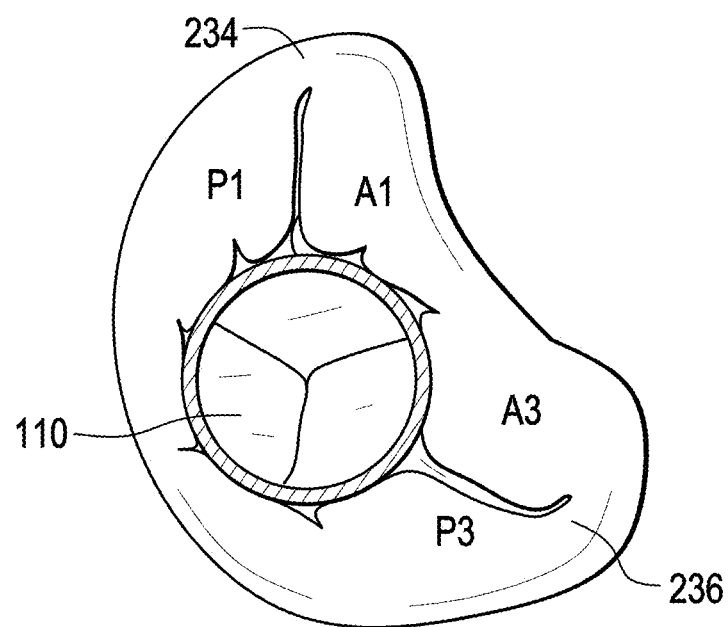

FIG. 73 is a line drawing showing a narrow diameter prosthetic body seated within a valve.

Figure 74:
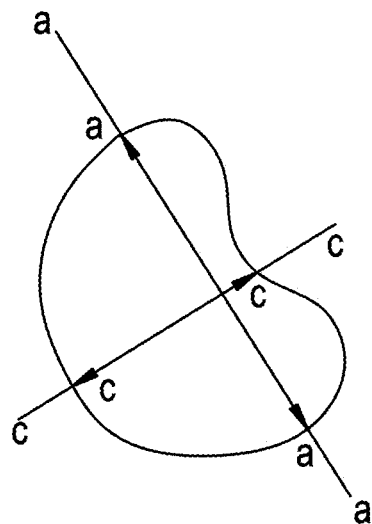

FIG. 74 is a line drawing showing how the hyperbolic paraboloid shape of the native mitral valve yields different diameters, whether posterior to anterior, or longitudinal along the line of the cusp interface.

Figure 75:
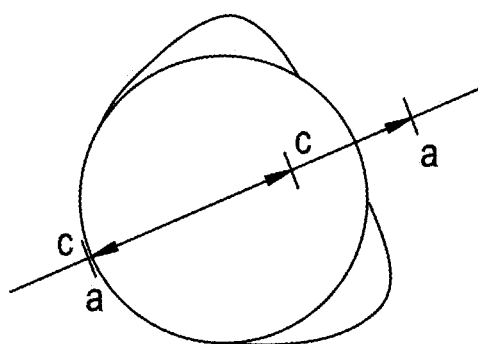

FIG. 75 is a line drawing showing how an over-large valve extends beyond line c-c, and could, if the longest diameter were inadvertantly used, the full diameter of the native annulus line a-a, that it extends even further beyond what is believed to be too large of a valve diameter (in some situations).

Figure 76:
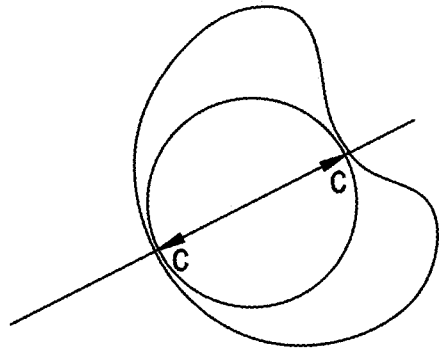
Figure 77:
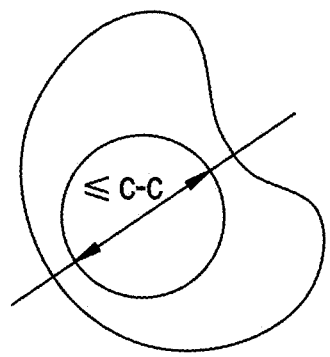

FIG. 76 and FIG. 77 are line drawings showing positive examples of the concept disclosed herein, where the diameter is either equal to or less than the cross-section diameter of the native annulus from posterior to anterior side.

Figure 78:
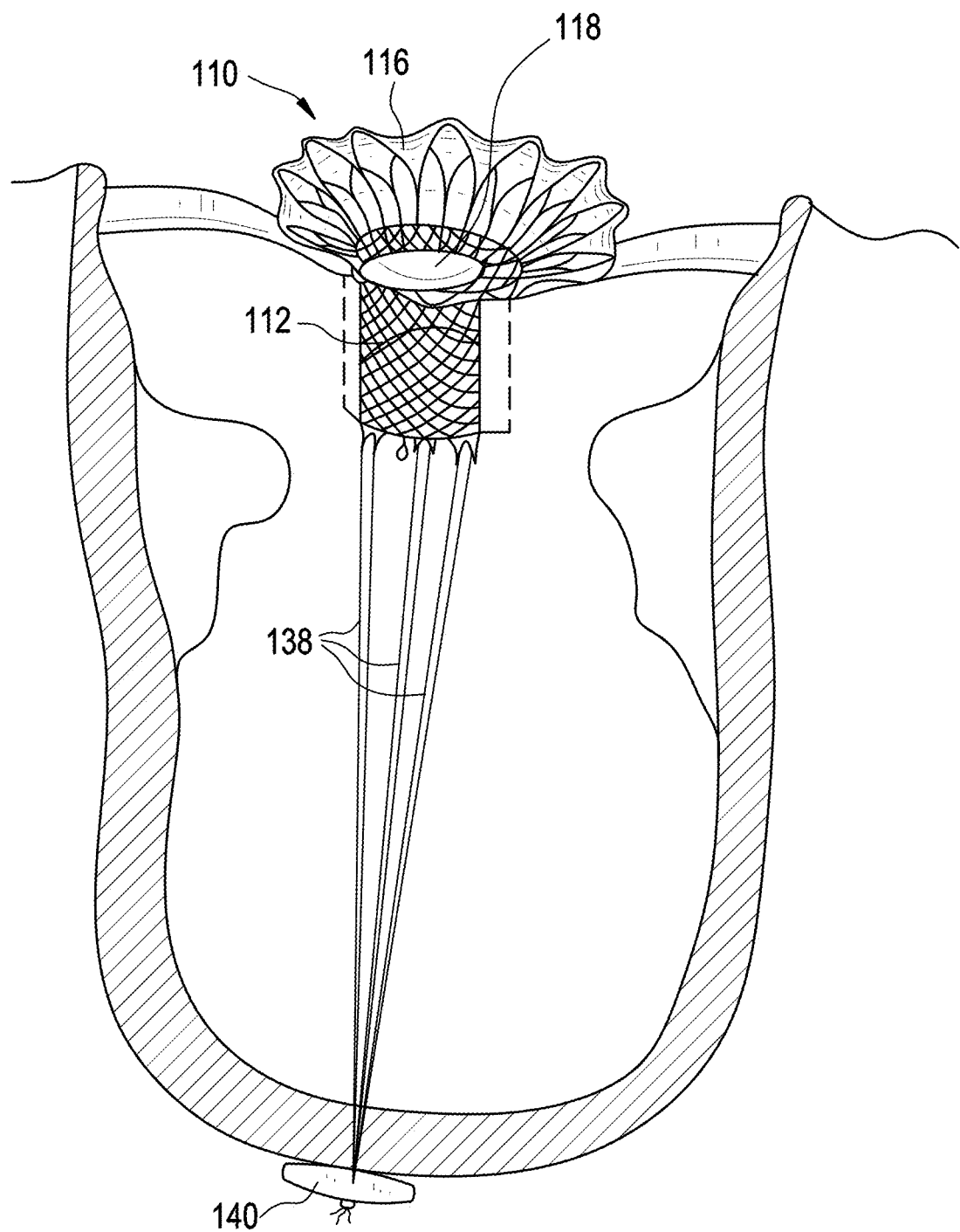

FIG. 78 is a line drawing showing an embodiment of the narrow valve wherein the dashed line illustrates the diameter of the native annulus and contrasts the narrow gauge stent seated within.

DETAILED DESCRIPTION OF THE INVENTION

The present invention provides various improvements in the design and components of prosthetic valves, especially for use in cardiac surgeries. Specifically, the invention relates to improved designs and features providing better stability, fit, durability and ease of delivery and retrieval for such prosthetic valves. For the purposes of this application, the terms "collar" and "sealing cuff" are used interchangeably.

Improved Surface Components

In one embodiment, the invention provides improvement in the surface components and structures for prosthetic valves intended to be deployed into a closed beating heart using a transcatheter delivery system. The combination of unique features herein addresses many of the issues and points of failure in current valve technology and provides a highly developed approach to the extraordinary number of problems that arise when attempting to provide a medical device of this type. The invention provides improved ingrowth of the prosthetic, maintains structural integrity over large cycles, addresses biocompatibility issues, and addresses hemocompatibility issues. Additionally, the invention addresses problems related to unwanted buckling of the surface material, lack of sealing of the prosthetic valve within the valvular annulus, unwanted twisting of fabrics, and difficulties arising from elasticity during attachment of the cover to the stent.

In a preferred embodiment, there is provided a multi-layer cover for a prosthetic heart valve having an expandable tubular stent and an expandable internal leaflet assembly, wherein said stent is a tubular wire-form having an interior wall and an exterior wall, and wherein said leaflet assembly is disposed within the stent to form a valve and is comprised of stabilized tissue or synthetic material, wherein the multi-layer cover comprises at least two layers of stabilized tissue or synthetic material, a first layer comprised of a polyester material and a second layer comprised of a polyester material or stabilized tissue, wherein the first layer is attached to the interior wall of the stent and the second layer is attached to the exterior wall of the stent.

Stabilized Tissue or Biocompatible Synthetic Material

In one embodiment, it is contemplated that multiple types of tissue and biocompatible material may be used to line or cover both the inner "interior" and/or outer "exterior" lateral walls of the stent, and to line or cover embodiments utilizing the integral sealing cuff. As stated previously, the leaflet component may be constructed solely from stabilized tissue or synthetic material, with or without using an additional wire support, to create a leaflet assembly and valve leaflets. In this aspect, the leaflet component may be attached to the stent with or without the use of the wire form.

It is contemplated that the tissue may be used to cover the inside of the stent body, but that the outside of the stent body is lined or covered with either tissue or synthetic material. Where the stent is heat formed to created a sealing cuff structure, the top "side" of the cuff wire form (formerly the interior until the stent was heat formed) will be lined with tissue, whereas the underside of the sealing cuff will be lined, similar to the exterior, with tissue or more preferably synthetic material In one preferred embodiment, the tissue used herein is optionally a biological tissue and may be a chemically stabilized valve of an animal, such as a pig. In another preferred embodiment, the biological tissue is used to make leaflets that are sewn or attached to a metal frame. This tissue is chemically stabilized pericardial tissue of an animal, such as a cow (bovine pericardium) or sheep (ovine pericardium) or pig (porcine pericardium) or horse (equine pericardium).

Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses acellular collagen-based tissue matrix for transplantation.

In one preferred embodiment, the synthetic material is a polyurethane or polytetrafluoroethylene. The synthetic polymer materials include expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

In another embodiment, the tissue and/or synthetic material liner/cover may optionally have a surface that has been treated with (or reacted with) an anti-coagulant, such as, without limitation, immobilized heparin. Such currently available heparinized polymers are known and available to a person of ordinary skill in the art.

Layers

In one preferred embodiment, the layering of the stent and the synthetic material and tissue may be provided in various options. For example, in one preferred embodiment, it is contemplated that the interior layer (within the lumen of the stent) is Dacron® (aka PET), and the outer exterior of the stent is lined or covered with stabilized tissue as described herein. In another embodiment, there is Dacron® both on the interior and the exterior of the stent, where one or both may be electrospun PET to provide the microscopic 'hairs' necessary for in-growth. In another embodiment, the prosthetic valve may have a synthetic layer on top of a tissue layer for an exterior, and have a tissue layer on the interior.

Electrospun Fibers

Electrospinning is a technology that produces polymer fibers with diameters ranging from the nano- to the microscale. Fabrics with complex shapes can be electrospun from solutions, producing a broad range of fiber and fabric properties. Electrospinning produces materials with high surface to weight and volume ratios, which makes these materials excellent candidates for controlled biological interactions, especially construction of fibrous extra-cellular matrix scaffolds. The porous nature of the fabric coupled with the ability to spin many types of polymers allows for the formation of implantable structures. Here, the prosthetic valve cover material can use the electrospun fabric as a scaffolding to allow integration into the body, also known as in-growth or cell attachment (both endothelialization and smooth muscle cell attachment). Additives, ranging from therapeutic agents to property modifiers, can be introduced into the solutions and become incorporated into the fibers and fabrics.

In preferred embodiments, the synthetic material will range in thickness from about 0.001" (0.0254 mm) to about 0.015" (0.3809 mm), or from about 0.002" (0.0508 mm) to about 0.010" (0.254 mm), or alternatively wherein both the first layer and the second layer are about 0.005" (0.127 mm) in thickness. Preferred materials may be obtained from Zeus Co., Orangeburg, S.C.

By creating a sandwiched prosthetic valve made using a nitinol (or similar) stent that has extremely thin tissue on the inside and extremely thin synthetic, e.g. Dacron®, on the outside, very small but very durable prosthetic valves can be created and, importantly, delivered via the less-invasive, safer transcatheter delivery techniques.

Synthetics and polymers contemplated as within the scope of the present invention support long-term cell growth, without cytotoxic or mutagenic effects, and have a degradation profile consistant with its usage. For example, the material should promote in-growth but not degrade prior to effective in-growth, where the rate of degradation matches the rate of tissue attachment. Also, degradation by-products must be similarly non-toxic and biocompatible.

Biodegradable materials contemplated as within the scope of the present invention include without limitation polyesters such as polylactide (PLA), polyglycolide (PGA), polycaprolactone (PCL), polylactide-co-polyglycolide (PLGA), co-polymers of poly-L-lactide and polycaprolactone (PLLA-CL), and poly-3-hydroxybutyrate-co-3-hydroxyvalerate (PHBV). Also contemplated as within the scope of the invention are polyanhydrides, polyamides, modified polysaccharides, polyalkene glycols (e.g. PEG), polyalkene oxides (e.g. PEO, PEO-co-PBT), and polyalkene terephthalates (e.g. PBT), and ethylene-vinyl acetate co-polymers.

However, non-degradable polymers may also be used but with biocompatible coatings in order to reduce problems known in the art that arise with the use of certain polymers such as immune responses, thrombotic responses, and cell toxicity. include non-degradable materials such as polytetrafluoroehtylene (PTFE), polyethylene-co-vinyl acetate, poly n-butyl methacrylate, poly(styrene-b-isobutylene-b-styrene, The co-polymers may vary in the range of the ratio of one polymer to the co-polymer from a ratio of about 5:95 to a ratio of about 95:5. In certain embodiments, the ratio range may be about 10:90 to about 90:10, or range from about 20:80 to 80:20, or from about 25:75 to 75:25, or from about 30:70 to 70:30, or 40:60 to 60:40, or 50:50, or subranges in between.

In a preferred non-limiting embodiment, the material is spun into nanofibers, fibers having a cross-sectional size of less than 1000 nm. Preferred diameters may range from about 100 to about 1000 nm. Alternative preferred embodiments include nanofibers having a diameter ranging from about 200-800, or alternatively about 300-800 nm.

Additional therapeutic agents, e.g. sirolimus, paclitaxel, may be used incorporated into the polymer in certain embodiments for local, timed release.

Fabrication of Electrospun Nanofibers

To fabricate polymeric nanofibers by electrospinning, the polymer was dissolved in an appropriate solvent. The resultant solution was then filled in a syringe. With the aid of a syringe pump, the solution was ejected out through a needle tip with an inner diameter of 0.21 mm at a constant feed-rate. A high DC voltage ranging from 10-15 kV (Gamma High Voltage Research, Ormond Beach, Fla., USA) was applied between the needle and a grounded aluminum plate which was 15 cm below the needle.

The electric field generated by the surface charge causes the solution drop at the tip of the needle to distort into the Taylor cone. Once the electric potential at the surface charge exceeded a critical value, the electrostatic forces overcome the solution surface tension and a thin jet of solution erupts from the surface of the cone. The parameters for fabrication of nano-fibers include voltages from about 10-12.5 kV, solvents selected from hexafluoro-isopropanol, dimethylformamide, chloroform, methanol, dichloromethane, other solvents known to person of skill in the polymer arts, and mixtures and combination thereof.

Manufacture of Ultra-thin Stabilized Tissue

In a preferred embodiment, ultra-thin vapor-cross linked stabilized bioprosthetic or implant tissue material is contemplated. Tissue having a 0.003' (0.0762 mm) to about 0.010" (0.254 mm) may be made using a process comprising the steps of: (a) vapor cross-linking a pre-digested compressed tissue specimen by exposing the tissue specimen to a vapor of a cross-linking agent selected from the group consisting of aldehydes, epoxides, isocyanates, carbodiimides, isothiocyanates, glycidalethers, and acyl azides; and (b) chemically cross-linking the vapor-cross-linked tissue specimen by exposing the vapor-crosslinked tissue specimen to an aqueous crosslinking bath for a predetermined time, such crosslinking bath containing a liquid phase of a crosslinking agent selected from the group consisting of aldehydes, epoxides, isocyanates, carbodiimides, isothiocyanates, glycidalethers, and acyl azides. [para 15] Such tissue may be porcine, ovine, equine or bovine in origin and preferably the initial material is taken from a bovine animal 30 days old or less, although tissue from older animals is contemplated as within the scope of the invention. In one preferred embodiment, the tissue specimen is subjected to chemical dehydration/compression and mechanical compression before cross-linking.

Pre-digestion is provided by digesting a harvested, cleaned pericardial tissue in a solution containing a surfactant, such as 1% sodium laurel sulfate. The chemical dehydration/compression step comprises subjecting the tissue specimen to hyperosmotic salt solution. And, the mechanical compression may be performed by subjecting the tissue specimen to a roller apparatus capable of compressing the tissue specimen to a thickness ranging from about 0.003' (0.0762 mm) to about 0.010" (0.254 mm).

The animal collagen tissue specimen is then chemically cross-linked first by exposing the tissue to formaldehyde vapor for approximately 10 minutes, and second by immersing the tissue in a glutaraldehyde solution for two consecutive sessions of approximately 24 hours each.

Functions of the Annular Cuff/Collar

The valve collar functions in a variety of ways. The first function of the prosthetic valve is to be a substitute for the native valve, but with improved functions, such as inhibiting perivalvular leak/regurgitation of blood by flexing and sealing across the irregular contours of the annulus and atrium.

The second function of the valve collar is to provide adjustability and compliance once the prosthetic is seated.

The heart and its structures undergo complex conformational changes during the cardiac cycle. For example, the mitral valve annulus has a complex geometric shape known as a hyperbolic parabloid much like a saddle, with the horn being anterior, the seat back being posterior, and the left and right valleys located medially and laterally. Beyond this complexity, the area of the mitral annulus changes over the course of the cardiac cycle. Further, the geometry of the tricuspid valve and tricuspid annulus continues to be a topic of research, posing its own particular problems. Accordingly, compliance is a very important but unfortunately often overlooked requirement of cardiac devices. Compliance here refers to the ability of the valve to maintain structural position and integrity during the cardiac cycle. Compliance with the motion of the heart is a particularly important feature, especially the ability to provide localized compliance where the underlying surfaces are acting differently from the adjacent surfaces. This ability to vary throughout the cardiac cycle allows the valve to remain seated and properly deployed in a manner not heretofore provided.

Additionally, compliance may be achieved through the use of the tethers where the tethers are preferably made from an elastic material. Tether-based compliance may be used alone, or in combination with the collar-based compliance.

The third function of the valve/collar is to provide a valve that, during surgery, is able to be seated and be able to contour to the irregular surfaces of the atrium. The use of independent tethers allows for side to side fitting of the valve within the annulus. For example, where three tethers are used, they are located circumferentially about 120 degrees relative to each other which allows the surgeon to observe whether or where perivalvular leaking might be occurring and to pull on one side or the other to create localized pressure and reduce or eliminate the leaking.

The forth function of the collar is to counter the forces that act to displace the prosthesis toward/into the ventricle (i.e. atrial pressure and flow-generated shear stress) during ventricular filling.

Additional features of the collar include that it functions to strengthen the leaflet assembly/stent combination by providing additional structure. Further, during deployment, the collar functions to guide the entire structure, the prosthetic valve, into place at the mitral annulus during deployment and to keep the valve in place once it is deployed.

Another very important feature in one embodiment of the present invention is that the design of the valve allows the leaflets to be located high within the stent body, in the top half (atrial) of the lumen of the stent, or even at or near the atrial top end of the stent portion of the prosthetic valve. By allowing the leaflets to be located high within the stent body, the reduces the occurrence of LVOT obstruction (Left Ventricular Outflow Tract obstruction), a situation where the blood leaving the left ventricle to the aortic valve is obstructed and/or has it's laminar flow disrupted. In some circumstances this pathological condition is caused by having a stent or other medical device at or near the mitral valve area that extends too far into the left ventricle itself.

Annular Cuff/Collar Structure

The collar is a substantially flat, circular, band-shaped collar structure that is attached to and encircles the tubular stent forming a V-shape, when viewed in cross-section, between the exterior wall of the tubular stent and the flat, circular band-shaped annular expansion gasket. The stiff-yet-flexible nature of the attached (or integrated) gasket in a V-shape collar establishes a "cork" or "shuttlecock" type of structure that when the prosthetic valve is deployed into the annulus of the valve, e.g. mitral valve, the wedge-ring shape of the device, with its spring-like pusher band to provide a lateral annular compressive pressure or force against the native valve annulus to immobilize the valve and provide a seal between the cardiac chambers, e.g. the atrium and the ventricular, to re-establish valve function via the prosthetic valve. As viewed from a side perspective, the collar diameter matches the diameter of the tubular stent where the collar is attached to the stent nearest the ventricle, but as the collar and stent wall form a V-shape, the diameter of the collar gets larger and larger, until it reaches it's maximum diameter at the atrial terminus of the collar panel. As used herein, the term collar, inverted flange, gasket, spring panel, are considered to be functionally equivalent. When the tubular stent is pulled through the mitral valve aperture, the mitral annulus, by the tether loops in the direction of the left ventricle, the flexible collar acts as to stop the tubular stent from traveling any further through the mitral valve aperture. At this point, the entire prosthetic valve is held by lateral pressure caused by the forcible compression of the advancing spring-like collar through the mitral annulus, and the longitudinal forces ventricular tethers attached to the left ventricle.

The collar is preferably formed from a web of polyester fabric spanning from the distal end of the stent body to a support structure made from superelastic metal. Alternatively, the web made be made from a stiff, flexible shape-memory material such as the nickel-titanium alloy material Nitinol® wire that is covered by stabilized tissue or other suitable biocompatible or synthetic material.

In one embodiment, the collar wire form is constructed from independent loops of wire creating lobes or segments extending axially around the circumference of the bend or seam where the collar transitions to the tubular stent (in an integral collar) or where the collar is attached to the stent (where they are separate, but joined components). The collar forms an acute angle in relation to the exterior wall of the tubular stent body.

In another embodiment, the collar is constructed from an attached panel. In this embodiment, the panel may be a solid metal band, or may be perforated, woven, or laser cut to provide a mesh-like surface, or may be a polyester fabric material.

Because of the material's flexibility, the collar has the ability to articulate back and forth, along the lateral axis compared to the longitudinal axis that runs length-wise through the center of the tubular stent. In other words, where the metal has loops or is woven, the individual spindles or loops can independently move back and forth, and can spring back to their original position due to the relative stiffness of the wire. The collar has a certain modulus of elasticity such that, when attached to the wire of the stent, is able to allow the collar to move. This flexibility gives the collar, upon being deployed within a patient's heart, the ability to conform to the anatomical shape necessary for a particular application. In the example of a prosthetic mitral valve, the collar is able to conform to the irregularities of the left atrium and shape of the mitral annulus, and to provide a tight seal against the atrial tissue adjacent the mitral annulus and the tissue within the mitral annulus. As stated previously, this feature importantly provides a degree of flexibility in sizing the a mitral valve and prevents blood from leaking around the implanted prosthetic heart valve.

In one preferred wire collar embodiment, the wire spindles of the collar are substantially uniform in shape and size. In another preferred embodiment of the present invention, each loop or spindle may be of varying shapes and sizes. In this example, it is contemplated that the loops may form a pattern of alternating large and small loops, depending on where the valve is being deployed. In the case of a prosthetic mitral valve, pre-operative imaging may allow for customizing the structure of the sealing cuff depending on a particular patient's anatomical geometry in the vicinity of the mitral annulus.

The sealing cuff wire form is constructed so as to provide sufficient structural integrity to withstand the intracardiac forces without collapsing. The sealing cuff wire form is preferably constructed of a web of polyester fabric spanning from the distal end of the stent body to a support structure made from a superelastic metal, such as Nitinol (TM)® and is capable of maintaining its function as a sealing collar for the tubular stent while under longitudinal forces that might cause a structural deformation or valve displacement. It is contemplated as within the scope of the invention to optionally use other shape memory alloys such as Cu—Zn—Al—Ni alloys, and Cu—Al—Ni alloys. The heart is known to generate an average left atrial pressure between about 8 and 30 mm Hg (about 0.15 to 0.6 psi). This left atrial filling pressure is the expected approximate pressure that would be exerted in the direction of the left ventricle when the prosthesis is open against the outer face of the collar as an anchoring force holding the collar against the mitral valve annulus. The collar counteracts this downward longitudinal pressure against the prosthesis in the direction of the left ventricle to keep the valve from being displaced or slipping into the ventricle. In contrast, left ventricular systolic pressure, normally about 120 mm Hg, exerts a force on the closed prosthesis in the direction of the left atrium. The tethers counteract this force and are used to maintain the valve position and withstand the ventricular force during ventricular contraction or systole. Accordingly, the collar has sufficient structural integrity to provide the necessary tension against the tethers without being dislodged and pulled into the left ventricle. Tethers and anchors may also be used to secure position against any other directional forces as necessary. After a period of time, changes in the geometry of the heart and/or fibrous adhesion between prosthesis and surrounding cardiac tissues may assist or replace the function of the ventricular tethers in resisting longitudinal forces on the valve prosthesis during ventricular contraction.

Annular Clamp Structure and Function

It is possible for a prosthetic valve stent to be stabilized within the valvular annulus through the use of integrated clamps located at intervals around the circumference of the stent. This clamp system may use clamps made of metal or similarly rigid and durable material, either as an integrated component of the stent during manufacture, by soldering, by threading stent wire through anchoring apertures in the clamp structure, or a similar attachment process.

In one embodiment of a clamp-based anchoring system, each clamp comprises a hinge made of a pin, optionally surrounded by a spring, said pin extending through holes in two interdigitated middle members, which hinge could be manipulated into a closed or open position. Further, each middle member of a clamp could comprise (a) a footer section with a proximal side and a distal side, (b) two flat plates with the distal end of each plate attached to the narrow edges of the proximal side of the footer section and extending out, parallel to each other, at a diagonal angle, (c) the proximal end of each plate containing a centered circular hole of a diameter to accommodate the insertion of the pin, and (d) a flat flange protruding from the center of the inner end of the footer section, with the flange containing a centered hole to allow connection by a tool to open and close the hinge. Attached to the distal end of each of the two middle members, two or more semicircular fingers, with an equal number of such fingers attached to each middle member such that, upon closing of the hinge, the open side of the semicircle faces inward and the closed side faces outward.

In this embodiment, the dual sets of semicircular fingers would move towards one another as the hinge closes and away from one another as the hinge opens. The semicircular fingers are attached to the middle members in a staggered fashion such that the semicircular members interdigitate upon closing. Finally, the tip of each semicircular finger tapers to form a point capable of piercing valve annulus tissue, allowing for a firm stabilizing anchor for both the stent and the valve it contains.

In a more preferred embodiment, the clamp assembly described above shall be manufactured similar to the dimensions indicated in FIGS. 37A-37F.

The clamp of the immediately preceding embodiment may be comprised within a clamp-based valve anchoring system in which two flexible members, each with a preformed bend and protruding from a delivery housing, wherein each such flexible member is attached to the flange of each middle member, such that the flexible member is straightened upon retraction into the delivery housing, and the action of straightening the flexible member applies pressure to the two flanges, closing the hinge.

In another preferred embodiment, the clamp body would comprise a hinge made of a pin, optionally surrounded by a spring, said pin extending through holes in the proximal ends of each of two or more closing members, which hinge can be manipulated into a closed or open position. The closing members each have a straight base branching outward into a semicircular shape so that, upon closing the hinge, the open side of the semicircle faces inward and the closed side faces outward.

Each closing member, or set of two or more closing members, will move parallel to one another in opposite directions, towards one another as the hinge closes and away from one another as the hinge opens. Thus, an open clamp can be positioned so that one or more closing members are located on either side of the native valve annulus tissue, and the tips will contact the annulus tissue upon the clamp being moved to a closed position.

Further, the closing members are attached to the pin in a staggered fashion such that the semicircular members interdigitate upon closing; and the tip of each closing member tapers to form a point capable of piercing the valve annulus tissue, again allowing for a firm stabilizing anchor for both the stent and the valve it contains.

In a more preferred embodiment, the clamp assembly described above shall be manufactured similar to the dimensions indicated in FIGS. 37A-37F.

Any of the clamps or other anchoring elements, or pressure-bearing members, described herein may be comprised of any surgically acceptable metal, natural or synthetic polymer or ceramic material, including but not limited to shape-memory alloys. The tapered tips of anchoring elements may also include further anchoring features, including but not limited to fishhook or arrowhead designs, with or without retraction capabilities for ease in withdrawing the anchors from tissue.

Functions of the Improved Annular Cuff/Collar

The atrial cuff or collar functions in a variety of ways. The first function of the atrial cuff/collar is to inhibit perivalvular leak/regurgitation of blood around the prosthesis. By flexing and sealing across the irregular contours of the annulus and atrium, leaking is minimized and/or prevented.

The second function of the atrial cuff/collar is to provide an adjustable and/or compliant bioprosthetic valve. The heart and its structures undergo complex conformational changes during the cardiac cycle. For example, the mitral valve annulus has a complex geometric shape known as a hyperbolic paraboloid much like a saddle, with the horn being anterior, the seat back being posterior, and the left and right valleys located medially and laterally. Beyond this complexity, the area of the mitral annulus changes over the course of the cardiac cycle. Further, the geometry of the tricuspid valve and tricuspid annulus continues to be a topic of research, posing its own particular problems. Accordingly, compliance is a very important but unfortunately often overlooked requirement of cardiac devices. Compliance here refers to the ability of the valve to maintain structural position and integrity during the cardiac cycle. Compliance with the motion of the heart is a particularly important feature, especially the ability to provide localized compliance where the underlying surfaces are acting differently from the adjacent surfaces. This ability to vary throughout the cardiac cycle allows the valve to remain seated and properly deployed in a manner not heretofore provided.

Additionally, compliance may be achieved through the use of the tethers where the tethers are preferably made from an elastic material. Tether-based compliance may be used alone, or in combination with the atrial cuff/collar-based compliance.

The third function of the atrial cuff/collar and valve is to provide a valve that, during surgery, is able to be seated and be able to contour to the irregular surfaces of the atrium. The use of independent tethers allows for side to side fitting of the valve within the annulus. For example, where three tethers are used, they are located circumferentially about 120 degrees relative to each other which allows the surgeon to observe whether or where perivalvular leaking might be occurring and to pull on one side or the other to create localized pressure and reduce or eliminate the leaking.

The fourth function of the atrial cuff/collar is to counter the forces that act to displace the prosthesis toward/into the ventricle (i.e. atrial pressure and flow-generated shear stress) during ventricular filling.

Additional features of the atrial cuff/collar include that it functions to strengthen the leaflet assembly/stent combination by providing additional structure. Further, during deployment, the atrial cuff/collar functions to guide the entire structure, the prosthetic valve, into place at the mitral annulus during deployment and to keep the valve in place once it is deployed. Another important function is to reduce pulmonary edema by improving atrial drainage.

Structure of the Improved Cuff/Collar

The atrial cuff/collar is a substantially flat plate that projects beyond the diameter of the tubular stent to form a rim or border. As used herein, the term atrial cuff/collar, cuff, flange, collar, bonnet, apron, or skirting are considered to be functionally equivalent. When the tubular stent is pulled through the mitral valve aperture, the mitral annulus, by the tether loops in the direction of the left ventricle, the atrial cuff/collar acts as a collar to stop the tubular stent from traveling any further through the mitral valve aperture. The entire prosthetic valve is held by longitudinal forces between the atrial cuff/collar which is seated in the left atrium and mitral annulus, and the ventricular tethers attached to the left ventricle.

The atrial cuff/collar is formed from a stiff, flexible shape-memory material such as the nickel-titanium alloy material Nitinol TM wire that is covered by stabilized tissue or other suitable biocompatible or synthetic material. In one embodiment, the atrial cuff/collar wire form is constructed from independent loops of wire that create lobes or segments extending axially around the circumference of the bend or seam where the atrial cuff/collar transitions to the tubular stent (in an integral atrial cuff/collar) or where the atrial cuff/collar is attached to the stent (where they are separate, but joined components).

Once covered by stabilized tissue or material, the loops provide the atrial cuff/collar the ability to travel up and down, to articulate, along the longitudinal axis that runs through the center of the tubular stent. In other words, the individual spindles or loops can independently move up and down, and can spring back to their original position due to the relative stiffness of the wire. The tissue or material that covers the atrial cuff/collar wire has a certain modulus of elasticity such that, when attached to the wire of the atrial cuff/collar, is able to allow the wire spindles to move. This flexibility gives the atrial cuff/collar, upon being deployed within a patient's heart, the ability to conform to the anatomical shape necessary for a particular application. In the example of a prosthetic mitral valve, the atrial cuff/collar is able to conform to the irregularities of the left atrium and shape of the mitral annulus, and to provide a tight seal against the atrial tissue adjacent the mitral annulus and the tissue within the mitral annulus. As stated previously, this feature importantly provides a degree of flexibility in sizing the a mitral valve and prevents blood from leaking around the implanted prosthetic heart valve.

An additional important aspect of the atrial cuff/collar dimension and shape is that, when fully seated and secured, the edge of the atrial cuff/collar preferably should not be oriented laterally into the atrial wall such that it can produce a penetrating or cutting action on the atrial wall.

In one preferred embodiment, the wire spindles of the atrial cuff/collar are substantially uniform in shape and size. In another preferred embodiment of the present invention, each loop or spindle may be of varying shapes and sizes. In this example, it is contemplated that the loops may form a pattern of alternating large and small loops, depending on where the valve is being deployed. In the case of a prosthetic mitral valve, pre-operative imaging may allow for customizing the structure of the atrial cuff/collar depending on a particular patient's anatomical geometry in the vicinity of the mitral annulus.

The atrial cuff/collar wire form is constructed so as to provide sufficient structural integrity to withstand the intracardiac forces without collapsing. The atrial cuff/collar wire form is preferably constructed of a superelastic metal, such as Nitinol (TM)® and is capable of maintaining its function as a sealing collar for the tubular stent while under longitudinal forces that might cause a structural deformation or valve displacement. It is contemplated as within the scope of the invention to optionally use other shape memory alloys such as Cu—Zn—Al—Ni alloys, and Cu—Al—Ni alloys. The heart is known to generate an average left atrial pressure between about 8 and 30 mm Hg (about 0.15 to 0.6 psi). This left atrial filling pressure is the expected approximate pressure that would be exerted in the direction of the left ventricle when the prosthesis is open against the outer face of the atrial cuff/collar as an anchoring force holding the atrial cuff/collar against the atrial tissue that is adjacent the mitral valve. The atrial cuff/collar counteracts this longitudinal pressure against the prosthesis in the direction of the left ventricle to keep the valve from being displaced or slipping into the ventricle. In contrast, left ventricular systolic pressure, normally about 120 mm Hg, exerts a force on the closed prosthesis in the direction of the left atrium. The tethers counteract this force and are used to maintain the valve position and withstand the ventricular force during ventricular contraction or systole. Accordingly, the atrial cuff/collar has sufficient structural integrity to provide the necessary tension against the tethers without being dislodged and pulled into the left ventricle. After a period of time, changes in the geometry of the heart and/or fibrous adhesion between prosthesis and surrounding cardiac tissues may assist or replace the function of the ventricular tethers in resisting longitudinal forces on the valve prosthesis during ventricular contraction.

Stent Structure

Preferably, superelastic metal wire, such as Nitinol® wire, is used for the stent, for the inner wire-based leaflet assembly that is disposed within the stent, and for the sealing cuff wire form. As stated, it is contemplated as within the scope of the invention to optionally use other shape memory alloys such as Cu—Zn—Al—Ni alloys, and Cu—Al—Ni alloys. It is contemplated that the stent may be constructed as a braided stent or as a laser cut stent. Such stents are available from any number of commercial manufacturers, such as Pulse Systems. Laser cut stents are preferably made from Nickel-Titanium (Nitinol®), but also without limitation made from stainless steel, cobalt chromium, titanium, and other functionally equivalent metals and alloys, or Pulse Systems braided stent that is shape-set by heat treating on a fixture or mandrel.

One key aspect of the stent design is that it be compressible and when released have the stated property that it return to its original (uncompressed) shape. This requirement limits the potential material selections to metals and plastics that have shape memory properties. With regards to metals, Nitinol has been found to be especially useful since it can be processed to be austhenitic, martensitic or super elastic. Martensitic and super elastic alloys can be processed to demonstrate the required compression features.

In one preferred embodiment, the valve, in lateral cross-section, is "D-shaped". Having one side that is relatively flat allows the valve to seat against the native anterior leaflet, tracking the shape of the anterior annulus, without putting excessive pressure on the aortic valve which is located immediately adjacent the anterior leaflet. The D-shape also provides the rounded posterior valve/stent wall to track the shape of the posterior annulus and seat securely against the posterior leaflet.

In this regard, in one preferred aspect the deployment of the D-shaped valve may be offset such that the flat wall, or straight line of the "D", is positioned along the axis between the mitral annulus and the aortic valve.

In another preferred embodiment, the valve, in lateral cross-section, is "kidney shaped" or "kidney bean shaped". This three-dimensional shape, like the D-shape, allows the valve to seat against the native anterior leaflet, tracking the shape of the anterior annulus, without putting excessive pressure on the aortic valve which is located immediately adjacent the anterior leaflet.

Laser Cut Stent

One possible construction of the stent envisions the laser cutting of a thin, isodiametric Nitinol tube. The laser cuts form regular cutouts in the thin Nitinol® tube. Secondarily the tube is placed on a mold of the desired shape, heated to the Martensitic temperature and quenched. The treatment of the stent in this manner will form a stent or stent/sealing cuff that has shape memory properties and will readily revert to the memory shape at the calibrated temperature.

Braided Wire Stent

A stent can be constructed utilizing simple braiding techniques. Using a Nitinol wire—for example a 0.012" wire—and a simple braiding fixture, the wire is wound on the braiding fixture in a simple over/under braiding pattern until an isodiametric tube is formed from a single wire. The two loose ends of the wire are coupled using a stainless steel or Nitinol coupling tube into which the loose ends are placed and crimped. Angular braids of approximately 60 degrees have been found to be particularly useful. Secondarily, the braided stent is placed on a shaping fixture and placed in a muffle furnace at a specified temperature to set the stent to the desired shape and to develop the martensitic or super elastic properties desired.

The stent as envisioned in one preferred embodiment is designed such that the ventricular aspect of the stent comes to 1-5 points onto which one or more anchoring sutures are affixed. The anchoring sutures (tethers) will traverse the ventricle and ultimately be anchored to the epicardial surface of the heart approximately at the level of the apex. The tethers when installed under slight tension will serve to hold the valve in place, i.e. inhibit paravalvular leakage during systole.

Narrow Gauge Stent to Treat Commissural Regurgitation and/or Secondary Mitral Regurgitation "Primary MR" is a term describing mitral regurgitation caused by an anatomic defect in the valve or associated tissue. The defect can either be congenital or degenerative, with causal factors ranging from marfan syndrome to drug- or radiation-inducement.

"Secondary MR" (also known as "Functional MR"), unlike Primary MR, is classified as a defect in valvular function or mechanics, as opposed to an anatomical defect. In such cases, an anatomically normal mitral valve has become regurgitant, usually as a result of impaired left ventricle from dilated cardiomyopathy or a myocardial infarction. Causality can be either ischemic or nonischemic. Specifically, chordae tendinae and papillary muscles can be stretched from increased tension, and the valve annulus itself may become distended due to the altered position of surrounding myocardium. Frequently, dilation of the left ventricle results in "volume overload" of blood during periods of systole, inhibiting full coaptation of the leaflets.

Secondary MR involves a defect in valvular function or mechanics, as opposed to an anatomical defect. In these cases, an anatomically normal mitral valve has become regurgitant, usually as a result of impaired left ventricle from dilated cardiomyopathy or a myocardial infarction. Specifically, chordae tendinae and papillary muscles can be stretched from increased tension, and the valve annulus itself may become distended due to the altered position of surrounding myocardium. Frequently, dilation of the left ventricle results in volume overload during periods of systole, inhibiting full coaptation of the leaflets.

Types of treatment currently in use for Secondary MR include treatments to decrease the circumference of the valvular orifice; decreasing the size of the mitral orifice, either by cinching the leaflets or restricting the movement of the leaflets; or remodeling the left ventricle to decrease the dimensions there. Examples of procedures to limit the size of the mitral orifice and/or enhance leaflet coaptation include the anchoring of one or more balloon devices across the mitral valve orifice to provide a backstop for leaflet coaptation and the use of sutures or clips to attach the leaflets at the point of coaptation. These methods are known to involve thrombotic and stenotic complications.

Secondary MR can be subclassified by leaflet movement (Carpentier's classification): type I (normal valve movement, such as annular dilatation or leaflet perforation); type II (excessive movement); and type III (restrictive movement: Ma-diastolic restriction such as rheumatic disease; IIIb-systolic restriction as in functional disease).

One particular aspect of secondary or "functional" mitral regurgitation is the presence of a "central jet" of regurgitant blood flowing through and near the center of the point of coaptation during regurgitation.

In one non-limiting preferred embodiment, the prosthetic valve is used to close the valve to this central jet flow, while leaving the commissures free to seal. This embodiment has yielded unexpected benefits in ameliorating the effects of commissural regurgitation and/or secondary mitral regurgitation, such as LV hypertrophy. It is thought that this unexpected benefit is likely due benefit is potentially due to the overall reduction in regurgitation and increased pumping efficiency, combined with the lessened deformity of the native commissures, this eliminating most or all of the mitral commissural regurgitation.

In another non-limiting preferred embodiment, the diameter of the stent body should be less than the diameter of the native mitral annulus. In one preferred embodiment, the stent diameter is between 50% and 95% of the diameter of the native mitral annulus. In another preferred embodiment, the stent diameter is between 75% and 90% of the diameter of the native mitral annulus. Preferably, the valve is positioned within the point of coaptation so as not to impair the opening of either the posterior or anterior commissions, thereby allowing the prosthetic valve to stop central jet regurgitation, while avoiding structural deformation or interaction with the mitral commissures.

In another non-limiting preferred embodiment, the diameter of the stent body should be less than the distance between the inward-facing tips of the two commissural cusps.

In another non-limiting preferred embodiment, the diameter of the stent body should approximately match the distance between the inward-facing tips of the two commissural cusps. In another non-limiting preferred embodiment, the diameter of the stent body should be approximately 18-32 mm. In a more preferred embodiment, the diameter of the stent body should be 20-30 mm. In a more preferred embodiment, the diameter of the stent body should be 23-28 mm.

The average area of an open mitral valve is between 4 cm2 and 6 cm2. In another non-limiting preferred embodiment, the diameter of the stent body may be between 75% and 99% of the mitral valve cross-sectional leaflet diameter. In another preferred embodiment, the diameter of the stent body may be between 85% and 98% of the mitral valve cross-sectional leaflet diameter. In another preferred embodiment, the diameter of the stent body may be between 92% and 97% of the mitral valve cross-sectional leaflet diameter.

The degree of severity of mitral regurgitation can be quantified by the regurgitant fraction, which is the percentage of the left ventricular stroke volume that regurgitates into the left atrium.

$$\text{Regurgitant fraction} = \frac{V_{mitral} - V_{aortic}}{V_{mitral}} \times 100\%,$$

where $V_{mitral}$ and $V_{aortic}$ are respectively the volumes of blood that flow forward through the mitral valve and aortic valve during a cardiac cycle. Methods that have been used to assess the regurgitant fraction in mitral regurgitation include echocardiography, cardiac catheterization, fast CT scan, and cardiac MRI.

The degree of mitral regurgitation is often gauged according to the regurgitant fraction.

Determination of the degree of mitral regurgitation

| Degree of mitral regurgitation | Regurgitant fraction | Regurgitant Orifice area |
|---|---|---|
| Mild mitral regurgitation | <20 percent | |
| Moderate mitral regurgitation | 20-40 percent | |
| Moderate to severe mitral regurgitation | 40-60 percent | |
| Severe mitral regurgitation | >60 percent | >0.4 cm² |

In another non-limiting preferred embodiment, the stent body shall be shaped to allow for continued commissural regurgitation of 20% or less. In a more preferred embodiment, the stent body shall be shaped to avoid commissural deformation and/or commissural regurgitation of 10% or less. In another preferred embodiment, the stent body shall be shaped to avoid commissural deformation and/or commissural regurgitation of 5% or less.

Leaflet and Assembly Structure

The valve leaflets are held by, or within, a leaflet assembly. In one preferred embodiment of the invention, the leaflet assembly comprises a leaflet wire support structure to which the leaflets are attached and the entire leaflet assembly is housed within the stent body. In this embodiment, the assembly is constructed of wire and stabilized tissue to form a suitable platform for attaching the leaflets. In this aspect, the wire and stabilized tissue allow for the leaflet structure to be compressed when the prosthetic valve is compressed within the deployment catheter, and to spring open into the proper functional shape when the prosthetic valve is opened during deployment. In this embodiment, the leaflet assembly may optionally be attached to and housed within a separate cylindrical liner made of stabilized tissue or material, and the liner is then attached to line the interior of the stent body.

In this embodiment, the leaflet wire support structure is constructed to have a collapsible/expandable geometry. In a preferred embodiment, the structure is a single piece of wire. The wireform is, in one embodiment, constructed from a shape memory alloy such as Nitinol. The structure may optionally be made of a plurality of wires, including between 2 to 10 wires. Further, the geometry of the wire form is without limitation, and may optionally be a series of parabolic inverted collapsible arches to mimic the saddle-like shape of the native annulus when the leaflets are attached. Alternatively, it may optionally be constructed as collapsible concentric rings, or other similar geometric forms that are able to collapse/compress which is followed by an expansion to its functional shape. In certain preferred embodiments, there may be 2, 3 or 4 arches. In another embodiment, closed circular or ellipsoid structure designs are contemplated. In another embodiment, the wire form may be an umbrella-type structure, or other similar unfold-and-lock-open designs. A preferred embodiment utilizes super elastic Nitinol wire approximately 0.015" in diameter. In one preferred embodiment, the diameter is 0.012". In this embodiment, the wire is wound around a shaping fixture in such a manner that 2-3 commissural posts are formed. The fixture containing the wrapped wire is placed in a muffle furnace at a pre-determined temperature to set the shape of the wire form and to impart it's super elastic properties. Secondarily, the loose ends of the wireform are joined with a stainless steel or Nitinol tube and crimped to form a continuous shape. In another preferred embodiment, the commissural posts of the wireform are adjoined at their tips by a circular connecting ring, or halo, whose purpose is to minimize inward deflection of the post(s).

In another preferred embodiment, the leaflet assembly is constructed solely of stabilized tissue or other suitable material without a separate wire support structure. The leaflet assembly in this embodiment is also disposed within the lumen of the stent and is attached to the stent to provide a sealed joint between the leaflet assembly and the inner wall of the stent. By definition, it is contemplated within the scope of the invention that any structure made from stabilized tissue and/or wire(s) related to supporting the leaflets within the stent constitute a leaflet assembly.

In this embodiment, stabilized tissue or suitable material may also optionally be used as a liner for the inner wall of the stent and is considered part of the leaflet assembly.

Liner tissue or biocompatible material may be processed to have the same or different mechanical qualities, e.g. thickness, durability, etc. from the leaflet tissue.

Deployment within the Valvular Annulus

The prosthetic heart valve is, in one embodiment, apically delivered through the apex of the left ventricle of the heart using a catheter system. In one aspect of the apical delivery, the catheter system accesses the heart and pericardial space by intercostal delivery. In another delivery approach, the catheter system delivers the prosthetic heart valve using either an antegrade or retrograde delivery approach using a flexible catheter system, and without requiring the rigid tube system commonly used. In another embodiment, the catheter system accesses the heart via a trans-septal approach.

In one non-limiting preferred embodiment, the stent body extends into the ventricle about to the edge of the open mitral valve leaflets (approximately 25% of the distance between the annulus and the ventricular apex). The open native leaflets lay against the outside stent wall and parallel to the long axis of the stent (i.e. the stent holds the native mitral valve open).

In one non-limiting preferred embodiment, the diameter should approximately match the diameter of the mitral annulus. Optionally, the valve may be positioned to sit in the mitral annulus at a slight angle directed away from the aortic valve such that it is not obstructing flow through the aortic valve. Optionally, the outflow portion (bottom) of the stent should not be too close to the lateral wall of the ventricle or papillary muscle as this position may interfere with flow through the prosthesis. As these options relate to the tricuspid, the position of the tricuspid valve may be very similar to that of the mitral valve.

In another embodiment, the prosthetic valve is sized and configured for use in areas other than the mitral annulus, including, without limitation, the tricuspid valve between the right atrium and right ventricle. Alternative embodiments may optionally include variations to the sealing cuff structure to accommodate deployment to the pulmonary valve between the right ventricle and pulmonary artery, and the aortic valve between the left ventricle and the aorta. In one embodiment, the prosthetic valve is optionally used as a venous backflow valve for the venous system, including without limitation the vena cava, femoral, subclavian, pulmonary, hepatic, renal and cardiac. In this aspect, the sealing cuff feature is utilized to provide additional protection against leaking.

Tethers

In one preferred embodiment, there are tethers attached to the prosthetic heart valve that extend to one or more tissue anchor locations within the heart. In one preferred embodiment, the tethers extend downward through the left ventricle, exiting the left ventricle at the apex of the heart to be fastened on the epicardial surface outside of the heart. Similar anchoring is contemplated herein as it regards the tricuspid, or other valve structure requiring a prosthetic. There may be from 1 to 8 tethers which are preferably attached to the stent.

In another preferred embodiment, the tethers may optionally be attached to the sealing cuff to provide additional control over position, adjustment, and compliance. In this preferred embodiment, one or more tethers are optionally attached to the sealing cuff, in addition to, or optionally, in place of, the tethers attached to the stent. By attaching to the sealing cuff and/or the stent, an even higher degree of control over positioning, adjustment, and compliance is provided to the operator during deployment.

During deployment, the operator is able to adjust or customize the tethers to the correct length for a particular patient's anatomy. The tethers also allow the operator to tighten the sealing cuff onto the tissue around the valvular annulus by pulling the tethers, which creates a leak-free seal.

In another preferred embodiment, the tethers are optionally anchored to other tissue locations depending on the particular application of the prosthetic heart valve. In the case of a mitral valve, or the tricuspid valve, there are optionally one or more tethers anchored to one or both papillary muscles, septum, and/or ventricular wall.

The tethers, in conjunction with the sealing cuff or collar, provide for a compliant valve which has heretofore not been available. The tethers are made from surgical-grade materials such as biocompatible polymer suture material. Examples of such material include 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle. Upon being drawn to and through the apex of the heart, the tethers may be fastened by a suitable mechanism such as tying off to a pledget or similar adjustable button-type anchoring device to inhibit retraction of the tether back into the ventricle. It is also contemplated that the tethers might be bioresorbable/bioabsorbable and thereby provide temporary fixation until other types of fixation take hold such a biological fibrous adhesion between the tissues and prosthesis and/or radial compression from a reduction in the degree of heart chamber dilation.

Further, it is contemplated that the prosthetic heart valve may optionally be deployed with a combination of installation tethers and permanent tethers, attached to either the stent or sealing cuff, or both, the installation tethers being removed after the valve is successfully deployed. It is also contemplated that combinations of inelastic and elastic tethers may optionally be used for deployment and to provide structural and positional compliance of the valve during the cardiac cycle.

Pledget

In one embodiment, to control the potential tearing of tissue at the apical entry point of the delivery system, a circular, semi-circular, or multi-part pledget is employed. The pledget may be constructed from a semi-rigid material such as PFTE felt. Prior to puncturing of the apex by the delivery system, the felt is firmly attached to the heart such that the apex is centrally located. Secondarily, the delivery system is introduced through the central area, or orifice as it may be, of the pledget. Positioned and attached in this manner, the pledget acts to control any potential tearing at the apex.

Tines/Barbs

In another embodiment the valve can be seated within the valvular annulus through the use of tines or barbs. These may be used in conjunction with, or in place of one or more tethers. The tines or barbs are located to provide attachment to adjacent tissue. In one preferred embodiment, the tines are optionally circumferentially located around the bend/transition area between the stent and the sealing cuff. Such tines are forced into the annular tissue by mechanical means such as using a balloon catheter. In one non-limiting embodiment, the tines may optionally be semi-circular hooks that upon expansion of the stent body, pierce, rotate into, and hold annular tissue securely.

Functions of the Spring Anchor

The spring anchor will form a spring-shaped wire or banded extending from the base of the self-expanding stent. The anchor will provide support to hold the stent within the natural valve annulus by being coiled around the chordae tendineae extending from the natural valve annulus. The spring mechanism of the anchor will allow consistent support to the prosthetic valve stent, despite repetitive deformation as the chordae tendineae, valve annulus and surrounding tissue contract and release. The shape memory characteristics of the coil will allow each loop deform and move independently in response to each heart contraction, and then return to the original coil dimensions as the heart relaxes. The placement of the coil around the chordae tendineae will anchor the stent to counteract the natural tendency of the stent to move laterally with the cardiac tissue contractions and releases, and longitundinally with the blood flow between the ventricle and the atrium.

Deployment of the Spring Anchor

The spring anchor will be fused to the prosthetic valve stent via either welding, soldering or adhesion prior to insertion of the entire valve and anchor assembly into a delivery catheter.

The delivery catheter will approach the heart via either transvenous, transarterial or percutaneous delivery. Delivery may be made through into the left or right ventricle, or the left or right atrium.

Delivery into the right ventricle may be made through the intercostal space and thereby through the lateral ventricular wall. Delivery into the right atrium may be made using a transvenous approach.

Delivery into the left ventricle may be made through the intercostal space, using an apical approach or through the lateral ventricular wall. A transarterial retrograde aortic valve approach and a transvenous septostomy approach may also be used.

Upon deployment of the self-expanding prosthetic valve within the native valvular annulus, whether in the tricuspid valve annulus, mitral valve annulus, or otherwise, the catheter sheath will be withdrawn, allowing the spring anchor to deploy. Such anchor deployment will result in the expanding of the coiled loops into a spring-like shape of sufficient diameter to allow circumnavigation of the chordae tendineae.

After release of the spring anchor, control of the anchor will be maintained via surgical tools contained within the catheter and known in the art to guide the anchor around the chordae tendineae in a rotating, screw-like motion. The number of rotations performed will be determined by the number of loops contained within the spring anchor.

Alternatively, the surgeon may use a surgical tool contained within the catheter and known in the art to secure and pull the chordae tendineae within the circumference of one or more loops of the anchor.

Upon securing the anchor around the chordae tendineae, surgical tools may or may not be used to secure one or more anchoring tethers to surrounding pericardial tissue for additional support.

Upon the securing of the valve stent within the native annulus, the spring anchor around the chordae tendineae and the tethers, if any, to the pericardial tissue, all surgical tools manipulating said components will be disengaged, pulled into the catheter and the catheter withdrawn.

Spring Anchor Structure

The spring anchor is a single wire or band of shape-memory material, for example a 0.012" Nitinol wire, formed into a series of two or more circular loops, in which the proximal loop is attached to the base of the prosthetic valve stent.

Once the proximal loop has been attached to the base of the self-expanding stent, the additional loop(s) will radiate outward axially from the stent in the shape of a spring. The distal loop will be open, allowing for the tip to be placed outside a chordae tendineae during deployment, then rotated about a plurality of chordae tendineae in either a clockwise or counterclockwise direction until each non-proximal loop is deployed about and anchored against the outer tissue of the chordae tendineae.

In a preferred embodiment, the spring anchor is made of material identical to the material used to construct the base of the stent. In another preferred embodiment, the material of the anchor differs from the material of the stent base.

In a preferred embodiment, the proximal loop of the spring anchor is welded to the base of the stent, forming a continuous joint around the full diameter of the base. In another embodiment, the proximal loop of the anchor is soldered to the stent base, or adhered to the stent base using an adhesive substance known in the art.

Because of the shape-memory material's flexibility, the anchor has the ability to articulate back and forth both laterally and longitudinally, while returning to its original shape formation after each deformation. The loops can independently move back and forth, and can spring back to their original position due to the relative stiffness of the wire or band. The coil has a certain modulus of elasticity such that, when attached to the wire of the stent, is able to allow the collar to move. This flexibility gives the anchor, upon being deployed within a patient's heart, the ability to conform to the anatomical shape necessary for a particular application. In the example of a prosthetic mitral valve, the anchor is able to conform to the irregularities in the shape and disposition of the chordae tendineae, and to provide a tight grip against the chordae tendineae tissue to provide support to the prosthetic valve. As stated previously, this feature importantly provides a degree of flexibility in sizing the anchor and prevents dislocation of the anchor and/or prosthetic valve due to wear.

In one preferred anchor embodiment, each loop in the coil is substantially uniform in shape and diameter. In another preferred embodiment of the present invention, the loops may be of varying shapes and sizes. In this example, it is contemplated that the loops may gradually increase in diameter as they extend away from the stent base. The size and pattern of the loops may vary based on whether the valve replacement is being performed on the mitral valve or the tricuspid valve.

The anchor form is constructed so as to provide sufficient structural integrity to withstand the intracardiac forces without dislocating, permanently deforming or fracturing. The anchor assembly is preferably constructed of a wire or band constructed of a shape memory alloy, polymer or ceramic, such as Nitinol®, that is capable of maintaining its function as an anchor for the tubular stent while under lateral and longitudinal forces that might cause a structural deformation or valve displacement. It is contemplated as within the scope of the invention to optionally use other shape memory alloys or materials such as listed herein.

For example, assuming a mitral valve replacement prosthesis, the heart is known to generate an average left atrial pressure between about 8 and 30 mm Hg (about 0.15 to 0.6 psi). This left atrial filling pressure is the expected approximate pressure that would be exerted in the direction of the left ventricle when the prosthesis is open against the prosthesis within the mitral valve annulus. The anchor counteracts this downward longitudinal pressure against the prosthesis in the direction of the left ventricle to keep the valve from being displaced or slipping into the ventricle. In contrast, left ventricular systolic pressure, normally about 120 mm Hg, exerts a force on the closed prosthesis in the direction of the left atrium. The anchor would also counteract this force and be used to maintain the valve position and withstand the ventricular force during ventricular contraction or systole. Tethers may also be used to secure position against any other directional forces as necessary. After a period of time, changes in the geometry of the heart and/or fibrous adhesion between prosthesis and surrounding cardiac tissues, or between the anchor and surrounding cardiac tissues, may assist or replace the function of anchor and/or the ventricular tethers in resisting longitudinal forces on the valve prosthesis during ventricular contraction.

Description of Surface Improvements Figures

Figure 1:
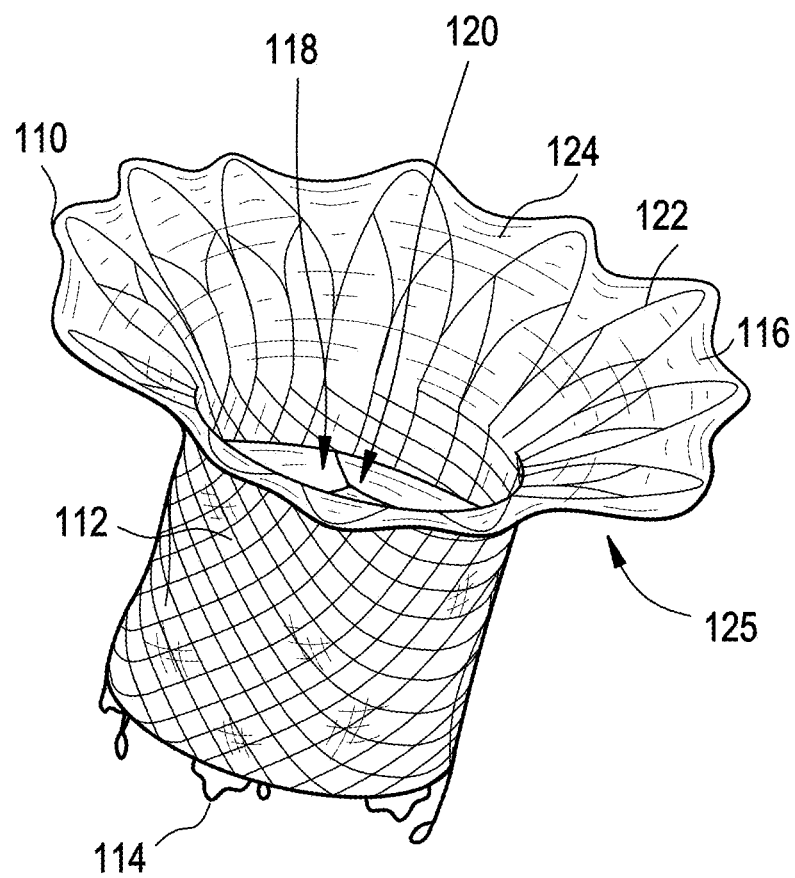
FIG. 1 is a perspective view of a drawing showing one embodiment of a prosthetic valve according to the present invention.

Referring now to the FIGURES, FIG. 1 shows one embodiment of a prosthetic heart valve 110 according to the present invention, comprising tubular stent 112 having optional tether attachment structures 114 at one end and tubular stent 112 provides integrated sealing cuff 116 at the other end. Leaflet assembly 118 is disposed within stent 112 and supports valve leaflets 120. Sealing cuff 116 has independent articulating loops of wire 122 and interior liner/covering 124 and exterior liner/covering 125.

Tubular stent 112 may be an expandable laser cut stent or an expandable braided stent. Tubular stent 112 may be constructed of Martensitic or super elastic metal alloys. Tubular stent 112 may be compressed along its longitudinal axis and will fit into a catheter-based stent delivery system. When the tubular stent 112 is delivered to the location where it is to be installed, it is expelled from the catheter by an obturator and deposited at the site where it is to be deployed.

Tubular stent 112 includes a plurality of optional tether attachments 114 upon which a tether (not shown) may be connected. FIG. 1 shows an embodiment having three tether attachments which are integrated into the distal portion of the stent 112.

Leaflet assembly 118 is a separate but integrated structure that is disposed within the stent 112. Leaflet assembly 118 functions to provide the structure upon which the valve leaflets or cusps 120 are located. Leaflet assembly 118 may be made entirely of stabilized tissue or it may be a combination wire and tissue structure. Where leaflet assembly 118 is composed entirely of tissue, it is contemplated that the leaflet assembly, leaflet support structure, and leaflets or cusps 120 are made from tissue.

The prosthetic valve is covered with multiple layers of either synthetic material, or tissue, or both. This feature is described in greater detail herein. Different qualities of stabilized tissue, i.e. thin or thick, structurally rigid or flexible as it may be, may be used for the different components of the sealing cuff top covering 124, the stent interior liner/covering 124, the leaflet assembly 118 and the leaflets 120. Where leaflet assembly 118 is composed of wire and tissue, it contemplated that assembly or support(s), or both, may be made from wire, and the leaflet cusps 120 would necessarily be made from tissue.

Prosthetic heart valve 110 also includes sealing cuff 116. FIG. 1 shows sealing cuff 116 formed from a sealing cuff wire form 122 that is covered by, in one embodiment, interior liner/covering 124 and exterior liner/covering 125. Hash marks are provided to illustrate how the stent wire/cuff wire is covered on both sides. Hash marks may also indicate that the tissue or fabric is opaque, however it is not required.

In one embodiment, the sealing cuff wire form is an extension of the stent itself, where the stent has been heated and manipulated upon a form to create the extended spindles of the flat, collar plate of the sealing cuff.

Figure 2:
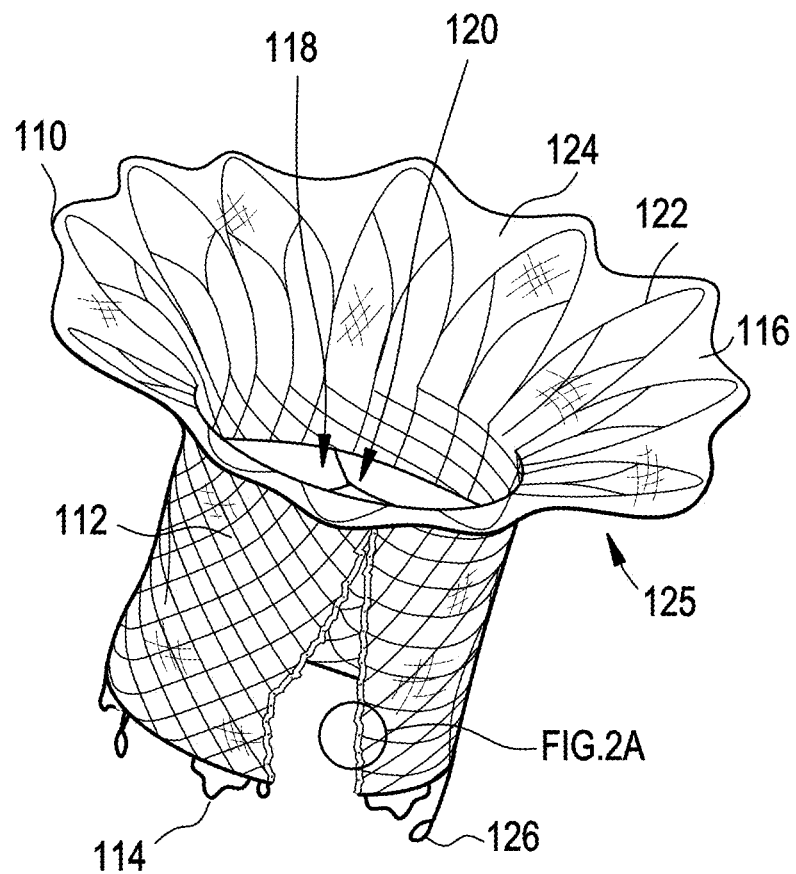
FIG. 2 is a perspective cut-away view of a drawing showing the multiple layered approach of the present invention.
Figure 2A:
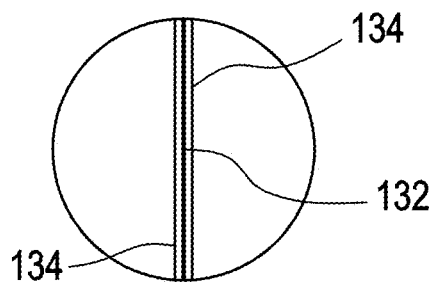
FIG. 2A shows a three-layer construction of a portion of the valve of FIG. 2.
Figure 2B:
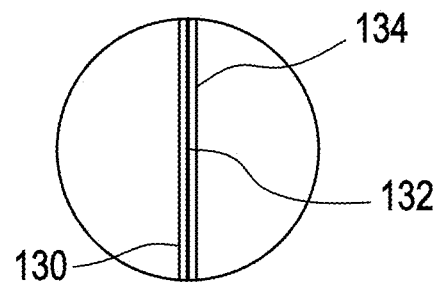
FIG. 2B shows a three-layer construction, including specially treated tissue, of a portion of the valve of FIG. 2.

Referring now to FIG. 2 is a cut-away sectional view of a multi-layer transcatheter valve according to one embodiment of the present invention. FIG. 2A shows a three-layer construction having synthetic polymeric material 134 on the inside, a stent made from wire 132, e.g. Nitinol®, and an outer covering made from a synthetic polymeric material 134, e.g. Dacron® polyester. FIG. 2B shows a three-layer construction having specially treated tissue 130 on the inside, a stent made from wire 132, e.g. Nitinol®, and an outer covering made from a synthetic polymeric material 134, e.g. Dacron® polyester.

Figure 3A:
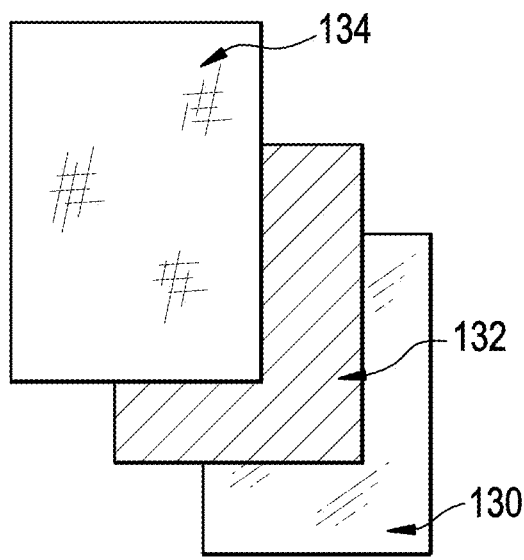
FIGS. 3A-3C is a series of drawings showing non-limiting variations of sandwiching treated tissue, stent, and synthetic material.
Figure 3C:
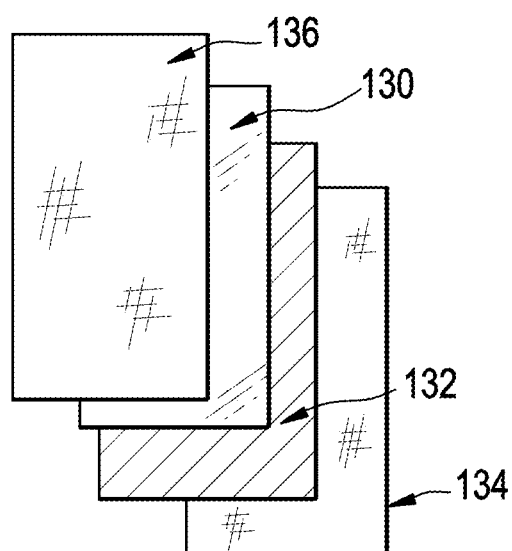
Figure 3B:
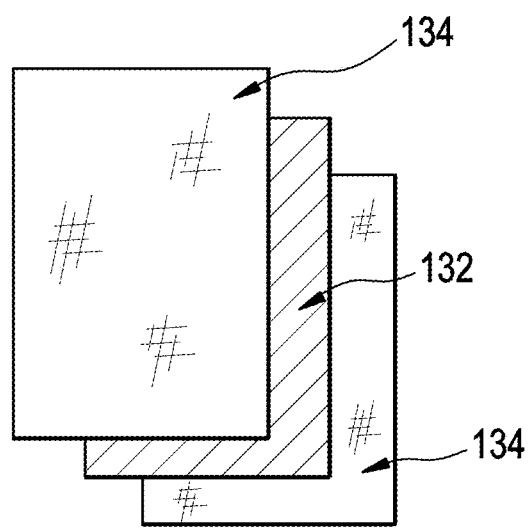

Referring now to FIG. 3, FIG. 3A illustrates an embodiment wherein tissue 130 is interior, supporting stent 132, and having outer synthetic material covering 134. FIG. 3B illustrates an embodiment wherein synthetic material 134 is used in both the interior and the exterior, with the metal stent 132 sandwiched between them. FIG. 3C illustrates how multiple layers may be constructed, with, for example, from inside the lumen of the stent to the outside, a synthetic material 134 is layered with a treated tissue layer 132, which is attached to the stent 130, which in turn is covered with a synthetic material 136 which may be the same or different as the inner synthetic material 134.

Figure 4A:
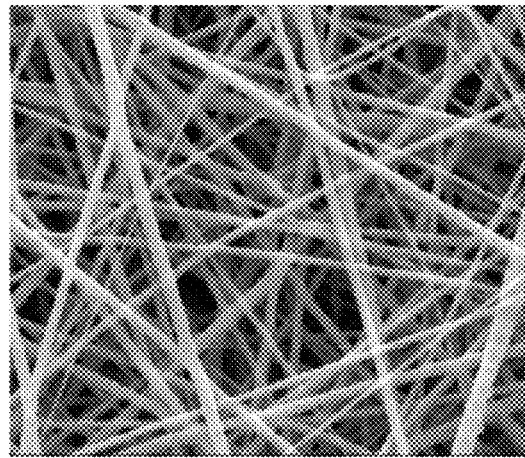
FIGS. 4A-4C is a series of electron micrographs showing the nanopores and scale of the electrospun synthetic material which may be used herein.
Figure 4B:
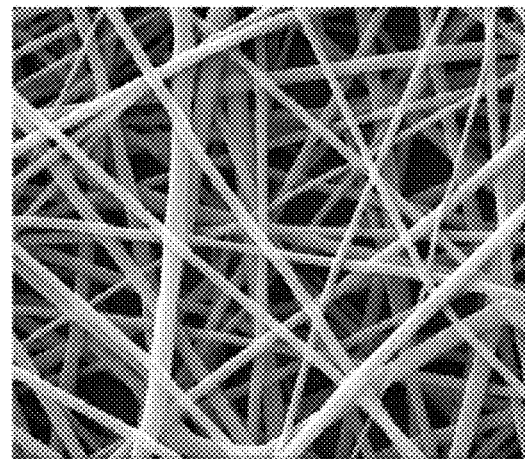
Figure 4C:
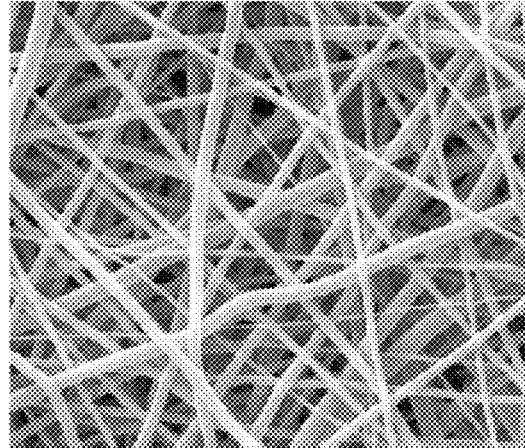

Referring now to FIG. 4, FIG. 4A is an electron microscope image of an electrospun PGA nanofiber fabricated to have a certain porosity and density. FIG. 4B is an electron microscope image of an electrospun PLGA nanofiber fabricated to have a different porosity and density. FIG. 4C is an electron microscope image of an electrospun PLLA-CL nanofiber fabricated to have an alternative porosity and density. These types of electrospun fibers are contemplated for use as one of the preferred, but not necessarily limited to, synthetic materials for use on the transcatheter valve herein.

Figure 5A:
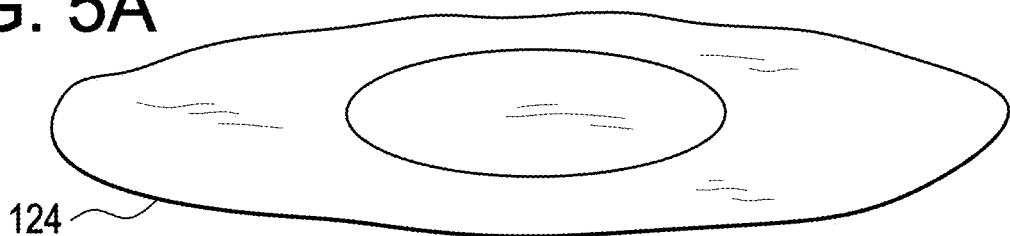
FIGS. 5A-5D is an exploded view showing detail of certain part of the invention, especially tissue for the cuff, the bare wire body of the stent, a synthetic material layer, and an internal leaflet component.
Figure 5B:
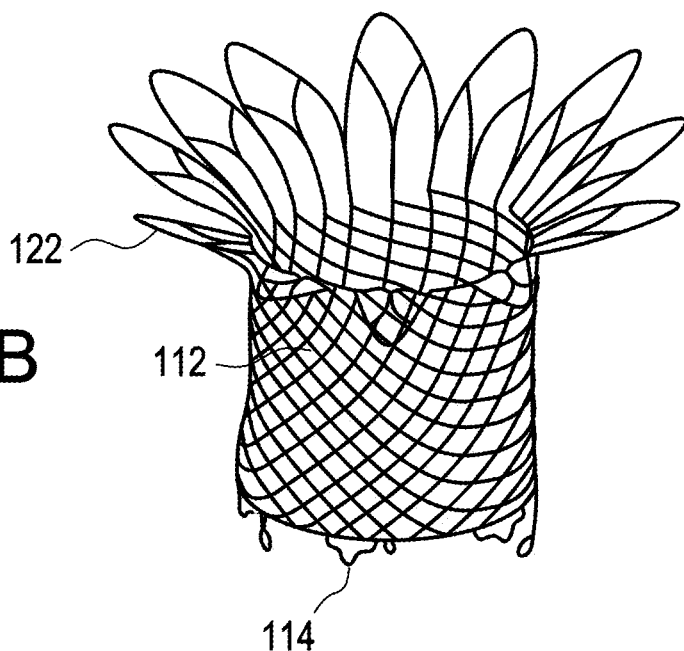
Figure 5C:
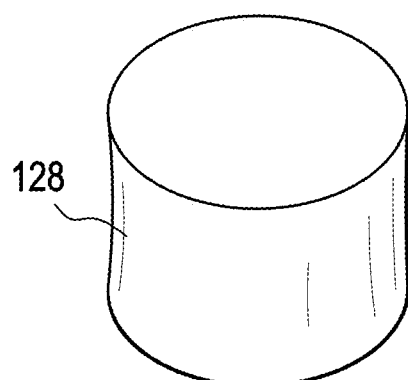
Figure 5D:
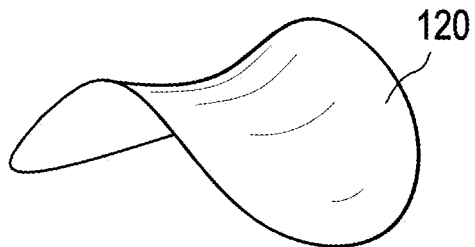

Referring now to FIGS. 5A-5D, there is an exploded view of one embodiment of the parts of the invention. FIG. 5A shows cuff covering 124 in a treated tissue example. In other alternative embodiments, the tissue may extend through the entirety of the lumen of the stent, as compared to being used only on the cuff, as here. Both variations are included within the invention. FIG. 5B shows heat-formed stent 112 with cuff loops 122. FIG. 5C shows synthetic polymeric material 128 as a band of material ready for covering the external/outer wall of the stent body below the cuff. As with the tissue, the synthetic material may cover part or all of the exterior of the stent, including the underside of the cuff loops. FIG. 5D shows a piece of treated tissue 120, without further detail, for use as the valve leaflet structure.

Figure 6:
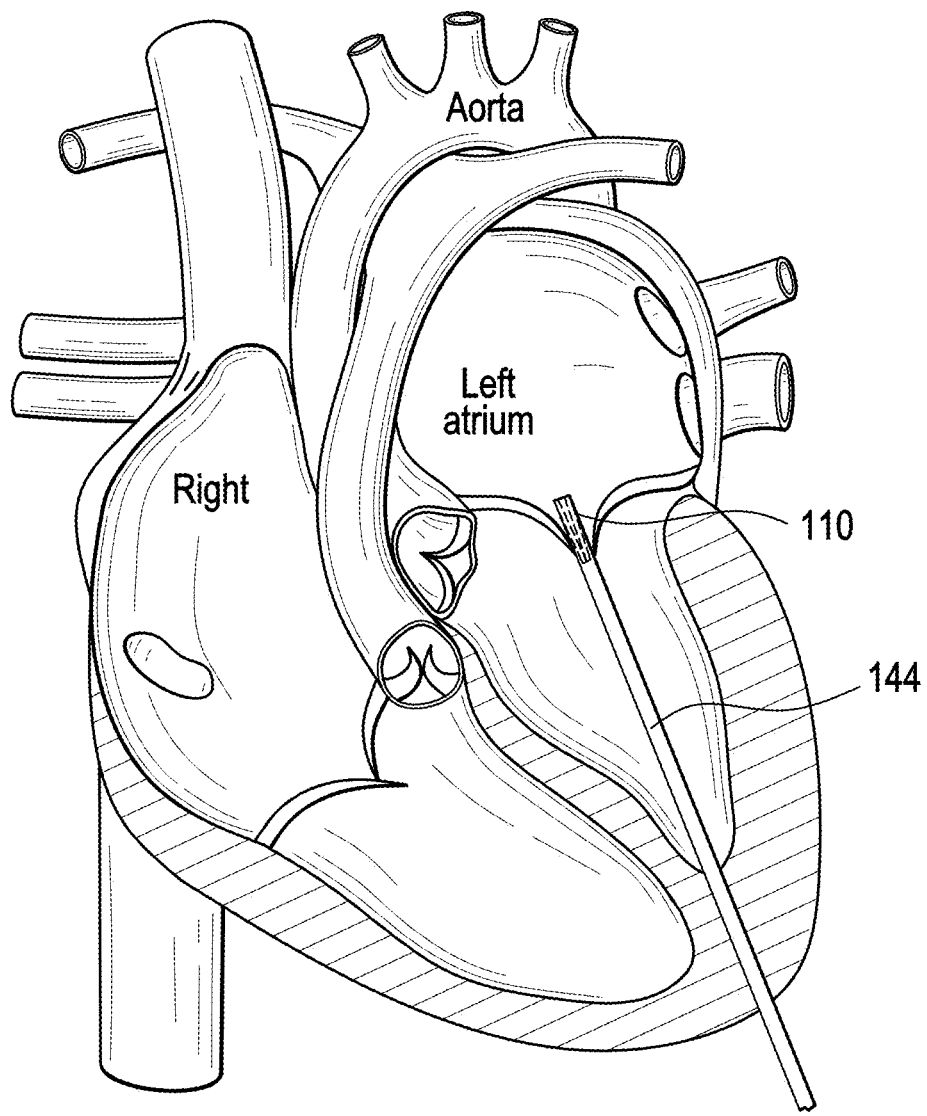
FIG. 6 is a cut-away view of a heart with a delivery catheter containing a prosthetic valve according to the present invention and accessing the heart using an apical approach.

Referring now to FIG. 6 is a cut-away view of a heart with a delivery catheter containing a prosthetic heart valve according to the present invention and accessing the heart using an apical approach. It is contemplated that other surgical approaches to the heart, and valves in addition to the mitral valve, are within the scope of the inventive subject matter claimed herein. FIG. 6 shows the delivery catheter 144 advanced to through the mitral valve and into the left atrium for deployment of the prosthetic valve 110.

Figure 7:
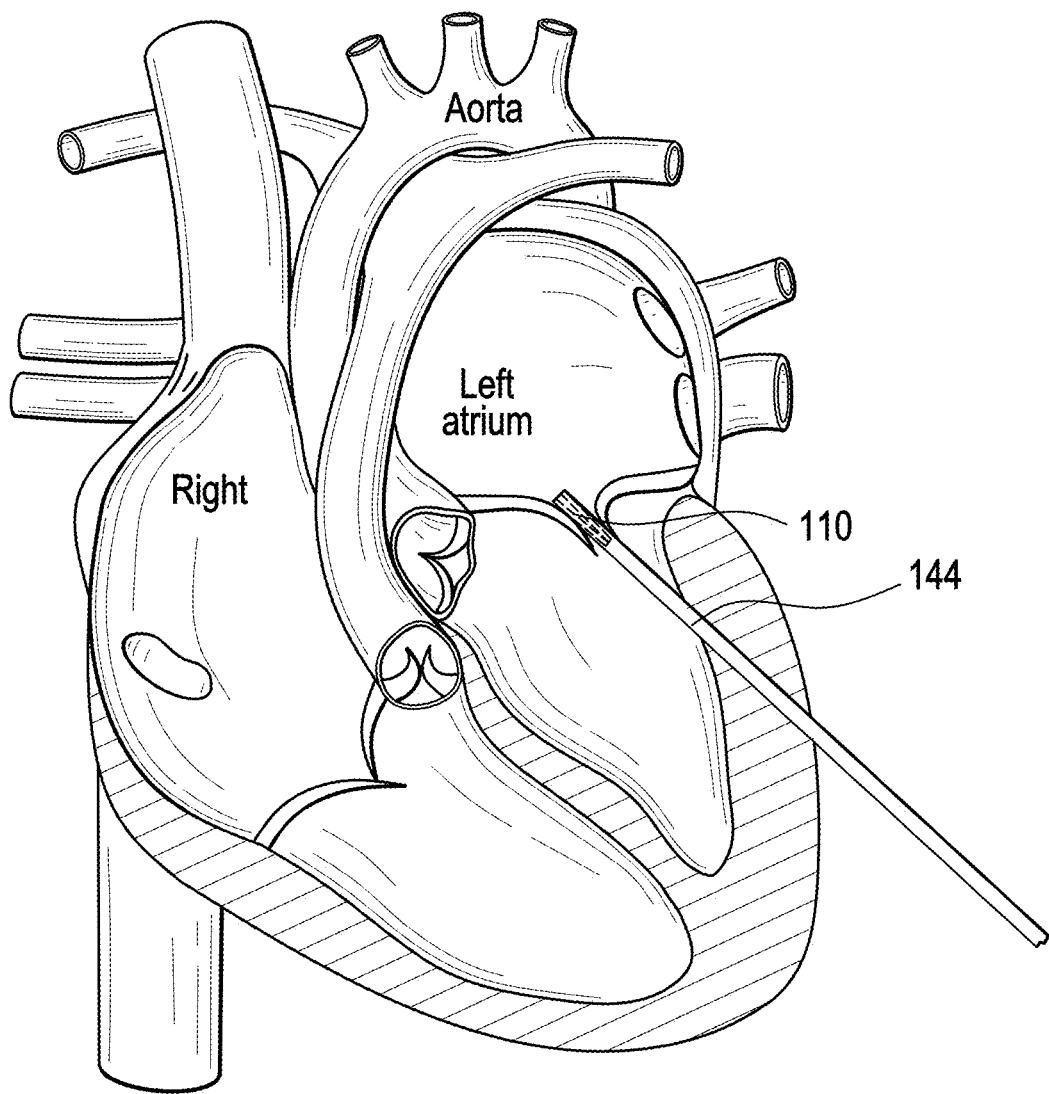
FIG. 7 is a cut-away view of a heart with a delivery catheter containing a prosthetic valve according to the present invention and accessing the heart using a lateral approach.

Referring now to FIG. 7, FIG. 7 shows the lateral deployment of one embodiment of a prosthetic valve according to the present invention and shows a prosthetic valve delivery catheter 144 that has accessed the left atrium via the left ventricle by way of a lateral trans-ventricular wall approach through the lateral wall of the left ventricle of the heart.

Figure 8:
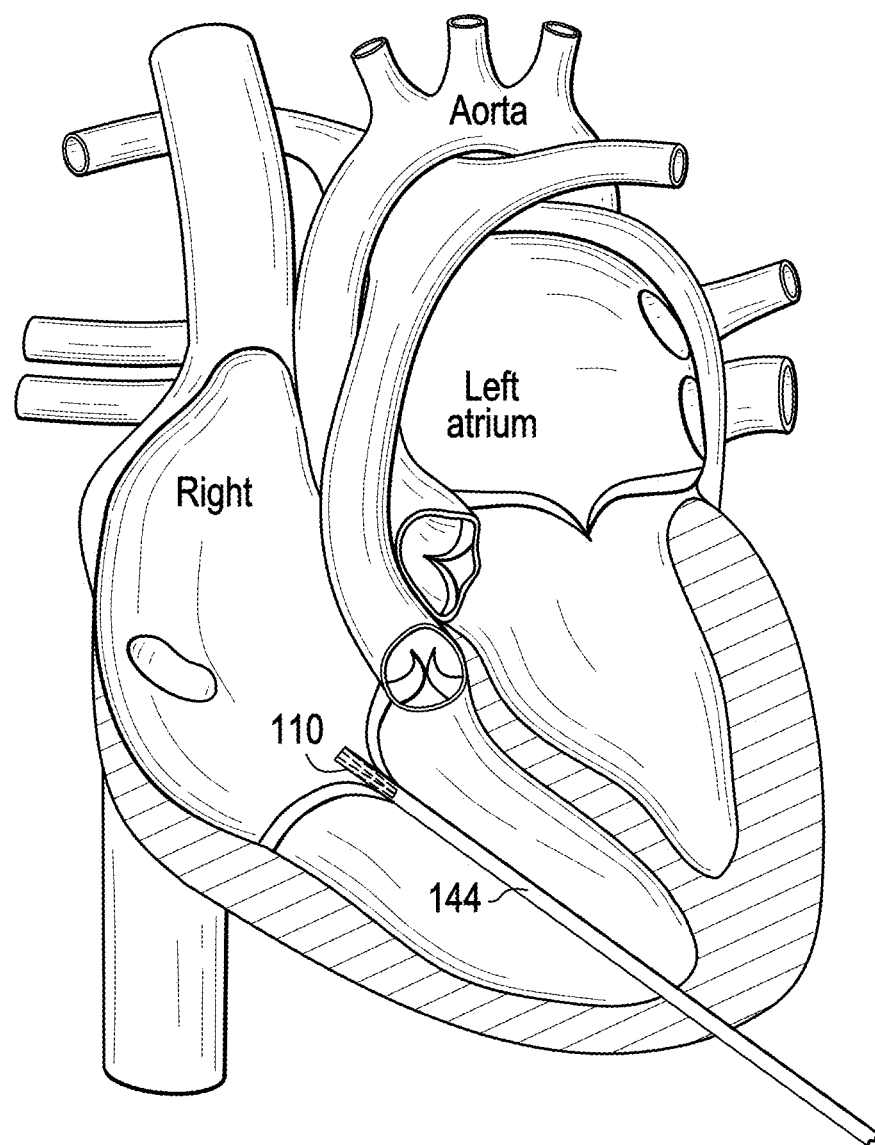
FIG. 8 is a cut-away view of a heart with a delivery catheter containing a prosthetic valve according to the present invention and accessing the right ventricle of the heart using an apical approach.

Referring now to FIG. 8, FIG. 8 is a cut-away view of a heart with a delivery catheter 144 containing a prosthetic heart valve according to the present invention and accessing the heart using an apical approach into the right ventricle. It is contemplated that other surgical approaches to the heart, and valves in addition to the mitral valve, are within the scope of the inventive subject matter claimed herein. FIG. 8 shows the delivery catheter 144 advanced to the tricuspid valve and into the right atrium for deployment of the prosthetic valve 110.

Figure 9A:
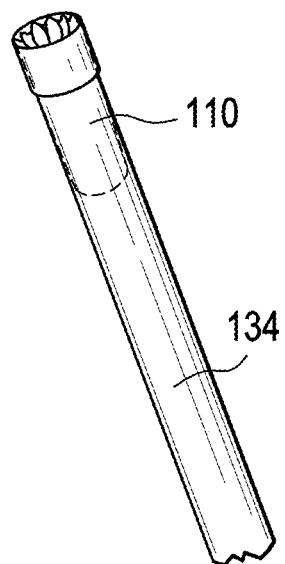
FIGS. 9A-9D is a series of drawings illustrating how the valve is deployed from the catheter.
Figure 9B:
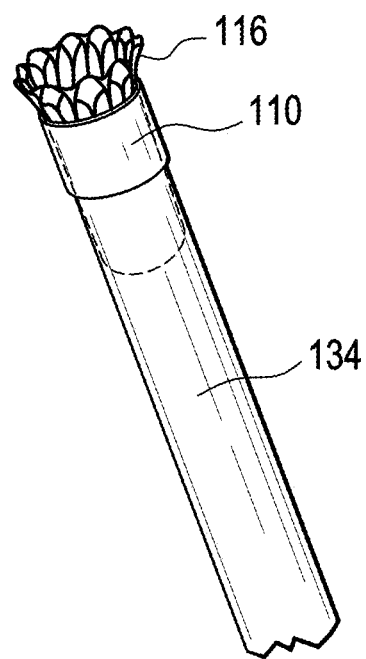
Figure 9C:
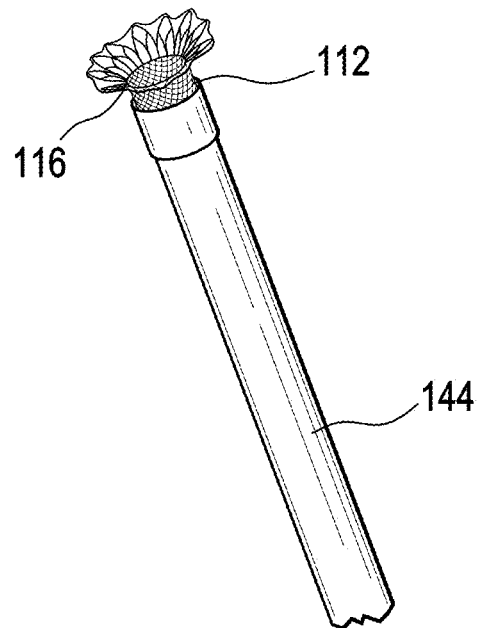
Figure 9D:
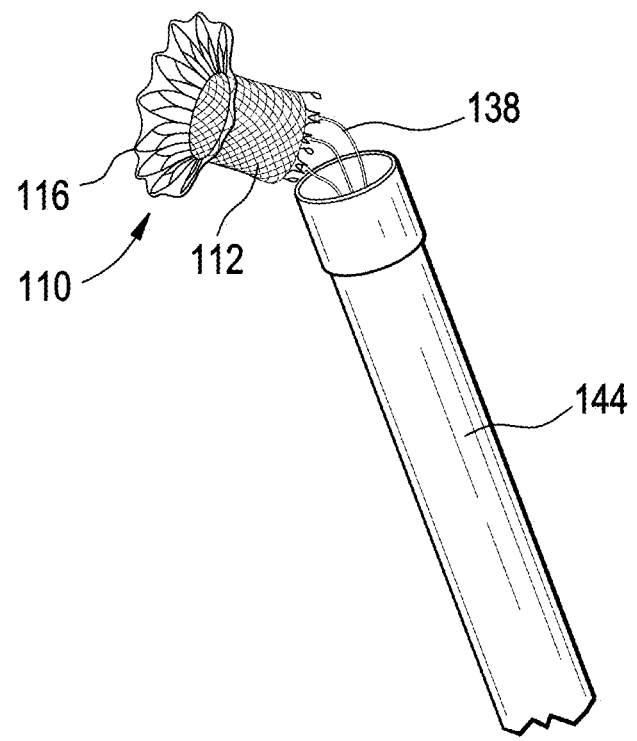

FIGS. 9A-9D is a series of drawings of the deployment of one embodiment of a prosthetic valve according to the present invention. FIGS. 9A-9D is a series of views of the tip of one embodiment of a delivery catheter according to the present invention containing a pre-loaded prosthetic valve which is being pushed out of the delivery catheter, i.e. by an obturator, starting with (A) the valve completely within the catheter, (B) the sealing cuff portion being in view, (C) the stent body following, and (D) the prosthetic valve with attached tethers for positioning and/or adjustment and/or securing the valve to tissue. FIGS. 9A-9D show how the prosthetic valve 110 is deployed from flexible deployment catheter 144. FIG. 9B shows the sealing cuff 116 emerging from the catheter 144. FIG. 9C shows the sealing cuff 116 and stent 112 partially expelled from the delivery catheter 144. FIG. 9D shows the prosthetic valve completely expelled from the delivery catheter 144 with tethers 138 attached to the stent body and trailing behind into the catheter. FIG. 9D further shows tethers 138 attached to the stent 112, with prosthetic valve 110 now expanded and delivered (but not positioned or adjusted), as the delivery catheter 144 is withdrawn away from the target location, e.g. atrium.

Figure 10:
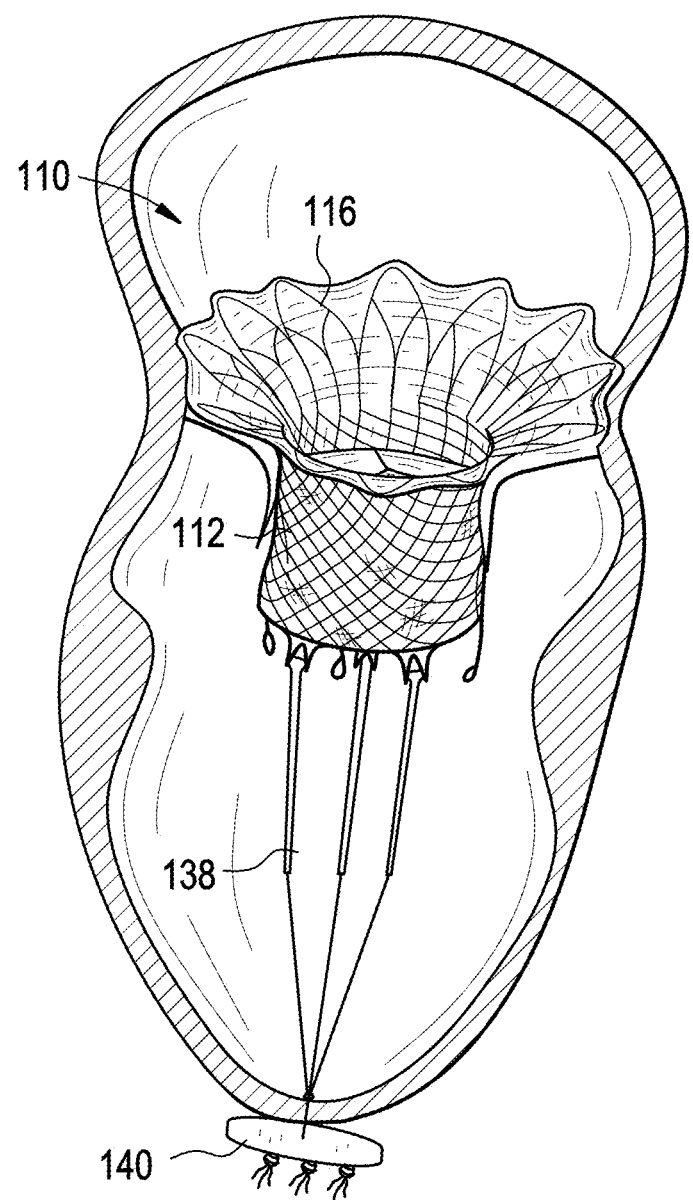
FIG. 10 is a detailed sectional view of one embodiment of a prosthetic valve according to the present invention deployed within the annulus of the mitral valve of the heart and shows that it is anchored using (a) the atrial cuff and (b) the ventricular tethers connected to the apex, which are shown secured by a securing pledget.

Referring now to FIG. 10, FIG. 10 shows a depiction of a fully deployed prosthetic heart valve 110 installed in the left mitral valve of the heart having the tethers 138 attached to the left ventricle apex of the heart. Tethers 138 in this embodiment extend through the heart muscle and are attached to securing device 140, here shown as a pledget placed on the epicardial surface and having tethers fastened thereto. In this embodiment, the pledget 140 performs the function of an anchor to which the tethers 138 are attached. Tethers 138 are strung through the left ventricle apex and pulled downward to seat prosthetic valve 110 in the atrial valve area. The completely installed prosthetic valve is held in the left atrium by the sealing cuff 116 and secured to the apex of the heart by tethers 138. The tethers may be held in place by a securing device which in this aspect of the invention is a pledget 140 that the tethers are threaded through and secured against, i.e. by tying a knot or using a cinching feature.

Figure 11:
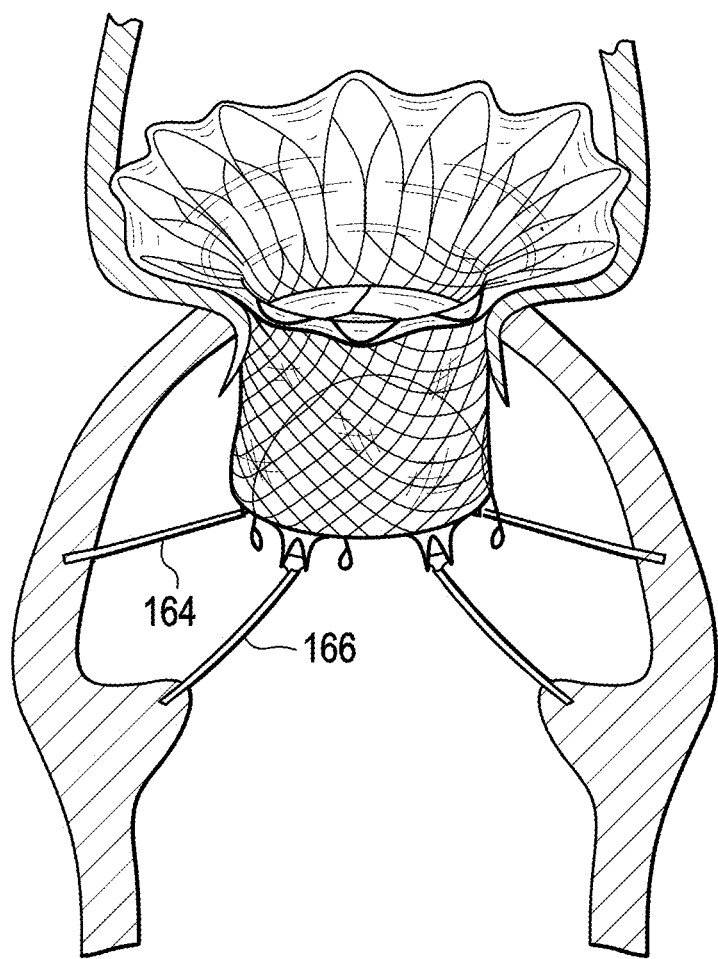
FIG. 11 is a detailed side-perspective view of one embodiment of a prosthetic valve according to the present invention deployed within the annulus of the mitral valve of the heart and anchored using (a) the atrial cuff and (b) the ventricular tethers connected to papillary muscles and/or ventricular wall and/or septum, which are each secured by one or more securing tissue anchors.

Referring now to FIG. 11, FIG. 11 is a detailed cross-sectional view (of the heart) of one embodiment of a prosthetic heart valve according to the present invention deployed within the mitral valve aperture of the heart and anchored, in an alternative embodiment, between (A) where it is seated or lodged by the atrial sealing cuff and (B) the ventricular tethers connected to papillary muscles 166 and/or ventricular wall and/or tether(s) attached to septum 164, which are each secured by one or more securing tissue anchors, anchoring devices, or anchoring methods.

Description of Shuttlecock Annular Valve Figures

Referring now to the FIGURES, FIG. 12 shows one embodiment of a prosthetic heart valve 110 according to the present invention, comprising tubular stent 112 having tether attachment structures 138 and collar 116. Leaflet assembly 118 is disposed within stent 112 and supports leaflets 120 (also not shown).

As stated, tubular stent 112 may be an expandable laser cut stent or an expandable braided stent. Tubular stent 112 may be constructed of Martensitic or super elastic metal alloys. Tubular stent 112 may be compressed in diameter along its longitudinal axis and will fit into a catheter-based stent delivery system. When the tubular stent 112 is delivered to the location where it is to be installed, it is expelled from the catheter by an obturator and deposited at the site where it is to be deployed.

Tubular stent 112 may include a plurality of tether attachments (not pictured) to which a plurality of tethers 138 may be connected. FIG. 12 shows an embodiment having four tether attachments which are integrated into the distal portion of the stent 112, four leading to an pericardial attachment point at the apex of the left ventricle, where the are secured to securing device/pledget 140.

Leaflet assembly 118 is a separate but integrated structure that is disposed within the stent 112. Leaflet assembly 118 functions to provide the structure upon which the valve leaflets or cusps 120 are located. Leaflet assembly 118 may be made entirely of stabilized tissue or it may be a combination wire and tissue structure. Where leaflet assembly 118 is composed entirely of tissue, it is contemplated that the leaflet assembly, leaflet support structure, and leaflets or cusps 120 are made from tissue. It is contemplated as within the scope of the invention that different qualities of stabilized tissue, i.e. thin or thick, structurally rigid or flexible as it may be, may be used for the different components of the collar covering 124, the stent covering, the leaflet assembly 118 and the leaflets 120. Where leaflet assembly 118 is composed of wire and tissue, it contemplated that assembly or support(s), or both, may be made from wire, and the cusps 120 would necessarily be made from tissue.

Prosthetic heart valve 110 also includes collar 116. FIG. 12 shows collar 116 originating at or near the base of the stent body and expanding in diameter within the native valve annulus away from the distal end (ventricular) of the stent body toward the proximal (atrial) end of the stent body.

As stated, collar 116 may be a band of metal tape, a wire structure, made from flexible synthetic material, or made from tissue material, and may be a separate attached structure, or may be constructed as an integral part of the stent body when the stent body is manufactured. Annular tissue is seen exerting lateral pressure onto collar 116. In one embodiment, the collar is an extension of the stent itself, where the stent has been heated and manipulated upon a form to create the extended flat, inverted plate of the collar. In another embodiment, the collar is made separate from the stent 112 and attached as a flat plate constructed to include an inner rim 146 and an outer rim 148, with joint 142 where the collar 116 meets the tubular stent 112.

Referring now to FIGS. 13A-13B, FIG. 13A is a side view illustration showing stent 112, collar 116 and joint 130 located at the distal end of the stent body 116. FIG. 13B is a side view illustration showing an alternate embodiment of stent 112, collar 116 and joint 130 attached further up stent body away from the distal end of the stent body 116.

Referring to the stent body, it is contemplated as within the scope of the invention to include both laser cut stent technology and/or the braided stent technology. Where the collar is an extension of a braided stent and forms a unitary stent-collar construction, the collar is formed by heating a Nitinol (TM) stent on a mold to create the proper extension and angle necessary to establish the collar or collar portion.

Where the stent is laser cut, the collar may be manufactured as a unitary laser-cut stent-collar construction. In this embodiment, the collar wire form and the stent are laser cut within the same overall manufacturing process. Where the collar wire form is made separate from the stent and attached as a flat collar plate, the collar and stent may be manufactured/laser cut separately and attached using laser weld or other similar technique to create a non-fatiguing elastic stent-collar joint capable of maintaining elastic compliance while it is deployed.

As noted, the rim or joint may consist of an artificial transition point between the stent and the collar where the stent has been heated to change the shape and angle of the stent or has been laser cut to create it's overall form, or the rim may consist of a constructed transition point such as a laser welded joint for attaching two component parts.

Referring now to FIGS. 14A-14C, FIG. 14A shows an embodiment of the invention, and in particular, the valve leaflets, whereby a prosthetic mitral valve is supplied. FIG. 14B shows an embodiment of a bicuspid mitral valve made from tissue in the shape a hyperbolic paraboloid, or saddle. This specific shape, for the prosthetic mitral valve, mimics the native valve, and takes into consideration the anterior to posterior compression or deformation that occurs due to adjacent cardiovascular tissues, and takes into consideration the lower, commissural portions similar to the native valve. Since the inventive collar is flexible and deformable, this allows proper alignment of the valve leaflets within the stent body, greatly enhancing functionality. FIG. 14C illustrates how a tricuspid valve may also be used within the scope of the present inventive subject matter.

Referring now to FIG. 15, the collar has the ability to travel or flex in and out, along the lateral axis; longitudinal defined by the lengthwise axis of the stent. As stated, this flexibility or compliance provides the prosthetic heart valve, specifically the collar, upon being deployed within a patient's heart, the ability to conform to the anatomical shape of the native annulus, maintain the conforming shape during the cardiac cycle, and provide a tight seal against the atrial tissue adjacent the mitral valve aperture. This feature reduces or removes the guesswork that often accompanies the pre-surgical sizing of a mitral valve. By providing a better fit, this necessarily prevents blood from leaking around the implanted prosthetic heart valve.

FIG. 15 shows how the prosthetic valve 110 may be fitted with a tissue covering 126 that is thin, durable, and may be attached to the stent body 116. FIG. 15 also shows how the collar 116 may consist in one embodiment as a two-part structure consisting of flexible member 152 and support structure 150. Circular support structure 140 may be made as a disc or halo or series of loops from the stent itself by heat-forming or by laser-cutting, or may be an independent structure that is later attached or welded. In this embodiment, flexible member may be made from a synthetic material such as an elastic polymer fabric like a surgical polyester-linked fabric known in the art. Support structure 150 may be covered with thin tissue 126 such as for example, in a non-limiting preferred embodiment, a 0.005 inch thick tissue made according to the processes disclosed herein. Leaflet cusp 120, here shown internal to the stent 112, may be made of the same tissue material as tissue covering 126. In certain embodiments, leaflet tissue may be processed to provide a thicker or thinner tissue as may demanded by a particular deployment. For example, very thin tissue would be useful where the prosthetic valve is being deployed in a peripheral or non-cardiac vasculature and needs to be very small. In another embodiment, the leaflet tissue may be selected to be thicker to add stability or wear or function, for a particular use.

The prosthetic valve may be sized according to the patient's cardiovascular needs. Smaller patients may need smaller devices. Varying heart anatomies may call for specific sizes also, depending on the pathology presented. In a preferred embodiment, the pericardial stent body is about 28 mm in diameter with support structure 150 extending to about 45 mm in diameter. It is contemplated as within the scope of the invention that the stent body diameter may range from about 2 mm in diameter to about 30 mm in diameter. It is contemplated that the support structure 150 may extend beyond the diameter of the stent body from 0.1 mm to about 20.0 mm, depending on use.

The height may be in one preferred embodiment about 5 mm-15 mm in total body length. It is contemplated as within the scope of the invention that the height range of the prosthetic valve length may range from about 2 mm to about 30 mm in total body length. The tethers may comprise from 1 to about 96 tethers securing the prosthetic valve in place. In one embodiment, there may be a plurality of tethers 138 integrated with the stent body.

Stent 112 may include a liner contemplated as being made of tissue or biocompatible material as disclosed herein. The stent liner may be an inner stent liner and/or an outer (surface) stent liner.

Referring now to FIG. 16, an alternate preferred embodiment is illustrated showing stent body 112 covered with treated thin tissue 126, collar 116 made from a polyester or polyester-type fabric mesh which spans from support structure 140 to the distal end of the stent body 112. Support structure 140 is also covered with thin (e.g. 0.005", 0.127 mm) tissue 126. Multiple tethers 114 are shown attached to tether posts 144, and anchored to cardiac tissue as well as an elongated tether 138 connected apically to a pericardial pledget 146. Saddle shaped bicuspid leaflet 118 is shown disposed within stent body 112.

Referring now to FIG. 17 is a cut-away view of a heart with a delivery catheter containing a prosthetic heart valve according to the present invention and accessing the heart using an apical approach. It is contemplated that other surgical approaches to the heart, and valves in addition to the mitral valve, are within the scope of the inventive subject matter claimed herein. FIG. 17 shows the delivery catheter 144 advanced to through the mitral valve and into the left atrium for deployment of the prosthetic valve 110.

Referring now to FIG. 18, FIG. 18 shows the lateral deployment of one embodiment of a prosthetic valve according to the present invention and shows a prosthetic valve delivery catheter that has accessed the left atrium via the left ventricle by way of a lateral trans-ventricular wall approach through the lateral wall of the left ventricle of the heart. FIG. 18 shows a prosthetic valve delivery catheter 144 that has accessed the left atrium via the left ventricle by way of a lateral trans-ventricular wall approach through the lateral wall of the left ventricle of the heart for deployment of the prosthetic valve 110.

Referring now to FIG. 19 is a cut-away view of a heart with a delivery catheter containing a prosthetic heart valve according to the present invention and accessing the heart using an apical approach into the right ventricle. It is contemplated that other surgical approaches to the heart including, and without being limited to, are femoral artery access, axillary artery access, brachial artery access, radial artery access, intrathoracic/pericardial, and other access methods. It is also contemplated that valves in addition to the mitral valve, are within the scope of the inventive subject matter claimed herein, such as for instance the tricuspid and the aortic. FIG. 19 shows the delivery catheter 144 advanced to the tricuspid valve and into the right atrium for deployment of the prosthetic valve 110.

Figure 20A:
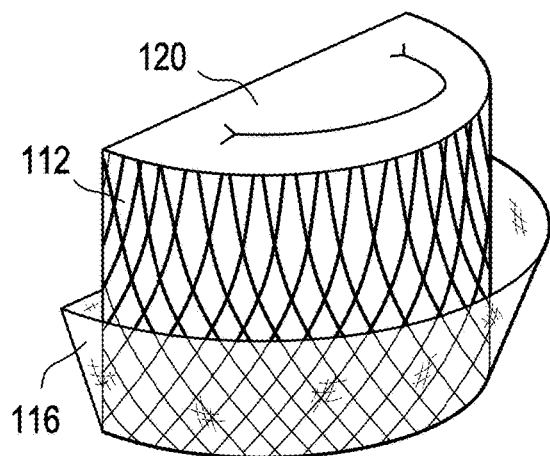
Figure 20B:
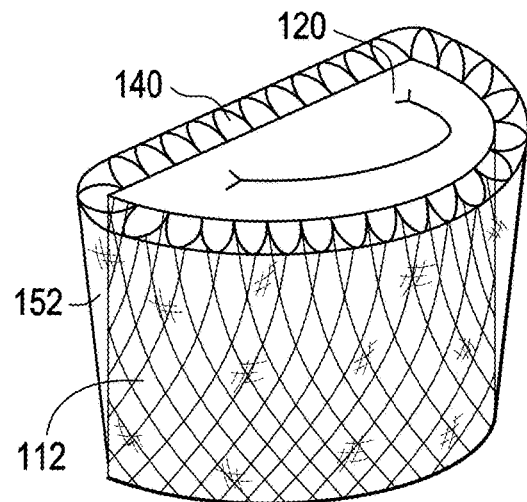
Figure 20C:
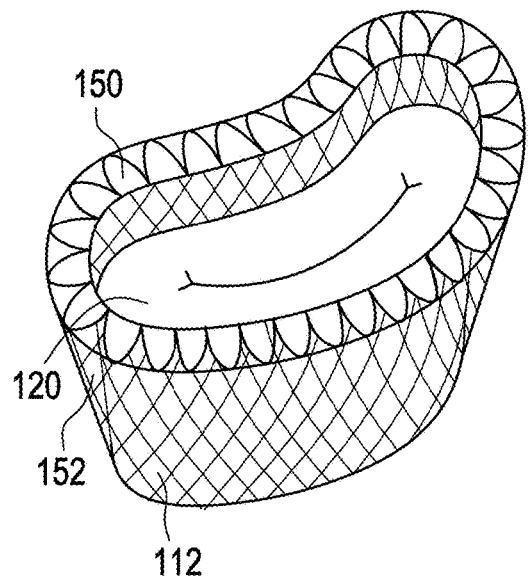
Figure 20D:
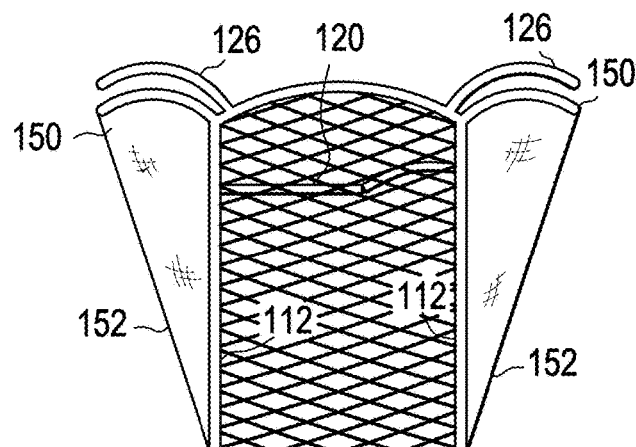

Referring now to FIGS. 20A-20D, FIG. 20A is a D-shaped embodiment of a prosthetic valve according to the present invention. FIG. 20A shows stent 112 having collar 116 and mitral leaflets 120. Mitral leaflets 120 are shown at or near the top of stent 112 providing a mechanism for avoiding LVOT as described earlier. FIG. 20B shows another D-shaped embodiment of a prosthetic valve according to the present invention. FIG. 20B shows flexible member 152 covering stent 112 and spanning between stent 112 and support structure 150. Flexible member 152 and support structure 150 together comprise an alternative preferred embodiment of a collar 116. Support structure 150 is shown as a border of loops. As previously described, support structure may be formed directly out of the stent material, laser cut from a unitary piece of Nitinol®, or attached separately. Support structure 150 is shown here in this example without a layer of tissue or fabric, but it may also be covered as such. Again, mitral leaflets 120 are shown at or near the top of stent 112 providing a mechanism for avoiding LVOT as described earlier. FIG. 20C is an illustration of a kidney or kidney-bean shaped embodiment of a prosthetic valve according to the present invention. FIG. 20C shows flexible member 152 covering stent 112 and spanning between stent 112 and support structure 150. Flexible member 152 and support structure 150 together comprise an alternative preferred embodiment of a collar 116. Support structure 150 is shown as a border of loops. FIG. 20D is a cross-sectional view of an embodiment of a prosthetic valve according to the present invention. FIG. 20D shows leaflets 120 disposed within the lumen formed by stent walls 112. Support structure 140 is shown formed from and an integral piece of stent 112. Flexible member 152 is seen spanning between the distal end of stent 112 and the proximal end of support structure 150. Support structure 150 is shown covered by stabilized tissue 126.

Description of Spring Anchor Figures

Referring now to the FIGURES, FIG. 21 is a perspective view illustration evidencing one embodiment of a prosthetic heart valve 110 according to the present invention, comprising tubular stent 112 having spring anchor attachment 156 attached to stent base 154. Leaflet assembly 118 is disposed within stent 112.

As stated, tubular stent 112 may be an expandable laser cut stent or an expandable braided stent. Tubular stent 112 may be constructed of Martensitic or super elastic metal alloys. Tubular stent 112 may be compressed in diameter along its longitudinal axis and will fit into a catheter-based stent delivery system. When the tubular stent 112 is delivered to the location where it is to be installed, it is expelled from the catheter by an obturator and deposited at the site where it is to be deployed.

Tubular stent 112 includes spring anchor attachment 156. FIG. 21 shows an embodiment having the spring anchor attachments wherein the proximal loop of the coil is attached to the stent base 154, and the non-proximal loops extend out from such base in a spring shape.

Referring now to FIG. 22, FIG. 22 is a perspective view illustration showing stent 112 seated within a native mitral valve annulus with leaflet assembly 118 disposed within stent 112. Stent base 154 appears beneath the native annulus and within the chordae tendineae, where it is fused to the proximal loop of spring anchor 158. Spring Anchor 156 extends outward from its proximal loop and each non-proximal loop encircles the chordae tendineae.

As noted, the stent base 154 may comprise an artificial transition point between the stent and the spring anchor proximal loop 158, which transition point may consist of a welded attachment, a soldered attachment, or an adhesive attachment.

As previously discussed, spring anchor 156 has the ability to travel or flex both in and out, and up and down, as required by the movements in the cardiac tissue associated with heart contraction, while moving back into its natural spring-like shape with each heart muscle relaxation. As stated, the pliability of anchor 156 provides the prosthetic heart valve, upon deployment within a patient's heart, with added stability within the native annulus, enhancing the ability of stent 112 to both maintain a conforming shape during the cardiac cycle, and provide a tight seal against the atrial tissue adjacent the mitral valve aperture. By providing an anchor with characteristics to stent 112, the potential for blood leakage around the implanted prosthetic heart valve is minimized, as is the potential for the stent to dislodge into either the ventricle or atrium, resulting in catastrophic failure.

Referring now to FIGS. 23A-23C, FIG. 23A shows an embodiment of the invention, and in particular, the valve leaflets, whereby a prosthetic mitral valve is supplied. FIG. 23B shows an embodiment of a bicuspid mitral valve made from tissue in the shape a hyperbolic paraboloid, or saddle. This specific shape, for the prosthetic mitral valve, mimics the native valve, and takes into consideration the anterior to posterior compression or deformation that occurs due to adjacent cardiovascular tissues, and takes into consideration the lower, commissural portions similar to the native valve. Since the inventive collar is flexible and deformable, this allows proper alignment of the valve leaflets within the stent body, greatly enhancing functionality. FIG. 23C illustrates how a tricuspid valve may also be used within the scope of the present inventive subject matter.

Referring now to FIG. 24, stent 112 is again seated within a native mitral valve annulus, here seen in cross-section, with valve leaflet assembly 118 disposed within stent 112. In addition, mesh collar 116 has been attached to the proximal end of stent 112 for additional stability above the native annulus. Stent base 154 is fused to the spring anchor proximal loop 158, while the non-proximal loops of spring anchor 156 extend downward through the ventricle and around the chordae tendineae (not shown here). In addition, tethers 138 are attached to the fused stent base 158/spring anchor proximal loop 154, and extend outward in multiple directions where they are anchored into surrounding native tissue. Several of tethers 138 are extended to the apex of the left ventricle for attachment to and through a pledget 140 on the pericardial surface. Tethers 138 and spring anchor 156 may be used separately or in conjunction to provide stabilization to stent 112.

Referring now to FIG. 25, FIG. 25 is a cut-away view of a heart with a delivery catheter containing a prosthetic heart valve with attached spring anchor according to the present invention and accessing the heart using an apical approach. It is contemplated that other surgical approaches to the heart, and valves in addition to the mitral valve, are within the scope of the inventive subject matter claimed herein. FIG. 25 shows the delivery catheter 144 advanced to through the mitral valve and into the left atrium for deployment of the prosthetic valve 110 and attached spring anchor 156, and rotating to encircle the spring-shaped spring anchor 156 around the chordae tendineae (not shown).

Referring now to FIG. 26, FIG. 26 shows the lateral deployment of one embodiment of a prosthetic valve 110 prior to release of spring anchor 156 (not shown) according to the present invention and shows a prosthetic valve delivery catheter 144 that has accessed the left atrium via the left ventricle by way of a lateral trans-ventricular wall approach through the lateral wall of the left ventricle of the heart. FIG. 26 shows a prosthetic valve delivery catheter 144 that has accessed the left atrium via the left ventricle by way of a lateral trans-ventricular wall approach through the lateral wall of the left ventricle of the heart.

Referring now to FIG. 27, FIG. 27 is a cut-away view of a heart with a delivery catheter 144 containing a prosthetic heart valve 110 according to the present invention and accessing the heart using an apical approach into the right ventricle. It is contemplated that other surgical approaches to the heart, and valves in addition to the mitral valve, are within the scope of the inventive subject matter claimed herein. FIG. 27 shows the delivery catheter 144 advanced to the tricuspid valve and into the right atrium for deployment of the prosthetic valve 110, prior to release of spring anchor 156 (not shown).

Description of Annular Clamps Figures

FIG. 28A shows a perspective view of a wire stent 112 with four clamp-style annulus anchoring members 160 located around the outside. FIG. 28B shows a side view of the same wire stent 112 with four clamp-style annulus anchoring members 160.

FIG. 29 shows a side view of a closed clamp-style annulus anchoring member 160.

FIG. 30A show a perspective view of a clamp-style annulus anchoring member 160 in the open position, comprising the following parts: pin 162, spring 168, two inter-digitated middle members 170, two pairs of semicircular fingers 172, each with a tapered point 174. FIG. 30B shows a perspective view of the same clamp shown in FIG. 30A, but in the closed position with the ends of the semicircular fingers 172 interdigitated.

FIG. 31A shows a side view of the clamp-style annulus anchoring member 160 shown in FIG. 30A, but with a pressure-bearing member 176 attached to the flange portion of each middle member 170 via the hole centered in such flange (not shown), and exerting pressure to hold the clamp open. The pressure bearing members 176 are emanating from a catheter 144 in a straight position, exerting outward pressure on the clamp to hold it open. FIG. 31B shows a partially exploded view of the clamp and pressure bearing members 176, evidencing the holes 178 centered in the middle member flanges and the attachment stud 180 of each pressure bearing member. The figure shows the moment of release as the crimped point of the pressure bearing members 176 extend from catheter 144 and cause the pressure bearing members to release from the middle members 170 of the clamp, thereby allowing the torque of spring 168 (not shown) to snap the clamp shut.

FIG. 32A shows a perspective view of a single semicircular finger 172, with a slot 182 along the outer ridge and a series of triangular protrusions 184 along one side for interlocking with another finger of the same design. FIG. 32A also evidences a tip barb 186 above tapered point 174, for securing the clamp into native tissue. FIG. 32B shows a side view of the same semicircular finger pictured in FIG. 32A.

FIG. 33A shows a perspective view of the outer and distal side of the center portion component of a middle member of the clamp assembly shown in FIG. 30A, with machine tooling slots 188 and a ridged locking mechanism 190 for interlocking with other components of the clamp assembly, as well as stud attachment 192. FIG. 33B shows a perspective view of the inner and distal side of the same center portion component pictured in FIG. 33A.

FIG. 34A shows a perspective view of a clamp assembly in the open position, comprising a set of four closing members 174, each with a hole bored directly into its proximal end through which a pin 162 has been threaded, with the closing members 174 interdigitated such that the first and third closing members close in one direction while the second and fourth closing members close in the opposite direction. Each closing member has a tapered distal tip 174. FIG. 34B shows the same assembly as FIG. 34A, but in the closed position.

FIG. 35A shows a side perspective of a clamp assembly in the open position, comprising a set of four closing members 170, each with a hole bored directly into its proximal end through which a pin 162 has been threaded, with the closing members 170 interdigitated such that the first and third closing members close in one direction while the second and fourth closing members close in the opposite direction. Each closing member has a tapered distal tip 174 with a barb feature 186. FIG. 35B shows the same assembly as FIG. 34A, from an angled perspective.

FIG. 36A shows a side view of the clamp assembly of FIG. 35A, but in a closed position. FIG. 36B shows the same assembly as FIG. 36A, but from an angled perspective.

FIGS. 37A-37F show a variety of possible dimensions of various components of a clamp assembly.

FIG. 38 shows a wire stent 112 with an integrated cuff 116 comprising stud assemblies 192 for a suction fin and glue fin.

FIG. 39 shows a cross-section of the integrated cuff 116 of the stent of FIG. 38, evidencing two stable inner tubes 194 for suction and application of glue.

FIG. 40 is a line drawing evidencing the angle of stent 112 to semicircular finger 172.

FIG. 41 is a perspective view from an underneath angle of a wire stent 112 comprising an integrated cuff 116, further evidencing a series of clamping devices 196 circumnavigating the prosthetic annulus, each such device clamping down a security belt 198.

FIG. 42 evidences a perspective view of a guidance catheter 144 located within the stent 112 pictured in FIG. 41, with wires 200 emanating from holes around the catheter body 202 and attached through the prosthetic annulus to the clamp devices (not pictured) pictured in FIG. 41.

FIG. 43 shows a closer view of the guide catheter 144, stent 112 and strings 200 emanating from catheter holes 202, connecting to security belt clamps 196 as they secure security belt 198.

FIG. 44 shows an underneath view of the guidance catheter, string and stent assembly of FIGS. 41-43, evidencing the mechanism by which pulling the strings 200 through the catheter holes 202 closes the clamp devices 196 around the security belt 198.

FIG. 45 shows a close view from a perspective inside the stent of the guidance catheter, string and stent assembly of FIGS. 41-44, evidencing a cross-section of the guidance catheter 144 and a cross-section of the integrated cuff 116, evidencing the perforation of the cuff by each string 200 and the connection of each string 200 to a clamping device 196, which clamps security belt 198 into place.

Description of Improved Cuff/Collar Figures

Referring now to the FIGURES, FIG. 46 shows the atrial cuff/collar 116 wherein the shape is somewhat mushroom shaped, or agaricoid. In this embodiment, hemodynamic leaking is addressed wherein the atrial cuff/collar 116 has been constructed to have a tensioning or downward-spring feature 204 in order to contour to the commissures of a pathologically defective mitral valve and constructed to contour to the zone of coaptation of the pathologically defective mitral valve. The commissural contour components at each down-turned end of the atrial sealing gasket and the zone of coaptation contour components of the atrial cuff/collar 116 act to confirm to the saddle-shape wherein the commissural contour components are in direct communication with the mitral valve commissures, and the zone of coaptation contour components are in direct communication with the mitral valve zone of coaptation FIG. 47 shows the atrial cuff/collar 116 wherein the shape is "fingernail shaped" or onychoid. In this embodiment, the truncated portion is positioned during deployment adjacent to the aortic valve area. The rounded portion then is seated and covers the posterior commissure while the truncated portion avoids obstruction by the lacking the surplus of cuff material that would define an interfering structure.

FIG. 48 shows the atrial cuff/collar 116 wherein the shape is "kidney shaped" or reniform. In this embodiment, the inner curve of the shape is positioned during deployment to face the aortic valve area (anteriorly) and obstruction is avoided by the lack of an interfering structure. In contrast, additional gasket material is provided so that the gasket may be seated to cover both commissural areas of the mitral valve. The outer curve of the atrial cuff/collar 116 functions to prevent leakage near the zone of coaptation.

FIG. 49 shows the atrial cuff/collar 116 wherein the shape is an oval. In this embodiment, the anterior rounded portion 212 is positioned during deployment adjacent to the aortic valve area and rises to travel along the atrial wall to provide sealing without obstruction. The posterior rounded portion 214 then is seated and covers the commissures and seals against leaking.

FIG. 50 shows the atrial cuff/collar 116 wherein the shape is a truncated-oval having a squared, truncated portion 206. Similar to FIG. 47, in this embodiment, the truncated portion 206 is positioned during deployment adjacent to the aortic valve area, but also comprises a curved aspect 216 that rises to travel along the atrial wall to provide sealing without obstruction. The rounded portion 216 then is seated and covers the posterior commissure while the truncated portion 206 avoids obstruction by the lacking the surplus of cuff material that would define an interfering structure.

FIG. 51 shows the atrial cuff/collar 116 as an acute (downward) angle sealing structure. In this embodiment, the atrial sealing gasket has a tensioning or spring-like feature similar to FIG. 46, but with a atrial cuff profile that is about 1 cm or less. Although the small cuff/collar 116 may have less ability to seal against leaking as a consequence of its smaller size, the benefit of the smaller profile is that there is less wear, less movement, less inflammation, and less damage to the atrial tissue.

FIG. 52 shows the atrial cuff/collar 116 and the internal valve leaflets at nearly that same planar location/height. In this embodiment, the cuff/collar 116 allows the prosthetic valve leaflet assembly 118 to be seated within the mitral annulus at an optimum height, balancing avoiding LVOT obstruction below the annulus while providing the ability to vary the functionality of the ventricular filling.

FIG. 53 shows the atrial cuff/collar 116 wherein the shape is propeller-shaped. In this embodiment, the atrial cuff/collar 116 is positioned during deployment such that where the gasket is at a minimum, the aortic valve area (anteriorly) has little or no pressure from the prosthetic valve 110 against the annular tissue adjacent the aortic valve. In contrast, the "blades" of the propeller shape provide additional cuff material so that the gasket may be seated to cover both commissural areas of the mitral valve. In this embodiment, no additional cuff material is provided near the zone of coaptation and the native leaflets provide sufficient sealing against leaking. There may be two or three "blades" in the propeller structure.

FIG. 54 shows the atrial cuff/collar 116 wherein the shape is cruciform. In this embodiment, the atrial cuff/collar 116 is positioned during deployment such that there is cuff material provided to place a specified amount of pressure on the annular tissue adjacent the aortic valve. Similar to FIG. 53, the "blades" of the propeller shape provide additional cuff material so that the gasket may be seated to cover both commissural areas of the mitral valve.

FIG. 55 shows the atrial cuff/collar 116 wherein the shape is petal-shaped having a plurality of flat radial covered loops. In this embodiment, the atrial cuff/collar 116 and the internal valve leaflets 118 are at nearly that same planar location/height allowing the prosthetic valve to be seated within the mitral annulus at an optimum height, balancing avoiding LVOT obstruction below the annulus while providing the ability to vary the functionality of the ventricular filling. In this embodiment, the use of multiple radial loops allows the atrial gasket to match the trabeculations of the atrial/annular tissue area.

FIG. 56 shows the atrial cuff/collar 116 wherein the shape is petal-shaped having a plurality of flat radial covered stellate loops. Similar to FIG. 55, in this embodiment, the use of multiple radial loops allows the atrial gasket to match the trabeculations of the atrial/annular tissue area.

FIG. 57 shows the atrial cuff/collar 116 wherein the shape is petal-shaped having s plurality of flat radial covered stellate loops illustrating how they can travel longitudinally to effectuate sealing.

FIG. 58 shows the atrial cuff/collar 116 wherein the shape is irregular or amoeboid. This type of customized atrial cuff/collar may be useful where a specific pathology or anatomy presents the need for a specific structural solution.

FIG. 59 shows the atrial cuff/collar 116 wherein the shape is cup-shaped, or chair-shaped, known as cotyloid shaped. In this embodiment, the anterior portion is positioned during deployment adjacent to the aortic valve area and rises to travel along the atrial wall to provide sealing without obstruction. The posterior rounded portion then is seated and covers the commissures and seals against leaking. Similar to FIG. 53, in this embodiment, no additional cuff material is provided near the zone of coaptation and the native leaflets provide sufficient sealing against leaking.

FIG. 60 shows the atrial cuff/collar 116 wherein the shape is a partial half-round fan-shape. Similar to FIG. 50, the rounded portion is seated into the valve annulus and covers the posterior commissure while the missing portion avoids obstruction by the lacking the surplus of gasket material that would define an interfering structure.

FIG. 61 shows the atrial cuff/collar 116 with an upturned flat U-shaped planar rectangle. In this embodiment, the "short" sides are positioned anteriorly and posteriorly while the upturned portions provide a tensioning surface against the commissural area.

FIG. 62A shows a side view and FIG. 62B shows a front perspective view of one embodiment showing the atrial cuff/collar 116 attached to the stent body at a forward angle, posterior to anterior.

Description of Improved Stent Figures

Referring now to the FIGURES, FIG. 63A is a perspective view of the saddle shape of a native mitral valve leaflet structure or of a prosthetic valve leaflet structure according to the present invention. Thus, it becomes quickly apparent that a standard prosthetic valve made only of a straight tubular stent having flat bicuspid valve leaflets will impose structural, and therefore functional limitations on any prior standard devices. FIG. 63B is a drawing of the three-dimensional relative position of the mitral valve compared to the X-Y-Z axis and shows that the mitral valve is aligned off-axis. Specifically, the mitral valve is (reference is made to the FIG. 63B for a more accurate description) positioned left of center along the horizontal X-axis and slightly rotated around the X-axis, it is below center along the vertical Y-axis and rotated slightly clockwise around the Y-axis, and it is tipped slightly left to right around the Z-axis, all in a structure that is roughly saddle-shaped. These teachings applied to the preparation of a pre-configured/pre-contoured stent provide one of the important features of the present invention.

FIG. 63C is a drawing of a side view representation of a mitral valve showing the range of movement of the anterior and posterior leaflets from closed to opened. The larger anterior leaflet (left) joins the smaller posterior leaflet (right) at the beginning of ventricular systole (contraction) and dashed lines represent the open mitral valve during passive and active ventricular diastole (filling). As seen in FIG. 63C, the anterior and posterior leaflets extend ventricularly to a substantial degree.

FIG. 63D is a graphical three-dimensional representation of a mitral valve with approximate orientation and sizes in all three dimensions. FIG. 63D shows the saddle shaped valve to be an average size of about 0.5 cm in height, about 6.0 cm from side to side, and about 1.5 cm in width. Of course, this varies by patient and may also vary due to pathological condition. Thus, a prosthetic stent must take into consideration these factors to provide a prosthetic that is nearly optimized to function as a healthy, native mitral valve.

FIG. 64 is a drawing of the heart in cross-section showing the positional relationship of the mitral and tricuspid valves to the pulmonic and aortic arteries. FIG. 64 shows mitral valve 218, tricuspid valve 220, aortic valve 222, and pulmonic valve 224. FIG. 64 shows how a prosthetic mitral valve that does not have a tailored, pre-contoured shape can interfere with the operation of the other valves due to spatial hindrances.

FIG. 65A is a perspective drawing of one embodiment according to the present invention showing a prosthetic mitral valve 110 having a kidney-shaped (epicyclic, cardioid) stent conformation 112 in cross-section with an atrial cuff 116, shown here as opaque for stent detail. Thus, having a kidney-shaped stent body is intended to address LVOT (left ventricular outflow tract) obstruction and other spatial obstructions that would interfere with optimal valve function. Prosthetic valve leaflets 118 are shown in FIG. 65A as positioned down within the stent body 112 a specific distance from the top.

FIG. 65B is a perspective drawing of one embodiment according to the present invention illustrating a prosthetic mitral valve 110 having a rounded-shape or oval-shape stent 112 conformation in cross-section with valve leaflets 118 positioned towards the middle-point halfway up within the stent body 112, and with an atrial cuff 116, shown here as opaque for stent detail.

FIG. 66 is a perspective drawing of one embodiment according to the present invention showing a prosthetic mitral valve 110 having a curved-tubular shape stent conformation 112 in cross-section with an atrial cuff 116, shown here as opaque for stent detail. By curving away from possible spatial obstruction, this stent shape is also intended to address spatial valve or flow obstruction issues.

FIG. 67 is a perspective drawing of one embodiment according to the present invention showing a prosthetic mitral valve 110 having a rounded-shape or oval-shape stent conformation 112 in cross-section with prosthetic valve leaflets 118 positioned high in the stent toward the atrial end of the stent body, and an atrial cuff 116, shown here as opaque for stent detail. FIG. 67 shows an embodiment having a low-profile as to the height of the device. This embodiment is intended to have a stent body 112 that will remain substantially within the annular space and does not extend beyond the distance of the open native valve leaflets (not pictured). Further, having the prosthetic valve leaflets 118 positioned high within the stent body 112 provides additional advantages over prosthetic valves where the prosthetic valve leaflets are located further down within the stent body.

FIG. 68 is a perspective drawing of one embodiment according to the present invention showing a prosthetic mitral valve 110 having a stent body 112 made from both braided wire 228 (atrial end) and laser-cut metal 226 (annular or ventricular end), and an uncovered atrial cuff 116.

FIG. 69 is a perspective drawing of one embodiment according to the present invention showing a prosthetic mitral valve 110 having a stent body 112 made from both laser-cut metal 226 (atrial end) and braided wire 228 (annular or ventricular end), and without an atrial cuff.

As stated, the stent may be an expandable laser cut stent or an expandable braided stent and may be constructed of Martensitic or super elastic metal alloys. The stent/valve assembly may be compressed along its longitudinal axis and will fit into a catheter-based stent delivery system. When the stent/valve is delivered to the location where it is to be installed, it is expelled from the catheter by an obturator and deposited at the site where it is to be deployed.

The stent may include a plurality of tether attachments upon which a tether may be connected. The leaflet assembly is a separate but integrated structure that is disposed within the stent body. Leaflet assembly functions to provide the structure upon which the valve leaflets or cusps are located. Leaflet assembly may be made entirely of stabilized tissue or it may be a combination wire and tissue structure. It is contemplated as within the scope of the invention that different qualities of stabilized tissue, i.e. thin or thick, structurally rigid or flexible as it may be, may be used for the different components of the cuff covering, the stent covering, the leaflet assembly and the leaflets.

Prosthetic heart valve may also include a cuff. In one embodiment, the cuff "wire form" is an extension of the stent itself, where the stent has been heated and manipulated upon a form to create the extended spindles of the flat, collar plate of the cuff. In another embodiment, the cuff "wire form" is made separate from the stent and attached as a flat collar plate with independent loops of wire that create lobes or segments extending radially/axially around the circumference of the inner rim, the joint where the cuff meets the tubular stent.

As contemplated, the deployment of one embodiment of a prosthetic valve according to the present invention includes an embodiment of a delivery catheter according to the present invention containing a pre-loaded prosthetic valve which is being pushed out of the delivery catheter, i.e. by an obturator, starting with (A) the valve completely within the catheter, (B) the cuff portion being in view, (C) the stent body following, and (D) the prosthetic valve with attached tethers for positioning and/or adjustment and/or securing the valve to tissue.

Description of Narrow Gauge Stent Figures

Referring now to the FIGURES, FIG. 70 is a line drawing evidencing the native mitral valve 218 without a prosthetic implant. Anterior leaflet 230, posterior leaflet 232, anterolateral commissures 234 and posterior commissures 236 are shown. The tips of the anterior and posterior commissures have been marked for reference.

FIG. 71 shows how a prosthetic valve 110 that is sized solely based on the native annulus results in an over-sized prosthetic valve that stretches or tears the native commissures 234 and 236 open, preventing them from performing their native sealing, which is often not overly affected in pathological conditions and may retain some native sealing function.

FIG. 72 shows how a prosthetic mitral valve 110 that is sized to avoid interaction with or deformation of the commissures can be used to treat mitral regurgitation at the central jet, without having the solution, the valve, cause addition problems itself. Note how anterolateral commissure 234 defined by P1-A1 portions of the leaflet remain intact for sealing, and how posteromedial commissure 236 defined by P3-A3 portions of the leaflet also remain intact for sealing.

FIG. 73 shows an even narrower diameter prosthetic valve 110 being used, especially in a functional mitral regurgitation patient that does not need necessarily 100% sealing to achieve beneficial effects of the implant. Note also that prosthetic valves may be configured to have 2-, 3-, or 4-leaflet valve structures.

FIG. 74 shows how the hyperbolic paraboloid shape of the native mitral valve yields different diameters, whether posterior to anterior, or longitudinal along the line of the cusp interface. Here, the goal of avoiding deformation of the commissural leaflets is exemplified, without necessarily limiting the invention herein, as a mathematical ratio whereby line a-a exemplifies a diameter that is too large, but that line c-c, across the cross-section of the leaflets, illustrates one preferred example of the invention.

FIG. 75 shows how an over-large valve extends beyond line c-c, and could, if the longest diameter were inadvertantly used, the full diameter of the native annulus line a-a, that it extends even further beyond what is believed to be too large of a valve diameter (in some situations).

FIG. 76 and FIG. 77 show positive examples of the concept disclosed herein, where the diameter is either equal to or less than the cross-section diameter of the native annulus from posterior to anterior side.

FIG. 78 shows one non-limiting embodiment of the prosthetic valve 110 which has been deployed in the native mitral annulus. FIG. 9 shows cuff 116 and stent body 112, along with tethers 138 and epicardial anchor 140. The dashed line illustrates how the present invention may be constructed having a significantly narrower stent body that standard prosthetic valves of the this class, while maintaining standard-sized cuff, internal valve assembly, and tether features.

In this embodiment of a prosthetic heart valve according to the present invention, there is a tubular stent having tether attachment structures at one end and tubular stent is attached to cuff at the other end. Leaflet assembly (not shown) is disposed within stent and supports leaflets (also not shown). Cuff has independent articulating loops of wire and a covering.

As stated, tubular stent 112 may be an expandable laser cut stent or an expandable braided stent. Tubular stent 112 may be constructed of Martensitic or super elastic metal alloys. Tubular stent 112 may be compressed along its longitudinal axis and will fit into a catheter-based stent delivery system. When the tubular stent 112 is delivered to the location where it is to be installed, it is expelled from the catheter by an obturator and deposited at the site where it is to be deployed.

Tubular stent 112 includes a plurality of tether attachments 138 upon which a tether, shown, may be connected. FIG. 78 shows an embodiment having three tether attachments 138 which are integrated into the distal portion of the stent. In this embodiment, the tethers extend from the stent, through the pericardial and epicardial tissue and are tied off at a pledget, button or similar type of anchor 140 on the outside of the heart. Such anchor 140 may itself be comprised of or covered with stabilized tissue.

Leaflet assembly 118 is a separate but integrated structure that is disposed within the stent. Leaflet assembly 118 functions to provide the structure upon which the valve leaflets or cusps are located. Leaflet assembly 118 may be made entirely of stabilized tissue and/or polymeric fabric, or it may be a combination wire and tissue/fabric structure. Where leaflet assembly is composed entirely of tissue, it is contemplated that the leaflet assembly, leaflet support structure, and leaflets or cusps are made from tissue. It is contemplated as within the scope of the invention that different qualities of stabilized tissue, i.e. thin or thick, structurally rigid or flexible as it may be, may be used for the different components of the cuff covering, the stent covering, the leaflet assembly and the leaflets. Where leaflet assembly 118 is composed of wire and tissue, it contemplated that assembly or support(s), or both, may be made from wire, and the cusps would necessarily be made from tissue.

In one embodiment, the cuff wire form 116 is an extension of the stent 112, where the stent has been heated and manipulated upon a form to create the extended spindles of the flat, collar plate of the cuff. In another embodiment, the cuff wire form 116 is made separate from the stent 112 and attached as a flat collar plate constructed to include an inner rim and an outer rim, with independent loops of wire that create lobes or segments extending axially around the circumference of the inner rim, the joint where the cuff meets the tubular stent.

INCORPORATION AND EQUIVALENTS

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed is:

1. An apparatus, comprising:
  an anchor device disposable at least partially on a ventricle side of a native valve annulus of a heart and having a spring-shape when deployed within the heart;
  a prosthetic heart valve including a stent body having an atrial end and an opposite, ventricle end, the heart valve configured to be implanted within the native valve annulus with the stent body adjacent to the anchor device to secure a position of the stent body within the native valve annulus; and
  a set of valve leaflets disposed within a lumen defined by the stent body and configured to permit blood flow through the stent body from the atrial end to the ventricle end of the stent body and to inhibit blood flow from the ventricle end to the atrial end of the stent body when the prosthetic heart valve is disposed within the native valve annulus,
  wherein the anchor device is configured to encircle chordae tendineae of the heart.

2. The apparatus of claim 1, wherein the anchor device includes at least two coil turns.

3. The apparatus of claim 1, wherein the anchor device is formed with a shape-memory material.

4. The apparatus of claim 1, wherein the anchor device includes coils that have a greater circumference than a circumference of the stent body.

5. The apparatus of claim 1, wherein the anchor device includes a plurality of coils that all have an equal circumference.

6. The apparatus of claim 1, wherein the anchor device includes a plurality of coils, each successive coil from the plurality of coils having a circumference that increases successively in a direction away from the stent body.

7. The apparatus of claim 1, wherein the anchor device is configured to be collapsed into a delivery catheter for delivery to a heart.

8. The apparatus of claim 1, wherein the anchor device is covered with biocompatible stabilized tissue or synthetic material.

9. An apparatus, comprising:
  an anchor device for use in securing a position of a prosthetic heart valve stent within a native annulus of a heart, the anchor device having a biased spring-shape and configured to be disposed at least partially around a ventricle side of a native valve apparatus of the heart upon deployment within the heart,
  wherein the anchor device is configured to be disposed at least partially around chordae tendineae of the heart upon deployment within the heart.

10. The apparatus of claim 9, wherein the anchor device is configured to be disposed adjacent the prosthetic heart valve stent when deployed within the heart.

11. The apparatus of claim 9, wherein the anchor device includes at least two coil turns.

12. The apparatus of claim 9, wherein the anchor device is formed with a shape-memory material.

13. The apparatus of claim 9, wherein the native valve apparatus includes leaflets and chordae tendineae of the heart.

14. The apparatus of claim 9, wherein the anchor device includes a plurality of coils that all have an equal circumference.

15. The apparatus of claim 9, wherein the anchor device includes a plurality of coils, each successive coil from the plurality of coils having a circumference that increases successively in a direction away from the native annulus of the heart when disposed within the heart.

16. The apparatus of claim 9, wherein the anchor device is configured to be collapsed into a delivery catheter for delivery to a heart.

17. The apparatus of claim 9, wherein the anchor device is covered with biocompatible stabilized tissue or synthetic material.

\* \* \* \* \*